US 8,658,354 B2

(12) United States Patent
Kida et al.

(10) Patent No.: US 8,658,354 B2
(45) Date of Patent: Feb. 25, 2014

(54) ANTI-(INFLUENZA A VIRUS SUBTYPE H5 HEMAGGLUTININ) MONOCLONAL ANTIBODY

(75) Inventors: Hiroshi Kida, Sapporo (JP); Yoshihiro Sakoda, Sapporo (JP); Eiji Miyagawa, Tokyo (JP); Nobuyuki Fujii, Tokyo (JP); Yoshiaki Uchida, Tokyo (JP); Takashi Shirakawa, Tokyo (JP); Hiroyuki Kogaki, Tokyo (JP)

(73) Assignees: National University Corporation Hokkaido University, Sapporo-Shi; Fujirebio Inc., Tokyo (JP)

( * ) Notice: Subject to any disclaimer, the term of this patent is extended or adjusted under 35 U.S.C. 154(b) by 498 days.

(21) Appl. No.: 12/934,908

(22) PCT Filed: Mar. 26, 2009

(86) PCT No.: PCT/JP2009/056083
§ 371 (c)(1),
(2), (4) Date: Nov. 24, 2010

(87) PCT Pub. No.: WO2009/119722
PCT Pub. Date: Oct. 1, 2009

(65) Prior Publication Data
US 2011/0065095 A1    Mar. 17, 2011

(30) Foreign Application Priority Data

Mar. 28, 2008    (JP) ................. 2008-088499

(51) Int. Cl.
*C12Q 1/70*    (2006.01)
(52) U.S. Cl.
USPC ....... 435/5; 530/388.3; 530/391.1; 530/391.3
(58) Field of Classification Search
None
See application file for complete search history.

(56) References Cited

U.S. PATENT DOCUMENTS

2009/0311667 A1    12/2009    Takahashi et al.

FOREIGN PATENT DOCUMENTS

| CN | 1814623 | * | 8/2006 | ............. | C07K 16/10 |
|---|---|---|---|---|---|
| CN | 1814623 | A | 8/2006 | | |
| JP | 2007-261988 | A | 10/2007 | | |
| JP | 2007-261988 | * | 11/2007 | ............. | C07K 16/10 |
| JP | 2008-196967 | A | 8/2008 | | |
| WO | WO 2007/021002 | A1 | 2/2007 | | |
| WO | WO 2007/074812 | A1 | 7/2007 | | |
| WO | WO 2008/026741 | A1 | 3/2008 | | |

OTHER PUBLICATIONS

Philpott et al (Journal of Virology 64:2941-2947, 1990, in IDS).*
(Journal of Virology 63:3453-3458, 1989, in IDS).*
Philpott et al (Journal of Virology 63:3453-3458, 1989, in IDS).*
Philpott et al (64:2941-2947, 1990, in IDS).*
Du et al (Biochemical and Biophysical Research Communications 378:197-202, 2009, available online Nov. 14, 2008; in IDS).*
Smirnov et al (Voprosy Virosologii 44:111-5, 1999, abstract only cited).*
Prabkaran et al (PLoS One 4:e4566, Feb. 2009, in IDS).*
Tsuchaya et al (Journal of General Virology 82:2475-2484, 2001).*
Chen et al., "H5 subtype avian flu virus hemagglutinin protien monoclonal antibody, and its preparing method and use", AN 2006-801394, Aug. 9, 2008, XP-002643481.
Extended European Search Report dated Jul. 13, 2011, for Application No. 09726058.2.
Ha et al., "X-ray structures of H5 avian and H9 swine influenza virus hemagglutinins bound to avian and human receptor analogs", PNAS, vol. 98, No. 20, Sep. 25, 2001, pp. 11181-11186.
Liao et al., "Production of monoclonal antibodies specific to H5 hemagglutinin of avian influenza virus and establishment of the H5 antigen capture ELISA", Immunological Journal, vol. 23, No. 3, May 2007, pp. 339-343, XP008138074.
Namba, "Detecting influenza type-A virus subtype H5, involves performing immunoassay using first antibody reacting with respect to all influenza A virus subtypes and second antibody reacting with respect to influenza A virus subtypes H5", AN 2007-545603, Jul. 5, 2007, XP002643506.
Nishimura et al., "Novel anti-hemagglutinin monoclonal antibody and anti-nucleoprotein monoclonal antibody, useful for detecting H5 subtype influenza viruses and other influenza viruses in sample", AN 2007-810126, Oct. 11, 2007, XP002643507.
Philpott et al., "Hemagglutinin Mutations Related to Attenuation and Altered Cell Tropism of a Virulent Avian Influenza A Virus", Journal of Virology, vol. 64, No. 6, Jun. 1990, pp. 2941-2947.
Philpott et al., "Neutralizing Epitopes of the H5 Hemagglutinin from a Virulent Avian Influenza Virus and Their Relationship to Pathogenicity", Journal of Virology, vol. 63, No. 8, Aug. 1989, pp. 3453-3458.

(Continued)

*Primary Examiner* — Mary E Mosher
(74) *Attorney, Agent, or Firm* — Birch, Stewart, Kolasch & Birch, LLP

(57) ABSTRACT

A method of immunoassay of H5 subtype influenza A virus by which the virus can be accurately assayed even in cases where a certain level of mutation has occurred in the H5 subtype influenza A virus, and a kit therefor, and a novel anti-H5 subtype influenza A virus monoclonal antibody which can be used for the immunoassay are disclosed. The antibody or an antigen-binding fragment thereof of the present invention undergoes antigen-antibody reaction with hemagglutinin of H5 subtype influenza A virus, and the corresponding epitope of the antibody or an antigen-binding fragment thereof is located in a region other than the receptor subdomain (excluding C-terminal region thereof consisting of 11 amino acids), which antibody or an antigen-binding fragment thereof does not have neutralizing activity against the influenza A virus.

11 Claims, 5 Drawing Sheets

(56) References Cited

OTHER PUBLICATIONS

Du et al., "Detection of circulating Asian H5N1 viruses by a newly established monoclonal antibody," Biochemical and Biophysical Research Communications, vol. 378, 2009, pp. 197-202.

Ha et al., "H5 avian and H9 swine influenza virus haemagglutinin structures: possible origin of influenza subtypes," The EMBO Journal, vol. 21, No. 5, 2002, pp. 865-875.

He et al., "Detection of H5 Avian Influenza Viruses by Antigen-Capture Enzyme-Linked Immunosorbent Assay Using H5-Specific Monoclonal Antibody," Clinical and Vaccine Immunology, vol. 14, No. 5, May 2007, pp. 617-623.

Kaverin et al., "Epitope Mapping of the Hemagglutinin Molecule of a Highly Pathogenic H5N1 Influenza Virus by Using Monoclonal Antibodies," Journal of Virology, vol. 81, No. 23, Dec. 2007, pp. 12911-12917.

Kaverin et al., "Structure of antigenic sites on the haemagglutinin molecule of H5 avian influenza virus and phenotypic variation of escape mutants," Journal of General Virology, vol. 83, 2002, pp. 2497-2505.

Prabakaran et al., "Development of Epitope-Blocking ELISA for Universal Detection of Antibodies to Human H5N1 Influenza Viruses," PloS ONE, vol. 4, Issue 2, Feb. 2009, pp. 1-10.

Stevens et al., "Structure and Receptor Specificity of the Hemagglutinin from an H5N1 Influenza Virus," Science, vol. 312, Apr. 21, 2006, pp. 404-410.

Tsuda et al., "Development of an Immunochromatographic Kit for Rapid Diagnosis of H5 Avian Influenza Virus Infection," Microbiol. Immunol., vol. 51, No. 9, 2007, pp. 903-907.

Yang et al., "Immunization by Avian H5 Influenza Hemagglutinin Mutants with Altered Receptor Binding Specificity," Science, vol. 317, Aug. 10, 2007, pp. 825-828.

\* cited by examiner

```
AB263192.1    1:MEKIVLLFAIVSLVKSDQICIGYHANNSTEQVDTIMEKNVTVTHAQDILEKTHNGKLCSL 60
Q9DLP3        1:MEKIVLLLAIVSLVKSDQICIGYHANNSTEQVDTIMEKNVTVTHAQDILEKTHNGKLCSL 60
               ****** ****************************************************

AB263192.1   61:NGVKPLILRDCSVAGWLLGNPMCDEFLNVPEWSYIVEKDSPINGLCYPGDFNDYEELKHL 120
Q9DLP3       61:NGVKPLILRDCSVAGWLLGNPMCDEFLNVPEWSYIVEKDNPVNGLCYPGDFNDYEELKHL 120
               *************************************** * ******************

AB263192.1  121:LSSTNHFEKIQIIPRSSWSDHDASSGVSSACPYNGRSSFFRNVVWLIKKNNAYPTIKRNY 180
Q9DLP3      121:LSSTNHFEKIRIIPRSSWSNHDASSGVSSACPYNGRSSFFRNVVWLIKKNNAYPTIKRSY 180
               ********** ******** ************************************** *

AB263192.1  181:NNTNQEDLLVLWGIHHPNDATEQTKLYQNPTTYVSVGTSTLNQRSVPEIATRPKVNGQSG 240
Q9DLP3      181:NNTNQEDLLILWGIHHPNDAAEQTKLYQNPTTYVSVGTSTLNQRSVPEIATRPKVNGQSG 240
               ********* ********** ***************************************

AB263192.1  241:RIEFFWTILKPNDAINFESNGNFIAPEYAYKIAKKGDSAIMKSGLEYGNCNTKCQTPMGA 300
Q9DLP3      241:RMEFFWTILKPNDAINFESNGNFIAPEYAYKIVKKGGSAIMKSGLEYGNCNTKCQTPMGA 300
               * ****************************** *** ***********************

AB263192.1  301:INSSMPFHNIHPLTIGECPRYVKSDRLVLATGLRNVPQRETRGLFGAIAGFIEGGWQGMV 360
Q9DLP3      301:INSSMPFHNIHPLTIGECPKYVKSGRLVLATGLRNVPQRETRGLFGAIAGFIEGGWQGMV 360
               ******************* **** ***********************************

AB263192.1  361:DGWYGYHHSNEQGSGYAADKESTQKAIDGITNKVNSIIDKMNTQFEAVGKEFNNLERRIE 420
Q9DLP3      361:DGWYGYHHSNEQGSGYAADKESTQKAIDGITNKVNSIIDKMNTQFEAVGKEFNNLERRIE 420
               ************************************************************

AB263192.1  421:NLNKKMEDGFLDVWTYNAELLVLMENERTLDFHDSNVKNLYDKVRLQLRDNAKELGNGCF 480
Q9DLP3      421:NLNKKMEDGFLDVWTYNAELLVLMENERTLDFHDSNVKNLYDKVRLQLRDNAKELGNGCF 480
               ************************************************************

AB263192.1  481:EFYHKCDDECMESVRNGTYDYPQYSEEARLNREEISGVKLESIGTYQILSIYSTVASSLA 540
Q9DLP3      481:EFYHKCDNECMESVKNGTYDYPQYSEEARLNREEISGVKLESMGIYQILSIYSTVASSLA 540
               ******* ****** *************************** * ****************

AB263192.1  541:LAIMVAGLSFWMCSNGSLQCRICI                                    564
Q9DLP3      541:LAIMIAGLSFWMCSNGSLQCRICI                                    564
               **** *******************
```

Fig.2

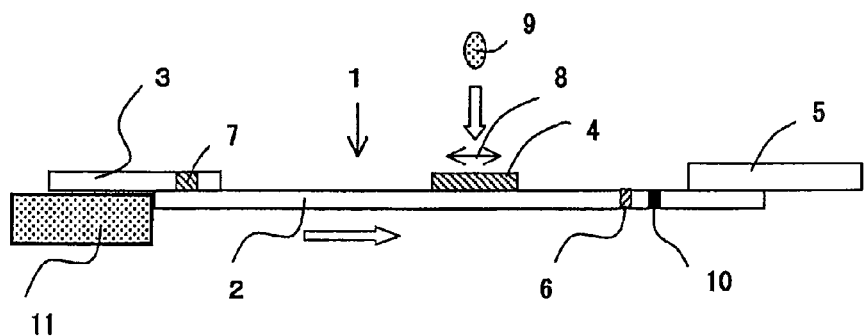
Fig.5
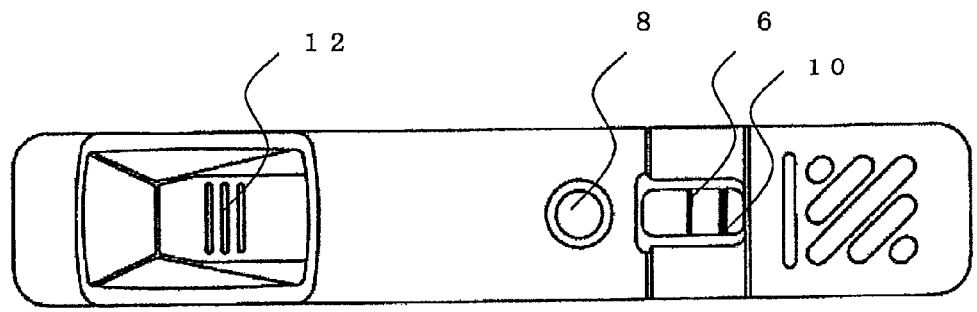
Fig.6
Fig.7

ANTI-(INFLUENZA A VIRUS SUBTYPE H5 HEMAGGLUTININ) MONOCLONAL ANTIBODY

TECHNICAL FIELD

The present invention relates to an anti-H5 subtype influenza A virus hemagglutinin monoclonal antibody, and a method of immunoassay of anti-H5 subtype influenza A virus and an immunoassay kit, which method and kit use the monoclonal antibody.

BACKGROUND ART

Influenza viruses of H5 and H7 types have caused heavy damage to the poultry industry mainly in Asia, and, in recent years, avian influenza virus was confirmed to be infectious also to human. In particular, in terms of avian influenza viruses belonging to H5 subtype, there are many reports as from 2003 on their infection to human and high lethality mainly in Asia, so that there is a worldwide concern of their pandemic due to absence of immunity against the viruses in human. Therefore, prophylaxis of, and countermeasures against them are being studied.

In order to prevent infection of avian influenza virus to human, or in order to prevent at least its outbreak in human, it is important to specifically and rapidly detect avian influenza virus that is infectious also to human. As a method for rapid detection of a virus in a sample, immunoassay has been conventionally widely used, and immunochromatography carried out by a sandwich immunoassay, wherein a solid phase in which an anti-virus antibody is immobilized on a part of a porous substrate through which a liquid is allowed to flow is used, has been especially widely used at clinical sites such as hospitals since viruses can be very simply detected in a short time thereby. Immunochromatography kits with which human influenza viruses can be detected are also commercially available.

In order to detect by immunoassay avian influenza virus that is also infectious to human, an antibody against the avian influenza virus is of course necessary. The surface antigens of influenza viruses are known to contain proteins called hemagglutinin and neuraminidase. As the hemagglutinin (HA), 16 types having different antigenicities, H1 to H16, are known, and, as the neuraminidase, 9 types having different antigenicities, N1 to N9, are known. The subtype of each influenza virus is represented by description of the types of these hemagglutinin and neuraminidase, such as "H5N1". Most of the avian influenza viruses that have been so far confirmed to have been infected from bird to human are those having hemagglutinin of H5 type. Therefore, as an antibody to detect a highly pathogenic influenza virus that is infectious from bird to human, an antibody specific to H5 subtype influenza virus is demanded.

Hemagglutinin of H5 subtype influenza A virus has been studied well, and not only the amino acid sequence but also the spatial structure thereof are known (Non-patent Document 1). Further, various monoclonal antibodies against hemagglutinin of H5 subtype influenza A virus have been known (Non-patent Documents 2 to 4). Further, measurement of H5 subtype influenza A virus by a sandwich immunoassay using 2 types of hemagglutinin monoclonal antibodies has been known (Non-patent Documents 5 and 6).

[Non-patent Document 1] Ya Ha et al; The EMBO Journal, 21(5), 865-875, 2002

[Non-patent Document 2] Nikolai V. K. et al., J. Gen. Virol. 83, 2497, 2002

[Non-patent Document 3] James Stevens et al., SCIENCE VOL 312, 21 Apr. 2006

[Non-patent Document 4] Zhi-Yong Yang et al., SCIENCE VOL 317, 10 Aug. 2007

[Non-patent Document 5] Tsuda Y. et al., Microbiol. Immunol. 51(9), 903, 2007

[Non-patent Document 6] Qigai He et al., Clin. Vacc. Immunol. 617, 2007

DISCLOSURE OF THE INVENTION

Problems to be Solved by the Invention

As monoclonal antibodies against hemagglutinin of H5 subtype influenza A virus, neutralizing antibodies having neutralizing activity as antibodies that suppress and inhibit the infectivity of the virus have been mainly studied so far. In order to develop a vaccine against the virus, a neutralizing antibody is necessary, and the monoclonal antibodies described in the above Non-Patent Documents 2 to 4 are also neutralizing antibodies. Further, in terms of the monoclonal antibodies used for the immunoassays described in Non-patent Documents 5 and 6, there is no description on the result of analysis of the epitopes and neutralizing activity of the antibodies.

Using such a known neutralizing antibody, an immunoassay system for H5 subtype influenza virus can of course be constructed. However, the present inventors noticed that, in cases where an immunoassay system was constructed using a neutralizing antibody, it may be impossible to keep up with mutation of the virus. That is, the present inventors noticed that, since influenza virus is known to cause mutation in the epitope recognized by a neutralizing antibody to escape from immunological surveillance of the host, construction of an immunoassay system using a known neutralizing antibody may lead to loss of reactivity with the mutant virus or decrease in the binding affinity, resulting in inability to detect the virus or drastic decrease in the measured value relative to the correct value. In view of the fact that viruses frequently mutate, it is preferred to be able to accurately carry out immunoassay of a virus even in cases where a certain level of mutation has occurred.

Accordingly, an object of the present invention is to provide a method of immunoassay of H5 subtype influenza A virus by which the virus can be accurately assayed even in cases where a certain level of mutation has occurred in the H5 subtype influenza A virus, and a kit therefor, and a novel anti-H5 subtype influenza A virus monoclonal antibody which can be used for the immunoassay.

Means for Solving the Problems

Influenza virus is known to be first bound to a receptor on the cell surface and then incorporated into the inside of the cell, upon its infection. Therefore, for growth of influenza virus in a host cell, the virus needs to be bound to the receptor on the cell surface, so that, if this process is inhibited, growth of the virus does not occur. The corresponding epitopes of known neutralizing antibodies are located in the receptor binding region of influenza virus, and the neutralizing antibodies are bound to the virus to prevent the virus from being bound to the receptor. On the other hand, viruses are known to be prone to mutation in circumstances where a neutralizing antibody produced by the natural immunity of the host or by administration of a vaccine exists, in order to escape from growth inhibition by the neutralizing antibody. Although the mutation itself may occur at random, only viruses mutated such that their growth is not inhibited by the neutralizing antibody can grow well, so that, as a result, viruses having such a mutation(s) increase among the growing viruses. This phenomenon is called escape mutation, and the fact that a neutralization antibody makes such mutation more easily occur is called antibody pressure or immune pressure. The present inventors inferred that a method of immunoassay by which a virus can be assayed even in cases where a certain level of mutation has occurred in the virus can be constructed by using a monoclonal antibody whose corresponding epitope is located in a region other than the region where the corresponding epitopes of neutralizing antibodies exist, and determined the region where the corresponding epitope of such a monoclonal antibody exists, which monoclonal antibody was then actually provided, thereby completing the present invention.

That is, the present invention provides an anti-H5 subtype influenza A virus hemagglutinin monoclonal antibody or an antigen-binding fragment thereof which undergoes antigen-antibody reaction with hemagglutinin of H5 subtype influenza A virus, whose corresponding epitope does not exist in the receptor subdomain (excluding C-terminal region thereof consisting of 11 amino acids) and which does not have neutralizing activity against the influenza A virus. Further, the present invention provides a method of immunoassay of H5 subtype influenza A virus, comprising measurement of H5 subtype influenza A virus in a sample by immunoassay using antigen-antibody reaction of the above-described monoclonal antibody or an antigen-binding fragment thereof of the present invention with hemagglutinin of the H5 subtype influenza A virus. Further, the present invention provides an immunoassay kit for H5 subtype influenza A virus, comprising 2 types of the above-described monoclonal antibody and/or an antigen-binding fragment thereof of the present invention, the 2 types of the antibody and/or the antigen-binding fragment thereof being capable of binding at the same time to hemagglutinin of H5 subtype influenza A virus.

Effect of the Invention

By the present invention, anti-H5 subtype influenza A virus hemagglutinin monoclonal antibodies whose binding affinities do not change even in cases where H5 subtype influenza A virus caused escape mutation were first provided. Therefore, by immunoassay using a monoclonal antibody of the present invention, it is possible to assay H5 subtype influenza A virus in which escape mutation occurred, and it is also possible to rapidly assay avian influenza virus which is pathogenic also to human. Thus, the present invention is thought to largely contribute to prevention of prevalence of avian influenza virus which is pathogenic also to human.

BRIEF DESCRIPTION OF THE DRAWINGS

FIG. 2 is a diagram showing alignment of the amino acid sequences of hemagglutinin in 2 types of strains of H5 subtype influenza A virus. Accession No. AB263173 in FIG. 2 corresponds to SEQ ID NO: 2. Accession No. Q9DLP3 in FIG. 2 corresponds to SEQ ID NO: 4.

FIG. 5 is a diagram showing results obtained during the epitope analysis of the 3 types of monoclonal antibodies, which was carried out in Examples.

FIG. 6 is a schematic cross-sectional view of the main part of the immunoassay device (immunochromatographic device) prepared in Examples.

FIG. 7 is a schematic plan view of the immunoassay device (immunochromatographic device) prepared in Examples.

BEST MODE FOR CARRYING OUT THE INVENTION

As described above, the monoclonal antibody of the present invention undergoes antigen-antibody reaction with hemagglutinin of H5 subtype influenza A virus, and the corresponding epitope of the monoclonal antibody is located in a region other than the receptor subdomain (excluding C-terminal region thereof consisting of 11 amino acids).

Examples of the base sequence of the gene of hemagglutinin of H5 subtype influenza A virus (this may be hereinafter referred to as "H5 HA" for short) and the amino acid sequence encoded thereby are shown in SEQ ID NOs: 1 and 2. The sequences shown in SEQ ID NOs: 1 and 2 are known and registered in GenBank under the Accession No. AB263192.

Several base sequences of genes and amino acid sequences of H5 HA other than those described above are also known, and examples thereof include the base sequence of the gene and the amino acid sequence of HA of H5N3 described in the above-described Non-patent Document 1, registered in GenBank under Accession No. of AF303057 (the amino acid sequence is registered also under Accession No. Q9DLP3) (SEQ ID NOs. 3 and 4). A monoclonal antibody which undergoes antigen-antibody reaction with one of the known H5 subtype HAs is included within the scope of the monoclonal antibody of the present invention, and, since the homologies among the H5 subtype HAs are high, it usually undergoes antigen-antibody reaction with any of the H5 subtype HAs.

Figure 1:
FIG. 1 is a diagram showing an alignment of the amino acid sequences of hemagglutinin in 2 types of strains of H5 subtype influenza A virus, wherein the distribution of each subdomain and the corresponding epitopes of the 3 types of monoclonal antibodies prepared in Examples are shown. Accession No. AB263173 in FIG. 1 corresponds to SEQ ID NO: 2. Accession No. AF303057 in FIG. 1 corresponds to SEQ ID NO: 4.

An alignment of the amino acid sequence shown in SEQ ID NO:2 and the amino acid sequence shown in SEQ ID NO:4 is shown in FIG. 1. In FIG. 1, each domain in the amino acid sequences is also shown (Non-patent Document 1). FIG. 2 shows only the alignment of the amino acid sequences. Since, as shown well in FIG. 2, the homology between the both amino acid sequences is very high (about 96.8%) and the numbers of amino acids are the same, the distribution of the various domains in the amino acid sequence shown in SEQ ID NO:2 can be easily seen from the distribution of the various domains (Non-patent Document 1) known for SEQ ID NO:4 (FIG. 1). In the present specification and claims, positions in the amino acid sequence of H5 HA are specified based on the amino acid sequence shown in SEQ ID NO:2. Since, as described above, the homologies among the amino acid sequences of HAs of H5 influenza A are very high, the amino acid sequence of another H5 HA can be easily aligned with the amino acid sequence shown in SEQ ID NO:2, so that the corresponding position in the amino acid sequence of the another H5 HA can be easily specified based on the amino acid sequence shown in SEQ ID NO:2. Further, the term "based on the amino acid sequence shown in SEQ ID NO:2" means usage of the amino acid sequence shown in SEQ ID NO:2 as the basis for specifying the position, and does not only mean a monoclonal antibody prepared using HA having the amino acid sequence shown in SEQ ID NO:2 as an immunogen.

As can be seen from FIG. 1, based on the amino acid sequence shown in SEQ ID NO:2, the receptor subdomain corresponds to 278 aa from the 126th amino acid from the N-terminus (hereinafter referred to as "126 aa"). The corresponding epitope of the monoclonal antibody of the present invention does not exist in the receptor subdomain (excluding C-terminal region thereof consisting of 11 amino acids). When the antibody is bound to the receptor subdomain, influenza virus cannot be bound to the receptor on the cell surface, and hence cannot enter the cell, so that the virus cannot grow in the host. That is, the antibody has neutralizing activity against influenza virus. However, it should be noted that a part of the corresponding epitope of one (IFH5-115) of the monoclonal antibodies actually prepared in the Examples below is located in the region of 11 amino acids (268-278 aa) in the C-terminus of the receptor subdomain, but the antibody does not have neutralizing activity, so that the C-terminus region of the receptor subdomain is not indispensable for binding of the virus to the receptor. Therefore, from the region defined in the present invention where the corresponding epitope does not exist (which is basically the receptor subdomain), the 11 amino acids in the C-terminus of the receptor subdomain are excluded.

The corresponding epitope of the monoclonal antibody of the present invention is not restricted as long as it is located in a region other than the above-described receptor subdomain (excluding C-terminal region thereof consisting of 16 amino acids), and the corresponding epitope preferably exists in:

(1) the region of 41 to 60 aa and 312 to 322 aa;
(2) the region of 61 to 80 aa and 290 to 300 aa; or
(3) the region of 101 to 113 aa and 268 to 278 aa.

Figure 3:
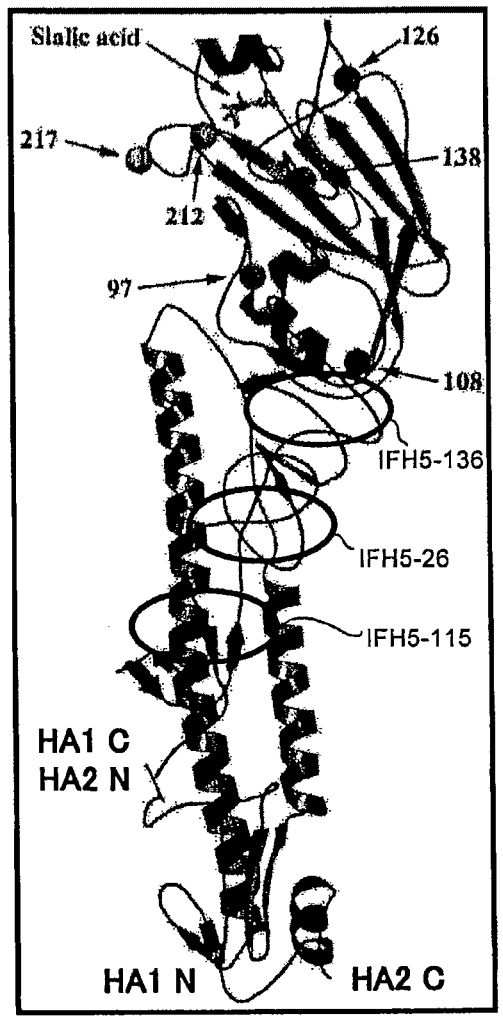
FIG. 3 is a diagram showing the spatial structure of hemagglutinin of the H5 subtype influenza A virus strain, wherein the corresponding epitope regions of the 3 types of monoclonal antibodies prepared in Examples are shown.

Here, the corresponding epitope "exists in the region" means that the binding activity to a deletion mutant in which the region is deleted is lost or at least significantly decreases, and its meaning includes not only cases where the corresponding epitope exists in the region, but also cases where the corresponding epitope exists in a region overlapping with this region and the binding activity is lost or at least significantly decreases if the region is deleted. The corresponding epitope regions defined in each of the above (1) to (3) consist of two regions which are largely distant from each other in the amino acid sequence, but these two regions are adjacent to each other in the spatial structure of HA (see FIG. 3). Therefore, for example, existence of the corresponding epitope in the region of 41 to 60 aa and 290 to 300 aa described in the above (1) means existence of the corresponding region over the entire portion consisting of these regions adjacent to each other in the spatial structure, and in cases where either 36 to 65 aa or 307 to 327 aa is deleted, the monoclonal antibody cannot be bound to the partially deleted HA.

The region in which the corresponding epitope exists can be known by investigation of the binding ability to deletion mutants as concretely described in the Examples below, which investigation is based on a principle used in conventional methods. That is, it can be investigated by preparing various mutants in which various regions are deleted using the genetic engineering technique, followed by assaying whether or not the binding ability to the monoclonal antibody is lost or significantly decreased in each of the deletion mutants due to the deletion.

The monoclonal antibody of the present invention does not have neutralizing activity against the influenza A virus to which it is bound by antigen-antibody reaction. As described above, the corresponding epitope of the monoclonal antibody of the present invention is located in a region other than the receptor subdomain (excluding C-terminus region thereof consisting of 11 amino acids), and by this constitutional requirement, the neutralizing activity is mostly lost, but monoclonal antibodies whose corresponding epitopes are located in regions other than the receptor subdomain (excluding C-terminal region thereof consisting of 11 amino acids) are also included, which monoclonal antibodies exert neutralizing activity by, for example, inhibition of binding of the receptor subdomain to the receptor due to steric hindrance. Whether or not a monoclonal antibody has neutralizing activity can be investigated by allowing a mixture of H5 subtype influenza A virus and the monoclonal antibody to act on cells and culturing the cells, followed by confirming whether or not the cells are injured, as concretely described in the Examples below.

Further, the monoclonal antibody of the present invention is preferably substantially non-cross-reactive with the other HA subtypes (i.e., H1 to H4 and H6 to H15) of influenza A virus. Because of the fact that the monoclonal antibody is substantially non-cross-reactive with the other HA subtypes, H5 subtype influenza A virus which has been confirmed to be infectious from bird to human can be distinguished from other influenza viruses and assayed. Here, the term "substantially non-cross-reactive" means that the cross-reaction does not occur at a detectable level or, even though detection of the cross-reaction is possible, the cross-reaction is very weak and therefore can be clearly distinguished from the antigen-antibody reaction with H5 HA. For example, in the Examples below, cross-reaction with various subtypes of HAs was investigated by immuno chromatography using 2 types of anti-H5 HA monoclonal antibodies of the present invention as an immobilized antibody and a labeled antibody. In such a method, if the label is not detected in the detection zone, the antibodies can be judged to be substantially non-cross-reactive. The base sequences of the genes, as well as the amino acid sequences, of H1 to H4 and H6 to H15 used in the Examples below are shown in SEQ ID NOs:5 to 12 and 15 to 34, respectively. Occurrence of cross-reaction with the other HA subtypes can be investigated using these.

The present invention also provides an antigen-binding fragment of the monoclonal antibody of the present invention. Here, the term "antigen-binding fragment" means an antibody fragment maintaining binding ability (antigen-antibody reactivity) to the corresponding antigen of the antibody, such as a Fab fragment or a F(ab')$_2$ fragment of immunoglobulin. It is well-known that such an antigen-binding fragment can also be used for immunoassay. As is well-known, such fragments can be obtained by treating a monoclonal antibody with a protease such as papain or pepsin. The antigen-binding fragment is not restricted to a Fab fragment and a F(ab')$_2$ fragment, and may be any fragment which maintains binding ability to the corresponding antigen. It may further be one prepared by the genetic engineering technique. Further, for example, a single chain fragment of the variable region (scFv) of an antibody may be expressed in E. coli by the genetic engineering technique and used. The method for preparing scFv is well-known, and scFv can be prepared by a process wherein mRNA of a hybridoma prepared as described above is extracted to prepare single-stranded cDNAs, and PCR is carried out using primers specific to the heavy chain and the light chain of immunoglobulin to amplify the heavy chain gene and the light chain gene, which genes are then linked to each other with a linker and given an appropriate restriction site, followed by introduction of the resultant to a plasmid vector, transformation of E. coli with the resulting plasmid vector, and recovery of scFv from the E. coli. Such scFv is also included in the "antigen-binding fragment" defined in the present invention.

The monoclonal antibody of the present invention can be obtained by a process wherein anti-H5 subtype influenza A virus monoclonal antibodies are prepared by a conventional method using H5 subtype influenza A virus as an immunogen, and monoclonal antibodies having binding ability to HA are screened, followed by screening of those which do not have neutralizing activity against H5 subtype influenza A virus and analysis of the corresponding epitopes of the screened monoclonal antibodies, to select an antibody that satisfies the above-described requirement for the epitope. The monoclonal antibodies themselves can be prepared by the well-known hybridoma method, and the method is also concretely described in the Examples below. Further, the neutralizing activity against influenza A virus can be investigated by the above method wherein a mixture of the virus and a monoclonal antibody is allowed to act on cells to see if the cells are injured, which method is also concretely described in the Examples below. Further, the analysis of the corresponding epitopes can be carried out by the above method wherein various deletion mutants of H5 HA are prepared and their binding ability to each monoclonal antibody is investigated, which method is also concretely described in the Examples below.

The present invention also provides a method of immunoassay of H5 subtype influenza A virus, comprising measurement of H5 subtype influenza A virus in a sample by immunoassay using antigen-antibody reaction of the above-described monoclonal antibody or an antigen-binding fragment thereof of the present invention with hemagglutinin of the H5 subtype influenza A virus. In the present invention, the term "measurement" include detection, quantification and semi-quantification.

Methods of immunoassay themselves are well-known in the art and the monoclonal antibody or an antigen-binding fragment thereof of the present invention can be used in any of the well-known methods of immunoassay. That is, based on the reaction type, known immunoassays include sandwich immunoassays, competition immunoassays, agglutination immunoassays and the like. Based on the label employed, known immunoassays include enzyme immunoassays, radio immunoassays, fluorescence immunoassays, chemiluminescence immunoassays and the like. Any of these immunoassays are included in the "immunoassay" defined in the present invention and can be used as the method of immunoassay of the present invention. The reagents necessary for each type of immunoassay are also well-known in the art. Except for the monoclonal antibody or an antigen-binding fragment thereof used which is characteristic, the immunoassay can be carried out using an ordinary immunoassay kit. That is, the present invention also provides an immunoassay kit for carrying out the method of measurement of the present invention, which kit contains the above-described monoclonal antibody or an antigen-binding fragment thereof of the present invention.

Among the methods of immunoassay, a sandwich immunoassay is advantageous for highly sensitive and rapid measurement of H5 subtype influenza A virus, which immunoassay uses 2 types of the monoclonal antibody and/or an antigen-binding fragment thereof of the present invention which can be bound to hemagglutinin of the virus at the same time. Usually, in a sandwich immunoassay, one of the 2 types of monoclonal antibodies used is immobilized on beads or wells of a microplate, or a solid phase such as a porous matrix for immunochromatography, and the other is labeled by enzyme labeling, fluorescence labeling, chemiluminescence labeling or the like. The virus antigen to be measured is sandwiched between the immobilized antibody and the labeled antibody, and the label bound to the solid phase is measured. In cases where H5 subtype influenza A virus is to be detected, detection of the label bound to the solid phase allows detection of the virus. In cases where the virus is to be quantified, the label is measured for standard samples of various different known amounts by the immunoassay system and the correlation between the amount of the label and the amount of the virus is plotted to prepare a calibration curve (standard curve). By the same operation, the amount of the label of an unknown sample is then measured, and the measured value is applied to the calibration curve to measure the virus quantitatively. These sandwich immunoassays themselves are well-known.

In the sandwich immunoassay of the present invention, 2 types of anti-H5 HA monoclonal antibodies of the present invention which can be bound to a single H5 HA molecule at the same time are used. In this case, the immunoassay is preferably carried out using 2 types out of the 3 types of monoclonal antibodies whose corresponding epitopes exist in:

(1) the region of 41 to 60 aa and 312 to 322 aa;
(2) the region of 61 to 80 aa and 290 to 300 aa; and
(3) the region of 101 to 113 aa and 268 to 278 aa, based on the amino acid sequence shown in SEQ ID NO:2, since, by this, immunoassay which is excellent in the sensitivity and the specificity is possible.

In cases where H5 subtype influenza A virus in a sample is to be quantified, a sandwich immunoassay using wells of a microplate or beads as a solid phase, such as ELISA, can be preferably used. On the other hand, in cases where H5 subtype influenza A virus is to be detected rapidly and simply at clinical sites, immunochromatography (often referred to as "immunochromato" for short) is preferably used. Immunochromatography itself and devices (this may be hereinafter referred to as "immunochromatographic device") used therefor are well-known, and also concretely described in the Examples below.

Briefly, lateral flow-based immunochromatography is carried out using a device having, usually on a belt-like matrix comprising a porous material such as nitrocellulose membrane, a detection zone on which a first anti-H5 HA monoclonal antibody was immobilized, and a labeled reagent zone on which a labeled second anti-H5 HA monoclonal antibody was spotted positioned in the upstream (upstream with respect to the direction of the flow of the later-mentioned developer) of the detection zone. Since the sample is added to the labeled reagent zone, and since it is necessary for the labeled antibody to be discharged from the labeled reagent zone and flow in the matrix, the labeled reagent zone is usually constituted by a porous pad to which the labeled antibody was spotted. At the upstream end of the matrix, a developer tank storing a developer is provided. The device usually further has: a development confirmation section on which an anti-labeled antibody was immobilized, for confirmation of whether or not development of the labeled antibody occurred, in the downstream of the above detection zone; and a developer absorption zone on which a porous absorption pad to absorb the developer flown to this zone is provided, in the further downstream of the development confirmation section. Further, in cases where the label is an enzyme label, a substrate zone on which the substrate of the label enzyme was spotted is provided in the upstream of the labeled reagent zone.

In operation, the sample is added to the labeled reagent zone, and the developer is applied to the upper end of the matrix by breaking the developer tank. The developer flows to the downstream by capillary action of the matrix. When the developer flows through the substrate zone, the substrate is eluted into the developer, and the resulting developer containing the substrate continues to flow. When the developer passes through the labeled reagent zone, the labeled antibody and the sample are eluted into the developer, and the resulting developer containing the substrate, the labeled antibody and the sample continues to flow. In cases where H5 subtype influenza A virus is contained in the sample, HA of the virus is bound to the labeled antibody by antigen-antibody reaction. When the mixture of these has reached the detection zone, the immobilized antibody is bound to HA of the virus by antigen-antibody reaction. As a result, the labeled antibody is immobilized on the detection zone via HA of the virus. Therefore, by measuring the label immobilized on the detection zone, the virus can be detected. In cases where H5 subtype influenza A virus is not contained in the sample, nothing is bound to the immobilized antibody, so that the labeled antibody is not immobilized to the detection zone, and continues to flow to the downstream. Therefore, the label is not detected on the detection zone. Since the anti-labeled antibody is immobilized on the developer confirmation section in the downstream of the detection zone, the labeled antibody is immobilized on the developer confirmation section. In cases where the label is detected on the developer confirmation section, it can be confirmed that the developer has reached this section properly. The developer is absorbed to the absorption pad in the further downstream of the developer confirmation section.

The sample to be applied to the method of immunoassay of the present invention is not restricted as long as whether or not H5 subtype influenza A virus is contained in the sample is to be detected, and examples of the sample include, but are not limited to, body fluids such as blood (including whole blood, plasma and serum), saliva and sputum; mucosal swabs; and swabs of tools and equipments.

The present invention will now be described more concretely by way of Examples. However, the present invention is not restricted to the Examples below.

EXAMPLES

Reference Example 1

Preparation of a H5 Subtype Influenza A Virus (H5N1) Antigen for Immunization and ELISA/Western Blotting (WB)

Chorioallantoic fluid derived from an embryonated egg infected with an attenuated influenza virus strain A/duck/Hokkaido/Vac-1/04(H5N1) (GenBank accession No.: AB259712; SEQ ID NOs:49 and 50) was subjected to ultracentrifugation at 27000 rpm at 4° C. for 1.5 hours, and the virus was recovered as a pellet. The pellet was dissolved into PBS, followed by recovery of the virus-containing fraction by sucrose gradient centrifugation. Ultracentrifugation was carried out again to remove sucrose, thereby obtaining a purified virus solution. The purified virus was inactivated with formalin or Triton X-100 (trademark) to be used as an antigen for immunization and ELISA/WB. The formalin treatment was carried out by adding formalin to the purified virus solution to a final concentration of 0.2% and leaving the resulting mixture to stand at 4° C. for 1 week, and the Triton X-100 (trademark) treatment was carried out by adding 3 volumes of cell extraction buffer (0.05M Tris-HCl (pH8.0), 0.6 M KCl, 0.5% Triton X-100 (trademark)) to the purified virus solution. Inactivation of the virus was confirmed by inoculating the virus subjected to the inactivation treatment to an embryonated egg at 10 days of age and culturing the egg for 2 days, followed by confirming that no HA titer was detected by a hemagglutination (HA) test on chorioallantoic fluid derived from an embryonated egg infected with the virus.

Reference Example 2

Preparation of a H5 Subtype Influenza A Virus (H5N1) Antigen for Confirmation of Specificity (IF, WB)

The virus-infected Madin-Darby canine kidney (MDCK) cells (source of supply: Hokkaido University) to be used for confirmation of the specificity of the established antibody, and cell extract thereof were prepared as follows. For preparation of the antibody for immunofluorescence (IF), MDCK cells were cultured on a chamber slide to obtain a full sheet of the cells, and each influenza virus was optimally diluted with MEM supplemented with trypsin (serum-free) and inoculated to the cells. The cells were then cultured in a $CO_2$ incubator at 35° C. for 16 hours, and the cultured cells were fixed with cold acetone to provide a slide for IF for confirmation of the specificity.

For preparation of the antigen for WB, MCDK cells were cultured in a petri dish to obtain a full sheet of the cells, and serum-free MEM supplemented with trypsin was added to a virus solution optimized in the same manner as in the preparation of the antibody for IF, followed by culturing the cells at 35° C. for 16 hours. Thereafter, cell lysis buffer was added to the petri dish to lyse the cells, and the resulting lysate was centrifuged at 14000 rpm for 5 minutes, to obtain the supernatant as the antigen for WB for confirmation of the specificity.

Example 1

Establishment of Monoclonal Antibodies Specific to Influenza A Virus (H5) Hemagglutinin The monoclonal antibodies were prepared by immunizing mice with the purified inactivated influenza virus A/duck/Hokkaido/Vac-1/04(H5N1) prepared in Reference Example 1, followed by fusing lymphocytes derived from hind limbs of the mice and myeloma cells. That is, BALB/C mice were first immunized in their footpads with the purified inactivated influenza virus A/duck/Hokkaido/Vac-1/04(H5N1) emulsified with Freund's complete adjuvant in an amount of 50 to 100 μg/mouse, and 2 to 3 weeks later, the mice were subjected to second immunization with the purified inactivated influenza virus A/duck/Hokkaido/Vac-1/04(H5N1) antigen which is adjuvant-free in an amount of 50 to 100 μg/mouse. The antibody titer was confirmed by solid-phase ELISA using a 96-well ELISA plate coated with Triton X100-treated purified influenza virus A/duck/Hokkaido/Vac-1/04(H5N1), and by WB with the same antigen. Mice in which increase in the antibody titer was confirmed were immunized in their footpads with the purified inactivated influenza virus A/duck/Hokkaido/Vac-1/04(H5N1) in an amount of 25 to 50 µg/mouse, and 3 to 4 days later, lymphocytes were prepared from lymph nodes of hinder limbs of the mice. Mouse myeloma cells (P3U1) preliminarily cultured in RPMI-1640 medium were mixed with spleen cells at ratios of 1:2 to 1:5, and cell fusion was carried out using polyethylene glycol (PEG; manufactured by Boehringer). The fused cells were suspended in HAT medium and aliquoted to a 96-well culture plate, followed by culturing the cells in a $CO_2$ incubator at 37° C.

Screening of the produced antibodies was carried out by the above-described solid-phase ELISA. That is, the Triton X-100 (trademark)-treated purified influenza virus A/duck/Hokkaido/Vac-1/04(H5N1) antigen was aliquoted to a 96-well ELISA plate (manufactured by Nunc) at a concentration of 1 µg/ml in a volume of 50 µl/well, and left to stand at 4° C. overnight to allow its adsorption. The wells were blocked with 1% skim milk and washed 3 times with washing buffer (PBS supplemented with 0.05% Tween 20), followed by adding 50 µl of the culture supernatant from the plate in which the cell fusion was carried out, and allowing the reaction to proceed at 37° C. for 1 hour. After washing the wells 3 times with washing buffer in the same manner, a POD-labeled anti-mouse immunoglobulin antibody (manufactured by DACO) was added, followed by allowing the reaction to proceed at 37° C. for 1 hour. After washing the wells 4 times with washing buffer, the substrate ABTS was added, followed by selecting the wells in which coloring was observed. Subsequently, the cells in the selected wells were transferred to a 48-well or 24-well culture plate and cultured in a CO2 incubator at 37° C., followed by confirming their reactivity with hemagglutinin by WB. The WB was carried out according to a conventional method using a membrane prepared by subjecting the Triton X-100 (trademark)-treated purified influenza virus A/duck/Hokkaido/Vac-1/04(H5N1) antigen to SDS-PAGE, followed by transferring it to a nitrocellulose membrane. The cells in the wells in which reactivity to hemagglutinin was confirmed by WB were made into single clones by the limiting dilution method to establish the various hybridomas described below which produce monoclonal antibodies reactive with influenza (H5N1) hemagglutinin.

In order to exclude clones having cross-reactivity with epitopes, competing monoclonal antibodies were first excluded by an inhibition test, and only monoclonal antibodies that are not competitive with one another were selected. More particularly, this inhibition test was carried out as follows. A 96-well ELISA plate to which purified influenza virus was adsorbed was prepared in the same manner as in the screening of the Mabs, and a Mab for inhibition at a several-fold higher concentration and an equal amount of an alkaline phosphatase-labeled Mab were added to each well at the same time, followed by allowing the reaction to proceed at 37° C. for 1 hour. After washing, the substrate pNPP was added, and whether the reaction of the labeled Mab with the solid phase was inhibited by each Mab was confirmed. Selected 14 types of monoclonal antibodies were used in various combinations as the solid phase antibody and the labeled antibody for the later-mentioned immunochromatographic device which was actually prepared by the late-mentioned method. Using the prepared immunochromatographic device, influenza A virus in a sample was actually detected, and 3 types of monoclonal antibodies IFH5-115, IFH5-136 and IFH5-26 showing excellent sensitivities and specificities (absence of cross-reaction with other HA subtypes, as mentioned later), and 3 types of hybridomas IFH5-115, IFH5-136 and IFH5-26 producing them were established (the monoclonal antibodies IFH5-115, IFH5-136 and IFH5-26 may be hereinafter referred to as the monoclonal antibody 115 (or Mab 115), monoclonal antibody 136 (or Mab 136) and monoclonal antibody 26 (or Mab 26), respectively). These monoclonal antibodies did not have neutralizing activity against influenza A virus, as mentioned later.

Example 2

Confirmation of the Reaction Specificities of the Monoclonal Antibodies by IF and WB The IF was carried out as follows. That is, to the slide for IF for confirmation of the specificity which was prepared in Reference Example 2, the culture supernatant for each monoclonal antibody or ascites (diluted with 1% BSA in PBST) was added, and the reaction was allowed to proceed for 1 hour at room temperature. The resultant was washed with PBS and allowed to react with a fluorescent dye-labeled anti-mouse IgG (1000-fold diluted with 1% BSA in PBST) at room temperature for 30 minutes. This was followed by washing with PBS, mounting in glycerol and observation under a fluorescence microscope. WB was carried out using the antigen prepared in Reference Example 2 according to a conventional method.

The monoclonal antibodies IFH5-115, IFH5-136 and IFH5-26 were confirmed in either assay to be reactive with attenuated H5N1 influenza HA, but the results on the reactivities against HAs of other substrains and virulent H5N1 were different between the assays. Therefore, the actual assay system (EL) was used for confirmation of these.

Example 3

Analysis of the Corresponding Epitopes of the Anti-Influenza H5N1 Virus Monoclonal Antibodies 3-1: Preparation of N-Terminus Deletion Plasmids In order to determine the recognition sites of Mab 26, 115 and 136 in the N-terminus side, HA of the influenza H5N1 strain A/duck/Hokkaido/Vac-1/04(H5N1) (SEQ ID NO:2) consisting of 564 amino acids was subjected to PCR to amplify 6 types of fragments: 1 to 564 aa (A fragment), 1 to 514 aa (B fragment), 21 to 514 aa (C fragment), 101 to 500 aa (D fragment), 151 to 500 aa (E fragment), and 201 to 500 aa (F fragment). A BamHI or XbaI site had been preliminarily added to each primer. Each amplified fragment was purified with PCR Purification Kit manufactured by QIAGEN and inserted into the BamHI-XbaI site in an expression plasmid pWG6A which was prepared by incorporating GST into the NdeI-EcoRI site in an expression plasmid pW6A, to prepare the plasmids pWGInf.H5N1-N-A, pWGInf.H5N1-N-B, pWGInf.H5N1-N-C, pWGInf.H5N1-N-D, pWGInf.H5N1-N-E and pWGInf.H5N1-N-F. Using these plasmids, *E. coli* BL21(DE3) (supplied from Brookhaven National Laboratory) was transformed to obtain ampicillin-resistant *E. coli* transformants BL21(DE3)pWGInf.H5N1-N-A, BL21(DE3)pWGInf.H5N1-N-B, BL21(DE3)pWGInf.H5N1-N-C, BL21(DE3)pWGInf.H5N1-N-D, BL21(DE3)pWGInf.H5N1-N-E and BL21(DE3)pWGInf.H5N1-N-F.

3-2 Expression and Western Blotting of Recombinant Proteins (GST+Inf.H5N1-N-A, GST+Inf.H5N1-N-B, GST+Inf.H5N1-N-C, GST+Inf.H5N1-N-D, GST+Inf.H5N1-N-E and GST+Inf.H5N1-N-F)

Each of the transformants prepared in 3-1 was cultured in 2 ml of LB medium supplemented with 50 µg/ml ampicillin at 37° C. Preculture was carried out until an OD of 0.6 to 0.8 at 600 nm was attained, and 1 mM IPTG was then added to the culture to induce expression, followed by culturing for additional 3 hours. The bacterial cells were collected by centrifuging 1.5 ml of the bacterial cell culture at 5,000 rpm for 2 minutes, and the collected bacterial cells were suspended in 100 μl of a buffer (10 mM Tris-HCl (pH 8.0), 0.1 M sodium chloride, 1 mM EDTA), followed by completely disrupting the bacterial cells by sonication for 15 minutes. The resultant was used as a bacterial cell sample.

Figure 4:
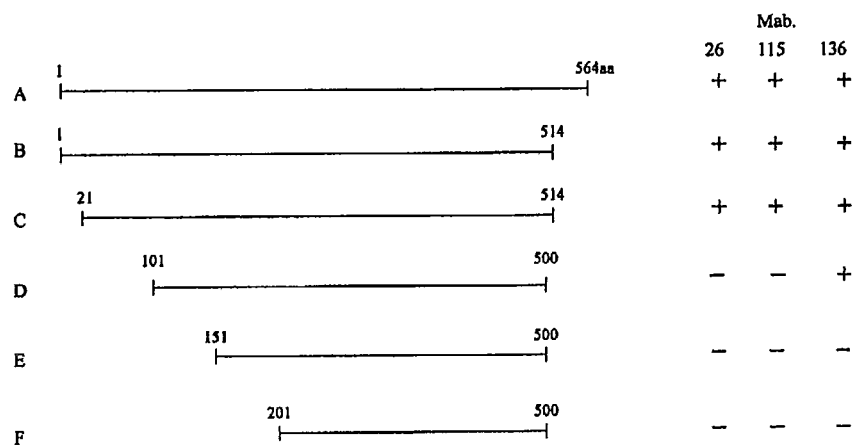
FIG. 4 is a diagram showing the results obtained during the epitope analysis of the 3 types of monoclonal antibodies, which was carried out in Examples.

To 8 μl of the bacterial sample, 4 μl of 3×SDS polyacrylamide buffer (0.15 M Tris-HCl (pH 6.8), 6% SDS, 24% glycerol, 6 mM EDTA, 2% 2-mercaptoethanol, 0.03% bromophenol blue) was added, and the resulting mixture was stirred sufficiently, followed by heat treatment at 100° C. before being subjected to electrophoresis. Sodium dodecyl sulfate-polyacrylamide gel electrophoresis (SDS-PAGE) was carried according to a conventional method using e-PAGEL, 12.5% gel concentration (trademark; manufactured by ATTO). Thereafter, the sample was transferred to a PVDF membrane (manufactured by ATTO) and blocked with 1% BSA at 4° C. overnight. The blocking solution was removed, and the membrane was washed with PBS-Tween (trademark), followed by adding the monoclonal antibodies 26, 115 and 136 whose concentrations were adjusted to 2 μg/ml and allowing the reaction to proceed at room temperature for 60 minutes. The membrane was washed sufficiently with PBS-Tween (trademark) and subjected to a reaction with a peroxidase-labeled anti-mouse immunoglobulin rabbit polyclonal antibody (manufactured by DAKO) 5000-fold diluted with a reaction buffer. After washing, the membrane was exposed to instant film (manufactured by FUJIFILM) for 1 to 15 minutes using ECL Western Blotting Detection System (manufactured by GE Healthcare Bio-Sciences KK) to detect signals. The results are shown in FIG. 4. The monoclonal antibodies 26 and 115 reacted with the A, B and C fragments, but not reacted with the D fragment. The monoclonal antibody 136 reacted with the A, B, C and D fragments, but not reacted with the E fragment. Accordingly, the monoclonal antibodies 26 and 115, and the monoclonal antibody 136 were revealed to recognize the region of 21 to 100 aa and the region of 101 to 150 aa, respectively.

3-3: Preparation of N-terminus Deletion Plasmids

Subsequently, shorter fragments of the amino acid fragment of 21 to 400 of influenza H5N1: N1 (21 to 400 aa), N2 (41 to 400 aa), N3 (61 to 400 aa), N4 (81 to 400 aa), N5 (101 to 400 aa), N6 (114 to 400 aa), N7 (127 to 400 aa) and N8 (139 to 400 aa) were amplified by PCR. Each amplified fragment was purified with PCR Purification Kit manufactured by QIAGEN and inserted into the BamHI-XbaI site in an insect cell expression plasmid pBac-EGTs-6A (manufactured by Invitrogen; modified from pFastBac1 vector), to prepare plasmids pBacInf.H5N1-N1, pBacInf.H5N1-N2, pBacInf.H5N1-N3, pBacInf.H5N1-N4, pBacInf.H5N1-N5, pBacInf.H5N1-N6, pBacInf.H5N1-N7 and pBacInf.H5N1-N8. Using these plasmids, E. coli DH10Bac for Bacmid preparation was transformed, to prepare Bacmid-Inf.H5N1-N1, Bacmid-Inf.H5N1-N2, Bacmid-Inf.H5N1-N3, Bacmid-Inf.H5N1-N4, Bacmid-Inf.H5N1-N5, Bacmid-Inf.H5N1-N6, Bacmid-Inf.H5N1-N7 and Bacmid-Inf.H5N1-N8.

3-4 Expression of Recombinant Proteins (Inf.H5N1-N1, Inf.H5N1-N2, Inf.H5N1-N3, Inf.H5N1-N4, Inf.H5N1-N5, Inf.H5N1-N6, Inf.H5N1-N7 and Inf.H5N1-N8)

Transfection of insect cells, Sf-21 (manufactured by Invitrogen), with each of the 8 types of Bacmid DNAs prepared in 3-3 was carried out to prepare recombinant viruses P1-N1, P1-N2, P1-N3, P1-N4, P1-N5, P1-N6, P1-N7 and P1-N8. Sf21 cells were infected with a part of each of these P1s and cultured at 27° C. for 4 days, followed by collecting the culture supernatant by centrifugation at 3000 rpm for 20 minutes. This was used as the sample for ELISA.

The monoclonal antibody 254 which reacts with the amino acid region of 139 to 400 was immobilized and used for ELISA. That is, the monoclonal antibody 254 was diluted to a concentration of 2 μg/mL, and 50 μl of the diluted monoclonal antibody was placed in each well of a microplate module (manufactured by Nunc), followed by incubation at 4° C. overnight to immobilize the monoclonal antibody. Subsequently, each well was washed with PBS supplemented with 0.1% Tween 20 (trademark) (PBS-Tween (trademark)), and 100 μL of 1% bovine serum albumin (BSA) prepared by dilution with PBS was added to the well, followed by blocking at 37° C. for 1 hour. After removing the blocking solution, 50 μl of a biotinylated monoclonal antibody 26, 115 or 126 was added, and the reaction was allowed to proceed at 37° C. for 1 hour. After washing sufficiently with PBS-Tween (trademark), 50 μL of alkaline phosphatase-labeled streptavidin (manufactured by DAKO) 2,000-fold diluted with a reaction buffer was added to each well, and the reaction was allowed to proceed at 37° C. for 1 hour. Thereafter, the wells were washed sufficiently with PBS-Tween (trademark), and 50 μl of p-nitrophenyl phosphate was added to each well. The reaction was allowed to proceed at room temperature for 30 minutes, and 50 μl of a stop solution was added to each well, followed by measuring the coloring level (absorbance) at a wave length of 405 nm. As shown in Table 1, it can be assumed that the monoclonal antibody 26 has its epitope in the region of amino acids 61 to 80; the monoclonal antibody 115 has its epitope in the region of amino acids 41 to 60; and the monoclonal antibody 136 has its epitope in the region of amino acids 101 to 113.

TABLE 1

| | 26 | | 115 | | 136 | |
|---|---|---|---|---|---|---|
| 21-400 | 1.98 | 1.89 | 0.68 | 0.67 | 1.48 | 1.39 |
| 41-100 | 1.94 | 1.88 | 0.84 | 0.64 | 1.54 | 1.50 |
| 61-400 | 1.92 | 1.93 | 0.29 | 0.28 | 1.21 | 1.20 |
| 81-400 | 0.15 | 0.15 | 0.30 | 0.27 | 0.78 | 0.74 |
| 101-400 | 0.15 | 0.16 | 0.28 | 0.27 | 0.57 | 0.50 |
| 114-400 | 0.16 | 0.16 | 0.30 | 0.29 | 0.16 | 0.17 |
| 127-400 | 0.16 | 0.16 | 0.28 | 0.29 | 0.17 | 0.17 |
| 139-400 | 0.15 | 0.15 | 0.28 | 0.29 | 0.16 | 0.16 |
| 1-514 | 1.00 | 0.70 | 1.10 | 0.87 | 1.38 | 1.44 |
| HBs wt | 0.14 | 0.13 | 0.24 | 0.26 | 0.14 | 0.14 |
| control | 0.13 | 0.13 | 0.26 | 0.26 | 0.14 | 0.15 |

3-5 Preparation of C-Terminus Deletion Plasmids

In order to determine the recognition sites of Mab 26, 115 and 136 in the C-terminus side, HA of the influenza H5N1 strain A/duck/Hokkaido/Vac-1/04(H5N1) (SEQ ID NO:2) consisting of 564 amino acids was subjected to PCR to amplify 5 types of fragments: 21 to 400 aa (A fragment), 21 to 333 aa (B fragment), 21 to 266 aa (C fragment), 21 to 200 aa (D fragment), and 21 to 133 aa (E fragment). A BamHI or XbaI site had been preliminarily added to each primer. Each amplified fragment was purified with PCR Purification Kit manufactured by QIAGEN and inserted into the BamHI-XbaI site in an expression plasmid pWG6A which was prepared by incorporating GST into the NdeI-EcoRI site in an expression plasmid pW6A, to prepare the plasmids pWGInf.H5N1-C-A, pWGInf.H5N1-C-B, pWGInf.H5N1-C-C, pWGInf.H5N1-C-D and pWGInf.H5N1-C-E. Using these, E. coli BL21 (DE3) (supplied from Brookhaven National Laboratory) was transformed to obtain ampicillin-resistant E. coli transformants BL21(DE3)pWGInf.H5N1-C-A, BL21(DE3)

pWGInf.H5N1-C-B, BL21(DE3)pWGInf.H5N1-C-C, BL21 (DE3)pWGInf.H5N1-C-D and BL21(DE3)pWGInf.H5N1-C-E.

3-6 Expression and Western Blotting of Recombinant Proteins (GST+Inf.H5N1-C-A, GST+Inf.H5N1-C-B, GST+ Inf.H5N1-C-C, GST+Inf.H5N1-C-D and GST+Inf.H5N1-C-E)

Each of the transformants prepared in 3-5 was cultured in 2 ml of LB medium supplemented with 50 μg/ml ampicillin at 37° C. Preculture was carried out until an OD of 0.6 to 0.8 at 600 nm was attained, and 1 mM IPTG was then added to the culture to induce expression, followed by culturing for additional 3 hours. The bacterial cells were collected by centrifuging 1.5 ml of the bacterial cell culture at 5,000 rpm for 2 minutes, and the collected bacterial cells were suspended in 100 μl of a buffer (10 mM Tris-HCl (pH 8.0), 0.1 M sodium chloride, 1 mM EDTA), followed by completely disrupting the bacterial cells by sonication for 15 minutes. The resultant was used as a bacterial cell sample.

To 8 μl of the bacterial sample, 4 μl of 3×SDS polyacrylamide buffer (0.15 M Tris-HCl (pH 6.8), 6% SDS, 24% glycerol, 6 mM EDTA, 2% 2-mercaptoethanol, 0.03% bromophenol blue) was added, and the resulting mixture was stirred sufficiently, followed by heat treatment at 100° C. before being subjected to electrophoresis. Sodium dodecyl sulfate-polyacrylamide gel electrophoresis (SDS-PAGE) was carried according to a conventional method using e-PAGEL, 12.5% gel concentration (trademark; manufactured by ATTO). Thereafter, the sample was transferred to a PVDF membrane (manufactured by ATTO) and blocked with 1% BSA at 4° C. overnight. The blocking solution was removed, and the membrane was washed with PBS-Tween (trademark), followed by adding the monoclonal antibodies 26, 115 and 136 whose concentrations were adjusted to 2 μg/ml and allowing the reaction to proceed at room temperature for 60 minutes. The membrane was washed sufficiently with PBS-Tween (trademark) and subjected to a reaction with a peroxidase-labeled anti-mouse immunoglobulin rabbit polyclonal antibody (manufactured by DAKO) 5000-fold diluted with a reaction buffer. After washing, the membrane was exposed to instant film (manufactured by FUJIFILM) for 1 to 15 minutes using ECL Western Blotting Detection System (manufactured by GE Healthcare Bio-Sciences KK) to detect signals. The results are shown in FIG. 5. The monoclonal antibodies 26, 115 and 136 reacted with the A and B fragments, but not reacted with the C fragment. Accordingly, the monoclonal antibodies 26, 115 and 136 were revealed to recognize the region of 267 to 333aa.

3-7: Preparation of C-Terminus Deletion Plasmids

Subsequently, shorter fragments of the amino acid fragment of 267 to 333 aa of influenza H5N1: C1 (41 to 333 aa), C2 (41 to 322 aa), C3 (41 to 311 aa), C4 (41 to 300 aa), C5 (41 to 289 aa), C6 (41 to 278 aa) and C7 (41 to 267 aa) were amplified by PCR. Each amplified fragment was purified with PCR Purification Kit manufactured by QIAGEN and inserted into the BamHI-XbaI site in an insect cell expression plasmid pBac-EGTs-6A (manufactured by Invitrogen; modified from pFastBac1 vector), to prepare plasmids pBacInf.H5N1-C1, pBacInf.H5N1-C2, pBacInf.H5N1-C3, pBacInf.H5N1-C4, pBacInf.H5N1-05, pBacInf.H5N1-C6 and pBacInf.H5N1-C7. Using these plasmids, E. coli DH10Bac for Bacmid preparation was transformed, to prepare Bacmid-Inf.H5N1-C1, Bacmid-Inf.H5N1-C2, Bacmid-Inf.H5N1-C3, Bacmid-Inf.H5N1-C4, Bacmid-Inf.H5N1-05, Bacmid-Inf.H5N1-C6 and Bacmid-Inf.H5N1-C7

3-8 Expression of Recombinant Proteins (Inf.H5N1-C1, Inf.H5N1-C2, Inf.H5N1-C3, Inf.H5N1-C4, Inf.H5N1-05, Inf.H5N1-C6 and Inf.H5N1-C7)

Transfection of insect cells, Sf-21 (manufactured by Invitrogen) with each of the 7 types of Bacmid DNAs prepared in 3-7 was carried out to prepare recombinant viruses P1-C1, P1-C2, P1-C3, P1-C4, P1-C5, P1-C6 and P1-C7. S121 cells were infected with a part of each of these P1s and cultured at 27° C. for 4 days, followed by collecting the culture supernatant by centrifugation at 3000 rpm for 20 minutes. This was used as the sample for Enzyme Linked Immunosorbent Assay (ELISA).

The monoclonal antibody 270 which reacts with the amino acid region of 41 to 333 aa was immobilized and used for ELISA. That is, the monoclonal antibody 270 was diluted to a concentration of 2 μg/mL, and 50 μl of the diluted monoclonal antibody was placed in each well of a microplate module (manufactured by Nunc), followed by incubation at 4° C. overnight to immobilize the monoclonal antibody. Subsequently, each well was washed with PBS supplemented with 0.1% Tween 20 (trademark) (PBS-Tween (trademark)), and 100 μL of 1% bovine serum albumin (BSA) prepared by dilution with PBS was added to the well, followed by blocking at 37° C. for 1 hour. After removing the blocking solution, 50 μl of a biotinylated monoclonal antibody 26, 115 or 126 was added, and the reaction was allowed to proceed at 37° C. for 1 hour. After washing sufficiently with PBS-Tween (trademark), 50 μL of alkaline phosphatase-labeled streptavidin (manufactured by DAKO) 2,000-fold diluted with a reaction buffer was added to each well, and the reaction was allowed to proceed at 37° C. for 1 hour. Thereafter, the wells were washed sufficiently with PBS-Tween (trademark), and 50 μl of p-nitrophenyl phosphate was added to each well. The reaction was allowed to proceed at room temperature for 30 minutes, and 50 μl of a stop solution was added to each well, followed by measuring the coloring level (absorbance) at a wave length of 405 nm. As shown in Table 2, it can be assumed that the monoclonal antibody 26 has its epitope in the region of amino acids 290 to 300; the monoclonal antibody 115 has its epitope in the region of amino acids 312 to 322; and the monoclonal antibody 136 has its epitope in the region of amino acids 268 to 278.

TABLE 2

| Mutant | 26 | | 115 | | 136 | |
|---|---|---|---|---|---|---|
| 41-333 | 0.22 | 0.23 | 0.94 | 0.96 | 0.95 | 0.96 |
| 41-322 | 0.55 | 0.52 | 0.87 | 0.78 | 1.10 | 1.12 |
| 41-311 | 0.53 | 0.50 | 0.15 | 0.14 | 1.15 | 1.18 |
| 41-300 | 0.57 | 0.61 | 0.14 | 0.14 | 1.13 | 1.21 |
| 41-289 | 0.17 | 0.17 | 0.15 | 0.14 | 1.01 | 1.07 |
| 41-278 | 0.17 | 0.16 | 0.13 | 0.14 | 0.99 | 1.01 |
| 41-267 | 0.14 | 0.13 | 0.14 | 0.14 | 0.19 | 0.15 |
| 1-514 | 1.60 | 1.47 | 1.55 | 1.34 | 1.10 | 1.11 |
| HBs wt | 0.13 | 0.13 | 0.17 | 0.13 | 0.12 | 0.14 |
| Sf21 | 0.13 | 0.13 | 0.13 | 0.15 | 0.09 | 0.16 |

In summary, from 3-1 to 3-8, it is assumed that the monoclonal antibody 26 recognizes the regions of 61 to 88 aa and 290 to 300 aa; the monoclonal antibody 115 recognizes the regions of 41 to 60 aa and 312 to 322 aa; and the monoclonal antibody 136 recognizes the regions of 101 to 113 aa and 268 to 278 aa. That is, it is assumed that these monoclonal antibodies recognize the spatial structure (see FIG. 3).

Example 4

Assay of Neutralizing Antibody Activity

Whether or not the monoclonal antibodies IFH5-115, IFH5-136 and IFH5-26 have neutralizing activity against H5 subtype influenza A viruses was tested. As the influenza viruses, A/dk/Hokkaido/84/02(H5N3) and A/PR/8/34 (H1N1) were used. A 2-fold dilution series of each monoclonal antibody was prepared with Eagle's MEM, and 50 µl of each antibody dilution was placed in a 96-well plate. Each of the A/dk/Hokkaido/84/02(H5N3) and A/PR/8/34(H1N1) was diluted such that 200 $TCID_{50}/25$ µL was attained, and 25 µl of the virus dilution was added to each well containing the antibody dilution (protein concentration: 0 to 160 µg/25 µL). The resulting mixture was incubated at room temperature for 1 hour (virus-antibody mixture). On the other hand, in a 48-well plate, MDCK cells were preliminarily cultured in Eagle's MEM supplemented with 10% fetal calf serum to confluence, and the culture supernatant was removed. The plate was washed once with Eagle's MEM, and 75 µl of the above-described virus-antibody mixture was added thereto, followed by incubation at 35° C. for 1 hour. Subsequently, 150 µl of Eagle's MEM supplemented with 0.0005% trypsin was added to each well, and culture was started at 35° C. in the presence of 5% carbon dioxide gas. On day 3 of the culture, whether or not cell injury by the virus was inhibited by neutralizing antibody activity was investigated under the microscope to confirm whether or not the neutralizing activity was exerted. In cases where cell injury has occurred, cell rounding due to cell fusion by virus infection is observed. In cases where cell injury has not occurred, it can be judged that the monoclonal antibody has neutralizing activity against the virus.

In terms of controls for this measurement system, a well to which no antibody was added was used as the virus activity control, and chicken antiserum of A/duck/Hokkaido/Vac-1/04 (SEQ ID NO:2) having neutralizing activity was used as the neutralizing antibody control. The test results are shown in Table 3 to Table 6.

The chicken antiserum (obtained by immunization with A/duck/Hokkaido/Vac-1/04 (SEQ ID NO:2)) used as the neutralizing antibody control showed neutralizing antibody activity against A/dk/Hokkaido/84/02(H5N3) and A/PR/8/34 (H1N1) up to 64-fold dilution, but the monoclonal antibodies IFH5-115, IFH5-136 and IFH5-26 showed no neutralizing activity.

TABLE 3

Virus: A/dk/Hokkaido/84/02(H5N3) $10^2$ TCID50/25 µL(well)

| Antibody | Antibody concentration (µg/mL) | | | | | | CPE |
|---|---|---|---|---|---|---|---|
| | 160 | 80 | 40 | 20 | 10 | 0 | |
| IFH5-115 | + | + | + | + | + | + | |
| | + | + | + | + | + | + | |
| | + | + | + | + | + | + | |
| | + | + | + | + | + | + | |
| IFH5-136 | + | + | + | + | + | + | |
| | + | + | + | + | + | + | |
| | + | + | + | + | + | + | |
| | + | + | + | + | + | + | |
| IFH5-26 | + | + | + | + | + | + | |
| | + | + | + | + | + | + | |
| | + | + | + | + | + | + | |
| | + | + | + | + | + | + | |

TABLE 4

Virus: A/PR/8/34(H1N1) $10^2$ TCID50/25 µL(well)

| Antibody | Antibody concentration (µg/mL) | | | | | | CPE |
|---|---|---|---|---|---|---|---|
| | 160 | 80 | 40 | 20 | 10 | 0 | |
| IFH5-115 | + | + | + | + | + | + | |
| | + | + | + | + | + | + | |
| | + | + | + | + | + | + | |
| | + | + | + | + | + | + | |
| IFH5-136 | + | + | + | + | + | + | |
| | + | + | + | + | + | + | |
| | + | + | + | + | + | + | |
| | + | + | + | + | + | + | |
| IFH5-26 | + | + | + | + | + | + | |
| | + | + | + | + | + | + | |
| | + | + | + | + | + | + | |
| | + | + | + | + | + | + | |

TABLE 5

| Immune serum | Chicken immune serum dilution rate | | | | | | | | CPE |
|---|---|---|---|---|---|---|---|---|---|
| | 2 | 4 | 6 | 8 | 16 | 32 | 64 | 128 | 256 |
| A/duck/Hokkaido/V ac-1/04 (H5N1) chicken immune serum | − | − | − | − | − | − | − | + | + |
| | − | − | − | − | − | − | − | + | + |
| | − | − | − | − | − | − | − | + | + |
| | − | − | − | − | − | − | − | + | + |

TABLE 6

| Immune serum | Chicken immune serum dilution rate | | | | | | | | CPE |
|---|---|---|---|---|---|---|---|---|---|
| | 2 | 4 | 6 | 8 | 16 | 32 | 64 | 128 | 256 |
| A/duck/Hokkaido/V ac-1/04 (H5N1) chicken immune serum | − | − | − | − | − | − | − | + | + |
| | − | − | − | − | − | − | − | + | + |
| | − | − | − | − | − | − | − | + | + |
| | − | − | − | − | − | − | − | + | + |

Example 5

Preparation of the Influenza A H5 Immunoassay (Immunochromatography) Device 1

As shown in FIG. 6, at the position 15 mm distant from the end of the developer-absorption zone 5-side of a matrix 2 which is a nitrocellulose membrane having a width of 5 mm and a length of 50 mm (manufactured by Millipore), 0.7 of an aqueous solution containing an anti-influenza A H5-specific antibody (IFH5-26) was spotted, and the spot was dried, thereby preparing a detection zone 6. Further, at the position 12 mm distant from the end of the developer-absorption zone 5-side of the matrix 2, anti-alkaline phosphatase antibody (rabbit) was spotted, and the spot was dried, thereby preparing a development confirmation section 10. Subsequently, 5 µl of an alkaline phosphatase-labeled anti-influenza A H5-specific antibody which was produced by labeling IFH5-115 antibody with alkaline phosphatase (ALP-IFH5-115, 10 µg/ml) was spotted on the matrix, and the spot was dried, thereby preparing a labeled reagent zone comprising an enzyme labeling reagent pad 4.

Figure 8:
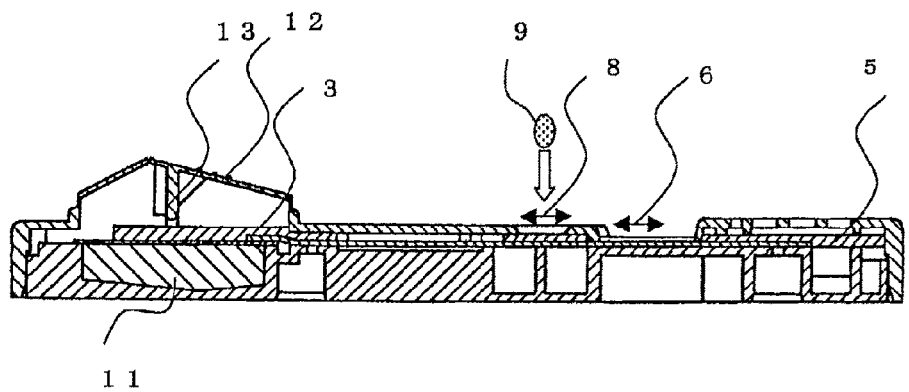
FIG. 8 is a schematic cross-sectional view of the immunoassay device (immunochromatographic device) prepared in Examples.

In a developer pad 3, 100 µg of 5-bromo-4-chloro-3-indolyl phosphate (BCIP) was spotted as a substrate in the form of a line having a width of 6.0 mm on a filter paper having a width of 6 mm and length of 20 mm (manufactured by Millipore), and the spot was dried, to prepare a substrate zone 7. The matrix 2, the developer pad 3, the enzyme labeling reagent pad 4 and an absorption pad 5 (filter paper of 10 mm width, 15 mm length and 1 mm thickness (manufactured by Whatman)) were immobilized in a plastic case having a developer tank 11, to produce the influenza A H5 immunoassay device 1 shown in FIGS. 7 and 8.

Example 6

Preparation of the Influenza A H5 Immunoassay Device 2

In the same manner as shown in FIG. 6 in Example 5, at the position 15 mm distant from the end of the developer-absorption zone 5-side of a matrix 2 which is a nitrocellulose membrane having a width of 5 mm and a length of 50 mm (manufactured by Millipore), 0.7 μl of an aqueous solution containing an anti-influenza A H5-specific antibody (IFH5-136) was spotted, and the spot was dried, thereby preparing a detection zone 6. Further, at the position 12 mm distant from the end of the developer-absorption zone 5-side of the matrix 2, anti-alkaline phosphatase antibody (rabbit) was spotted, and the spot was dried, thereby preparing a development confirmation section 10. Subsequently, 5 μl of an alkaline phosphatase-labeled anti-influenza A H5-specific antibody which was produced by labeling IFH5-115 antibody with alkaline phosphatase (ALP-IFH5-115, 10 μg/ml) was spotted on the matrix, and the spot was dried, thereby preparing a labeled reagent zone comprising an enzyme labeling reagent pad 4.

Further, in the same manner as in Example 5, the substrate was spotted and dried to prepare a developer pad 3, which was then immobilized, together with the matrix 2, the enzyme labeling reagent pad 4 and the absorption pad 5, in a plastic case having a developer tank 11, to produce the influenza A H5 immunoassay device 2 similar to the device shown in FIGS. 6 and 7.

Example 7

Preparation of the Influenza A H5 Immunoassay Device 3

In the same manner as shown in FIG. 6 in Example 5, at the position 15 mm distant from the end of the developer-absorption zone 5-side of a matrix 2 which is a nitrocellulose membrane having a width of 5 mm and a length of 50 mm (manufactured by Millipore), 0.7 μl of an aqueous solution containing an anti-influenza A H5-specific antibody (IFH5-136) was spotted, and the spot was dried, thereby preparing a detection zone 6. Further, at the position 12 mm distant from the end of the developer-absorption zone 5-side of the matrix 2, an anti-alkaline phosphatase antibody (rabbit) was spotted, and the spot was dried, thereby preparing a development confirmation section 10. Subsequently, 5 μl of an alkaline phosphatase-labeled anti-influenza A H5-specific antibody which was produced by labeling IFH5-26 antibody with alkaline phosphatase (ALP-IFH5-26, 10 μg/ml) was spotted on the matrix, and the spot was dried, thereby preparing a labeled reagent zone comprising an enzyme labeling reagent pad 4.

Further, in the same manner as in Example 5, the substrate was spotted and dried to prepare a developer pad 3, which was then immobilized, together with the matrix 2, the enzyme labeling reagent pad 4 and the absorption pad 5, in a plastic case having a developer tank 11, to produce the influenza A H5 immunoassay device 3 similar to the device shown in FIGS. 6 and 7.

Example 8

Assay of Each Subtype of Influenza A with the Immunoassay Devices 1, 2 and 3

Using the influenza A H5 immunoassay (immunochromatography) devices 1, 2 and 3 (measurement devices of the present invention) produced in Examples 5, 6 and 7, and various influenza A virus subtype samples, the reaction specificities of the immunoassay devices against the influenza A virus subtype (H1-15) were tested. As each influenza A virus subtype sample, chorioallantoic fluid whose hemagglutination titer (HA titer) was known was used, which chorioallantoic fluid was obtained by culturing each virus in an embryonated egg and recovering the chorioallantoic fluid (see Table 4). Each chorioallantoic fluid was 10-fold diluted with a sample diluent (Tris buffer (pH 8.0) containing a surfactant), and 30 μL of the dilution was added to a sample spotting zone 8. A pushing area 12 provided in a deformable member was then pushed down to be deformed, thereby inserting, with a projection 13 provided in the deformable member, the developer pad 3 into the developer tank 11 to supply the developer to the developer pad 3 to start the measurement. Fifteen minutes after the start of the measurement, development of the developer was confirmed by coloring of the subject reagent zone 10, and coloring of the detection zone 6 was visually observed. The results are shown in Table 7. It was confirmed that all of the immunoassay devices specifically detect the influenza A virus H5 subtype and are not reactive with the other subtypes (H1 to 4 and H6 to 15) of influenza A virus.

TABLE 7

Reactivity of the immunoassay devices against influenza A virus substrains

| | | Immunoassay device 1 | Immunoassay device 2 | Immunoassay device 3 | | |
|---|---|---|---|---|---|---|
| | | Solid phase antibody | | | | |
| | | IFH5-26 | IFH5-136 | IFH5-136 | | SEQ ID NO: |
| | HA | Labeled antibody | | | GenBank | base/amino |
| Influenza A virus substrain (H1-15) | titer | IFH5-115 | IFH5-115 | IFH5-26 | Accession No. | acid |
| A/PR/8/34 (H1N1) | 512 | – | – | – | J02144 | 5/6 |
| A/Singapore/1/57 (H2N2) | 64 | – | – | – | L11142 | 7/8 |
| A/duck/Ukraine/63 (H3N8) | 512 | – | – | – | V01087, J02109 | 9/10 |

TABLE 7-continued Reactivity of the immunoassay devices against influenza A virus substrains

| | | Immunoassay device 1 | Immunoassay device 2 | Immunoassay device 3 | | |
|---|---|---|---|---|---|---|
| | | | Solid phase antibody | | | |
| | | IFH5-26 | IFH5-136 | IFH5-136 | | SEQ ID NO: |
| | HA | | Labeled antibody | | GenBank | base/amino |
| Influenza A virus substrain (H1-15) | titer | IFH5-115 | IFH5-115 | IFH5-26 | Accession No. | acid |
| A/duck/Czech/56 (H4N6) | 256 | − | − | − | AB295611 | 11/12 |
| A/swan/Hokkaido/51/96 (H5N3) | 64 | + | + | + | AB241617 | 13/14 |
| A/turkey/Massachusetts/3740/65 (H6N2) | 64 | − | − | − | AB296072 | 15/16 |
| A/seal/Massachusetts/1/80 (H7N7) | 256 | − | − | − | AB269696 | 17/18 |
| A/turkey/Ontario/6118/68 (H8N4) | 128 | − | − | − | AB289343 | 19/20 |
| A/turkey/Wisconsin/66 (H9N2) | 128 | − | − | − | AB295601 | 21/22 |
| A/chicken/Germany/N/49 (H10N7) | 512 | − | − | − | AB292666 | 23/24 |
| A/duck/England/1/56 (H11N6) | 128 | − | − | − | J02107 | 25/26 |
| A/duck/Alberta/60/76 (H12N5) | 256 | − | − | − | J02104 | 27/28 |
| A/gull/Maryland/704/77 (H13N6) | 128 | − | − | − | AB292664 | 29/30 |
| A/mallard/Astrakhan/263/82 (H14N5) | 256 | − | − | − | AB289335 | 31/32 |
| A/duck/Australian/341/83 (H15N8) | 128 | − | − | − | AB295613 | 33/34 |

Further, the specificities and the detection sensitivities against influenza A virus H5 substrains were tested. As each influenza A virus H5 substrain, chorioallantoic fluid whose hemagglutination titer (HA titer) was known was used, which chorioallantoic fluid was obtained by culturing each virus in an embryonated egg and recovering the chorioallantoic fluid (see Table 7). Each chorioallantoic fluid was serially diluted with a sample diluent (Tris buffer (pH 8.0) containing a surfactant), and 30 μl of each resulting dilution was added to the sample addition zone 8. The pushing area 12 provided in the deformable member was then pushed down to be deformed, thereby inserting, with a projection 13 provided in the deformable member, the developer pad 3 into the developer tank 11 to supply the developer to the developer pad 3 to start the measurement. Fifteen minutes after the start of the measurement, development of the developer was confirmed by coloring of the development confirmation section 10, and coloring of the detection zone 6 was visually observed. The results are shown in Table 8. Each detection sensitivity was represented as the maximum dilution rate of each chorioallantoic fluid at which the virus was detectable, which chorioallantoic fluid had been serially diluted. All of the immunoassay devices detected the influenza A virus H5 substrains that were tested.

Example 9

Preparation of the Immunoassay Device 4 for Simultaneous Assay of Influenza A and Influenza A H5

Figure 9:
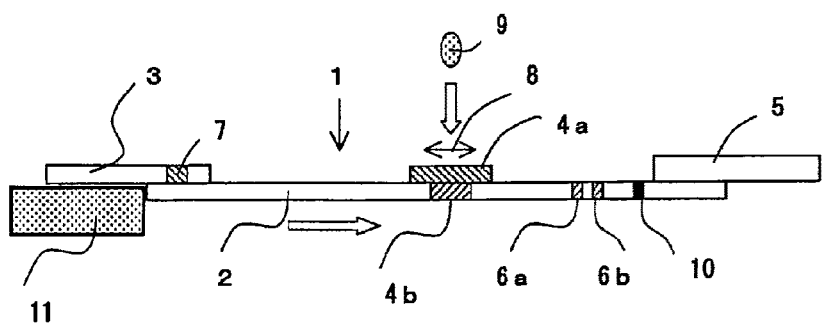
FIG. 9 is a schematic cross-sectional view of the main part of another immunoassay device (immunochromatographic device) prepared in Examples.

As shown in FIG. 9, at the positions 16 mm and 13.5 mm distant from the end of the developer-absorption zone 5-side of a matrix 2 which is a nitrocellulose membrane having a width of 5 mm and a length of 50 mm (manufactured by Millipore), 0.7 μl each of aqueous solutions containing the anti-H5 subtype influenza A virus hemagglutinin H5-specific antibody (IFH5-26) produced in Reference Example 2 and an anti-influenza A virus antibody (FVA2-11) (Literature: Gui-Rong BAI et. al.: Improvement of a Rapid Diagnosis Kit to Detect Either Influenza A or B Virus Infection. J. Vet. Med. Sci. 68(1); 1-6, 2006), respectively, was spotted, and the spots were dried, thereby preparing detection zones 6a and 6b. Further, at the position 11 mm distant from the end of the developer-absorption zone 5-side of the matrix 2, an anti-alkaline phosphatase antibody (rabbit) was spotted, and the spot was dried, thereby preparing a development confirmation section 10. Subsequently, 5 μl of a mixed aqueous solution of the alkaline phosphatase-labeled anti-influenza A

TABLE 8

Reactivities and detection sensitivities of the immunoassay devices against the influenza A virus H5 subtype

| | | Immunoassay device 1 | Immunoassay device 2 | Immunoassay device 3 | | |
|---|---|---|---|---|---|---|
| | | | Solid phase antibody | | | |
| | | IFH5-26 | IFH5-136 | IFH5-136 | | SEQ ID NO: |
| | HA | | Labeled antibody | | GenBank | base/amino |
| Influenza A virus substrain (H1-15) | titer | IFH5-115 | IFH5-115 | IFH5-26 | Accession No. | acid |
| A/swan/Hokkaido/51/96 (H5N3) | 256 | 10000 | 10000 | 1000 | AB241617 | 13/14 |
| A/Tern/South Africa/61 (H5N3) | 2048 | 4000 | 4000 | 10 | U20460 | 35/36 |
| A/Hong Kong/483/97 (H5N1) | 2048 | 40000 | 40000 | 1000 | AF084280 | 37/38 |
| A/Duck/Yokohama/aq10/03 (H5N1) | 128 | 1000 | 1000 | 1000 | AB212280 | 39/40 |
| A/Viet Nam/1184/04 (H5N1) | 512 | 8000 | 8000 | 1000 | EF541402 | 41/42 |
| A/Chicken/Yamaguchi/7/04 (H5N1) | 1024 | 2000 | 2000 | 1000 | AB166862 | 43/44 |
| A/Whooper Swan/Mongolia/3/05 (H5N1) | 16 | 2000 | 100 | 100 | AB233320 | 45/46 |
| A/Whooper Swan/Mongolia/2/06 (H5N1) | 256 | 2000 | 2000 | 1000 | AB263752 | 47/48 | virus antibody (5 μg/mL) produced in Reference Example 1 and an alkaline phosphatase-labeled anti-influenza A H5-specific antibody (ALP-IFH-115 (10 μg/mL)) was spotted on the matrix, and the spot was dried, thereby preparing a labeled reagent zone comprising an enzyme labeling reagent pad 4.

Figure 10:
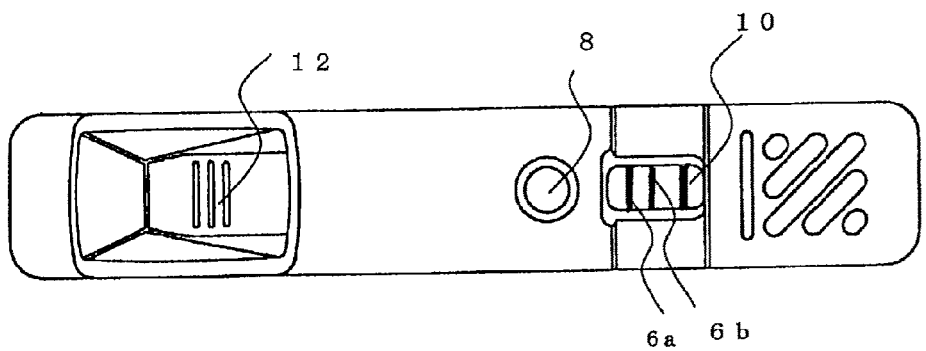
FIG. 10 is a schematic plan view of another immunoassay device (immunochromatographic device) prepared in Examples.

On a filter paper having a width of 6 mm and length of 20 mm (manufactured by Millipore), 100 μg of 5-bromo-4-chloro-3-indolyl phosphate (BCIP) was spotted as a substrate in the form of a line having a width of 6.0 mm, and the spot was dried, to prepare a developer pad 3. The matrix 2, the developer pad 3, the enzyme labeling reagent pad 4 and an absorption pad 5 (filter paper of 10 mm width, 15 mm length and 1 mm thickness (manufactured by Whatman)) were immobilized in a plastic case having a developer tank 11, to produce the simultaneous immunoassay device 4 for influenza A virus and influenza A H5 virus shown in FIG. 10 and FIG. 8.

Example 10

Assay of Each Subtype of Influenza A with the Simultaneous Immunoassay Device 4

To the sample addition zone 8 of the simultaneous immunoassay device 4 (immunoassay device according to the present invention) for influenza A virus and A H5 virus prepared in Example 9, 30 μL each of the samples of influenza A virus subtypes described in Tables 7 and 8 (Tris buffer (pH 8.0) containing a surfactant was used as the sample diluent) was added, and the pushing area 12 provided in the deformable member was then pushed down to be deformed, thereby inserting, with the projection 13 provided in the deformable member, the developer pad 3 into the developer tank 11 to supply the developer to the developer pad 3 to start the measurement. Fifteen minutes after the start of the measurement, development of the developer was confirmed by coloring of the development confirmation section 10, and coloring of the detection zones 6a and 6b was visually observed.

As a result of testing of the influenza A subtypes H1 to H15 using chorioallantoic fluid obtained by culture with embryonated eggs, coloring of the both 6a and 6b lines in the detection zone was observed for the H5 strain, and the strains other than H5, that is, the H1 to H4 and the H6 to H15 strains, showed coloring of only the 6b line (line for detection of the entire A type) in the detection zone. With uninfected chorioallantoic fluid, no coloration was detected in the 6a and 6b lines in the detection zone.

The invention claimed is:

1. A method of immunoassay of H5 subtype influenza A virus, comprising measurement of H5 subtype influenza A virus in a sample by immunoassay using antigen-antibody reaction of a monoclonal antibody or an antigen-binding fragment thereof which undergoes antigen-antibody reaction with hemagglutinin of H5 subtype influenza A virus, whose corresponding epitope does not exist in the receptor subdomain (excluding C-terminal region thereof consisting of 11 amino acids) and which does not have neutralizing activity against said influenza A virus with hemagglutinin of the H5 subtype influenza A virus.

2. The method according to claim 1, carried out by a sandwich immunoassay using 2 types of the monoclonal antibody and/or an antigen-binding fragment thereof according to claim 4, said 2 types of the monoclonal antibody and/or the antigen-binding fragment thereof being capable of binding at the same time to a single hemagglutinin molecule of H5 subtype influenza A virus.

3. The method according to claim 2, carried out using 2 types out of the 3 types of monoclonal antibodies whose corresponding epitopes exist in:
  (1) the regions of 41 to 60 aa and 312 to 322 aa;
  (2) the regions of 61 to 80 aa and 290 to 300 aa; and
  (3) the regions of 101 to 113 aa and 268 to 278 aa,
  based on the amino acid sequence shown in SEQ ID NO:2.

4. The method according to claim 3, carried out by an immunochromatography.

5. An immunoassay kit for H5 subtype influenza A virus, comprising 2 types of a monoclonal antibody and/or an antigen-binding fragment thereof which undergoes antigen-antibody reaction with hemagglutinin of H5 subtype influenza A virus, whose corresponding epitope does not exist in the receptor subdomain (excluding C-terminal region thereof consisting of 11 amino acids) and which does not have neutralizing activity against said influenza A virus, said 2 types of the antibody and/or the antigen-binding fragment thereof being capable of binding at the same time to hemagglutinin of H5 subtype influenza A virus.

6. The kit according to claim 5, wherein one of said 2 types of the monoclonal antibody and/or the antigen-binding fragment thereof is immobilized on a solid phase and the other is labeled.

7. The kit according to claim 6, wherein said solid phase is a solid phase for immunochromatography.

8. The method according to claim 1, wherein the monoclonal antibody or an antigen-binding fragment thereof is substantially non-cross-reactive with hemagglutinins of H1 to H4 subtypes and H6 to H15 subtypes.

9. The method according to claim 1, wherein the monoclonal antibody or an antigen-binding fragment thereof is an antibody or antigen-binding fragment thereof whose corresponding epitope exists in:
  (1) the regions of 41 to 60 aa and 312 to 322 aa;
  (2) the regions of 61 to 80 aa and 290 to 300 aa; or
  (3) the regions of 101 to 113 aa and 268 to 278 aa,
based on the amino acid sequence shown in SEQ ID NO:2.

10. The immunoassay kit according to claim 5, wherein at least one of the two types of the monoclonal antibody or an antigen-binding fragment thereof is substantially non-cross-reactive with hemagglutinins of H1 to H4 subtypes and H6 to H15 subtypes.

11. The immunoassay kit according to claim 5, comprising 2 types out of the 3 types of monoclonal antibodies whose corresponding epitopes exist in:
  (1) the regions of 41 to 60 aa and 312 to 322 aa;
  (2) the regions of 61 to 80 aa and 290 to 300 aa; or
  (3) the regions of 101 to 113 aa and 268 to 278 aa,
based on the amino acid sequence shown in SEQ ID NO:2.

* * * * *

SEQUENCE LISTING

```
<160> NUMBER OF SEQ ID NOS: 50

<210> SEQ ID NO 1
<211> LENGTH: 1732
<212> TYPE: DNA
<213> ORGANISM: Influenza A virus
<220> FEATURE:
<221> NAME/KEY: CDS
<222> LOCATION: (15)..(1709)
<223> OTHER INFORMATION:

<400> SEQUENCE: 1
tctaatctgt taaa atg gag aaa ata gta ctt ctt ttt gca ata gtc agt      50
             Met Glu Lys Ile Val Leu Leu Phe Ala Ile Val Ser
             1               5                   10 ctt gtc aaa agt gac caa att tgc att ggt tac cat gca aac aac tca      98
Leu Val Lys Ser Asp Gln Ile Cys Ile Gly Tyr His Ala Asn Asn Ser
        15                  20                  25 aca gag cag gtt gac aca ata atg gaa aag aat gtt act gtc acg cat    146
Thr Glu Gln Val Asp Thr Ile Met Glu Lys Asn Val Thr Val Thr His
    30                  35                  40 gcc caa gac ata ctg gaa aag aca cac aat ggg aag ctc tgc agt cta    194
Ala Gln Asp Ile Leu Glu Lys Thr His Asn Gly Lys Leu Cys Ser Leu
45                  50                  55                  60 aat gga gtt aag cct ctc att ttg agg gat tgt agt gta gct gga tgg    242
Asn Gly Val Lys Pro Leu Ile Leu Arg Asp Cys Ser Val Ala Gly Trp
                65                  70                  75 ctc ctc gga aac ccc atg tgt gat gaa ttc ctc aat gtg ccg gaa tgg    290
Leu Leu Gly Asn Pro Met Cys Asp Glu Phe Leu Asn Val Pro Glu Trp
            80                  85                  90 tct tac ata gtg gag aag gac agc cca atc aat ggc ctc tgc tac cca    338
Ser Tyr Ile Val Glu Lys Asp Ser Pro Ile Asn Gly Leu Cys Tyr Pro
        95                  100                 105 ggg gat ttc aac gac tat gaa gag ctg aaa cac ctg ttg agc agt aca    386
Gly Asp Phe Asn Asp Tyr Glu Glu Leu Lys His Leu Leu Ser Ser Thr
    110                 115                 120 aac cat ttt gag aaa att caa atc atc ccc agg agt tct tgg tcc gat    434
```

-continued

| | | |
|---|---|---|
| Asn His Phe Glu Lys Ile Gln Ile Ile Pro Arg Ser Ser Trp Ser Asp<br>125                          130                    135                    140 | | cat gat gcc tca tca gga gtg agc tcc gca tgt cca tat aat ggg agg    482
His Asp Ala Ser Ser Gly Val Ser Ser Ala Cys Pro Tyr Asn Gly Arg
                    145                    150                    155 tcc tcc ttt ttc aga aat gta gtg tgg ctc atc aaa aag aac aat gca    530
Ser Ser Phe Phe Arg Asn Val Val Trp Leu Ile Lys Lys Asn Asn Ala
                    160                    165                    170 tac cca aca ata aaa agg aat tac aat aat act aac caa gaa gat ctt    578
Tyr Pro Thr Ile Lys Arg Asn Tyr Asn Asn Thr Asn Gln Glu Asp Leu
                    175                    180                    185 ttg gta ctg tgg ggg att cac cat cct aat gat gca aca gag cag aca    626
Leu Val Leu Trp Gly Ile His His Pro Asn Asp Ala Thr Glu Gln Thr
                    190                    195                    200 aag ctc tat caa aac cca acc acc tat gtt tct gtt gga aca tca aca    674
Lys Leu Tyr Gln Asn Pro Thr Thr Tyr Val Ser Val Gly Thr Ser Thr
205                          210                    215                    220 ctg aac cag aga tcg gtc cca gaa ata gct acc agg ccc aaa gta aat    722
Leu Asn Gln Arg Ser Val Pro Glu Ile Ala Thr Arg Pro Lys Val Asn
                    225                    230                    235 ggg caa agt gga aga ata gag ttt ttc tgg aca atc tta aag cca aat    770
Gly Gln Ser Gly Arg Ile Glu Phe Phe Trp Thr Ile Leu Lys Pro Asn
                    240                    245                    250 gat gcc atc aat ttc gag agt aat gga aat ttt att gct cca gaa tat    818
Asp Ala Ile Asn Phe Glu Ser Asn Gly Asn Phe Ile Ala Pro Glu Tyr
                    255                    260                    265 gca tac aaa att gcc aag aaa gga gac tca gca atc atg aaa agt gga    866
Ala Tyr Lys Ile Ala Lys Lys Gly Asp Ser Ala Ile Met Lys Ser Gly
          270                    275                    280 ttg gag tat ggt aac tgc aac acc aag tgt caa act cca atg ggt gca    914
Leu Glu Tyr Gly Asn Cys Asn Thr Lys Cys Gln Thr Pro Met Gly Ala
285                          290                    295                    300 ata aac tcc agc atg cca ttt cac aac ata cac cct ctc acc att ggg    962
Ile Asn Ser Ser Met Pro Phe His Asn Ile His Pro Leu Thr Ile Gly
                    305                    310                    315 gaa tgc ccc aga tac gtg aag tca gat aga tta gtc ctt gca aca ggg    1010
Glu Cys Pro Arg Tyr Val Lys Ser Asp Arg Leu Val Leu Ala Thr Gly
          320                    325                    330 ctc agg aat gtc cct caa aga gaa aca aga gga cta ttt ggg gcc ata    1058
Leu Arg Asn Val Pro Gln Arg Glu Thr Arg Gly Leu Phe Gly Ala Ile
                335                    340                    345 gca ggc ttc ata gaa gga ggg tgg caa gga atg gta gac ggt tgg tat    1106
Ala Gly Phe Ile Glu Gly Gly Trp Gln Gly Met Val Asp Gly Trp Tyr
          350                    355                    360 gga tac cac cat agc aac gag caa ggg agt gga tac gct gca gac aaa    1154
Gly Tyr His His Ser Asn Glu Gln Gly Ser Gly Tyr Ala Ala Asp Lys
365                          370                    375                    380 gag tcc act caa aag gca ata gat gga atc act aat aag gtc aac tca    1202
Glu Ser Thr Gln Lys Ala Ile Asp Gly Ile Thr Asn Lys Val Asn Ser
                    385                    390                    395 atc att gac aaa atg aac act cag ttt gag gcc gtt gga aag gaa ttt    1250
Ile Ile Asp Lys Met Asn Thr Gln Phe Glu Ala Val Gly Lys Glu Phe
                400                    405                    410 aat aac tta gaa agg agg ata gag aat ttg aac aag aaa atg gaa gac    1298
Asn Asn Leu Glu Arg Arg Ile Glu Asn Leu Asn Lys Lys Met Glu Asp
                415                    420                    425 gga ttc cta gat gtc tgg act tat aat gct gaa ctt ctg gtt ctc atg    1346
Gly Phe Leu Asp Val Trp Thr Tyr Asn Ala Glu Leu Leu Val Leu Met
          430                    435                    440 gaa aat gag aga acc cta gac ttt cat gac tca aat gtc aag aac ctt    1394

```
Glu Asn Glu Arg Thr Leu Asp Phe His Asp Ser Asn Val Lys Asn Leu
445                 450                 455                 460 tac gac aag gtt cga cta cag ctt agg gat aat gca aag gag ctg ggt     1442
Tyr Asp Lys Val Arg Leu Gln Leu Arg Asp Asn Ala Lys Glu Leu Gly
                465                 470                 475 aat ggt tgt ttc gag ttc tat cac aaa tgt gat gat gaa tgt atg gaa     1490
Asn Gly Cys Phe Glu Phe Tyr His Lys Cys Asp Asp Glu Cys Met Glu
            480                 485                 490 agt gta aga aac gga acg tat gac tac ccg cag tat tca gaa gag gca     1538
Ser Val Arg Asn Gly Thr Tyr Asp Tyr Pro Gln Tyr Ser Glu Glu Ala
        495                 500                 505 aga cta aac aga gag gaa ata agt gga gta aaa ttg gaa tca ata gga     1586
Arg Leu Asn Arg Glu Glu Ile Ser Gly Val Lys Leu Glu Ser Ile Gly
510                 515                 520 act tac caa ata ttg tca att tat tca aca gtg gcg agt tcc tta gca     1634
Thr Tyr Gln Ile Leu Ser Ile Tyr Ser Thr Val Ala Ser Ser Leu Ala
525                 530                 535                 540 ctg gca atc atg gta gct ggt cta tct ttc tgg atg tgc tcc aat gga     1682
Leu Ala Ile Met Val Ala Gly Leu Ser Phe Trp Met Cys Ser Asn Gly
                545                 550                 555 tca ttg caa tgc aga att tgc att taa acttgtgagt tcagattgta gtt        1732
Ser Leu Gln Cys Arg Ile Cys Ile
            560

<210> SEQ ID NO 2
<211> LENGTH: 564
<212> TYPE: PRT
<213> ORGANISM: Influenza A virus

<400> SEQUENCE: 2

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Ser Pro Ile Asn Gly Leu Cys Tyr Pro Gly Asp Phe Asn
            100                 105                 110

Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asp His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Asn Tyr Asn Asn Thr Asn Gln Glu Asp Leu Leu Val Leu Trp
            180                 185                 190

Gly Ile His His Pro Asn Asp Ala Thr Glu Gln Thr Lys Leu Tyr Gln
        195                 200                 205

Asn Pro Thr Thr Tyr Val Ser Val Gly Thr Ser Thr Leu Asn Gln Arg
    210                 215                 220
```

| | | | | | | | | | | | | | | |
|---|---|---|---|---|---|---|---|---|---|---|---|---|---|---|
|Ser|Val|Pro|Glu|Ile|Ala|Thr|Arg|Pro|Lys|Val|Asn|Gly|Gln|Ser|Gly|
|225| | | | |230| | | | |235| | | | |240|

Arg Ile Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Ala Lys Lys Gly Asp Ser Ala Ile Met Lys Ser Gly Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Arg
305                 310                 315                 320

Tyr Val Lys Ser Asp Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asp Glu Cys Met Glu Ser Val Arg Asn
                485                 490                 495

Gly Thr Tyr Asp Tyr Pro Gln Tyr Ser Glu Glu Ala Arg Leu Asn Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 3
<211> LENGTH: 1761
<212> TYPE: DNA
<213> ORGANISM: Influenza A virus
<220> FEATURE:
<221> NAME/KEY: CDS
<222> LOCATION: (24)..(1718)
<223> OTHER INFORMATION:

<400> SEQUENCE: 3
tagcaggggt ataatctgtc aag atg gag aaa ata gtg ctt ctt ctt gca ata      53
                        Met Glu Lys Ile Val Leu Leu Leu Ala Ile

|         |         |         |         |         |         |         |         |         |         |         |         |         |         |         |         |      |
|---------|---------|---------|---------|---------|---------|---------|---------|---------|---------|---------|---------|---------|---------|---------|---------|------|
| gtc     | agt     | ctt     | gtt     | aaa     | agt     | gac     | cag     | att     | tgc     | att     | ggt     | tac     | cat     | gca     | aat     | 101  |
| Val     | Ser     | Leu     | Val     | Lys     | Ser     | Asp     | Gln     | Ile     | Cys     | Ile     | Gly     | Tyr     | His     | Ala     | Asn     |      |
|         |         |         |         | 15      |         |         |         | 20      |         |         |         | 25      |         |         |         |      |

```
gtc agt ctt gtt aaa agt gac cag att tgc att ggt tac cat gca aat         101
Val Ser Leu Val Lys Ser Asp Gln Ile Cys Ile Gly Tyr His Ala Asn
             15              20              25 aac tcg aca gag cag gtt gac aca ata atg gaa aag aat gtt act gtt         149
Asn Ser Thr Glu Gln Val Asp Thr Ile Met Glu Lys Asn Val Thr Val
         30              35              40 aca cat gct caa gac ata ttg gaa aag aca cac aac ggg aag ctc tgc         197
Thr His Ala Gln Asp Ile Leu Glu Lys Thr His Asn Gly Lys Leu Cys
             45              50              55 agt cta aat gga gtg aaa cct ctc att ttg agg gat tgt agt gta gct         245
Ser Leu Asn Gly Val Lys Pro Leu Ile Leu Arg Asp Cys Ser Val Ala
         60              65              70 gga tgg ctc ctc gga aac cct atg tgt gac gaa ttc ctc aat gtg ccg         293
Gly Trp Leu Leu Gly Asn Pro Met Cys Asp Glu Phe Leu Asn Val Pro
75              80              85              90 gaa tgg tct tac ata gtg gag aag gac aat cca gtc aat ggc ctc tgc         341
Glu Trp Ser Tyr Ile Val Glu Lys Asp Asn Pro Val Asn Gly Leu Cys
             95             100             105 tac cca gga gat ttc aac gac tat gaa gaa ctg aaa cac cta ttg agc         389
Tyr Pro Gly Asp Phe Asn Asp Tyr Glu Glu Leu Lys His Leu Leu Ser
        110             115             120 agc aca aac cat ttt gag aaa atc cga atc atc ccc aga agc tct tgg         437
Ser Thr Asn His Phe Glu Lys Ile Arg Ile Ile Pro Arg Ser Ser Trp
        125             130             135 tcc aat cat gat gcc tca tca gga gtg agc tct gca tgt cca tat aat         485
Ser Asn His Asp Ala Ser Ser Gly Val Ser Ser Ala Cys Pro Tyr Asn
140             145             150 ggg agg tcc tcc ttt ttc aga aat gtg gta tgg ctt atc aaa aag aac         533
Gly Arg Ser Ser Phe Phe Arg Asn Val Val Trp Leu Ile Lys Lys Asn
155             160             165             170 aat gca tac cca aca ata aag agg agt tac aat aac acc aac caa gaa         581
Asn Ala Tyr Pro Thr Ile Lys Arg Ser Tyr Asn Asn Thr Asn Gln Glu
            175             180             185 gat ctt ttg ata ctg tgg ggg att cac cat cct aat gat gcg gca gag         629
Asp Leu Leu Ile Leu Trp Gly Ile His His Pro Asn Asp Ala Ala Glu
        190             195             200 cag aca aag ctc tat caa aac cca act acc tac gtt tcc gtt gga aca         677
Gln Thr Lys Leu Tyr Gln Asn Pro Thr Thr Tyr Val Ser Val Gly Thr
        205             210             215 tca aca ctg aac cag aga tcg gtc cca gaa ata gct acc agg ccc aaa         725
Ser Thr Leu Asn Gln Arg Ser Val Pro Glu Ile Ala Thr Arg Pro Lys
220             225             230 gtg aac ggg caa agt gga aga atg gag ttc ttc tgg aca att tta aag         773
Val Asn Gly Gln Ser Gly Arg Met Glu Phe Phe Trp Thr Ile Leu Lys
235             240             245             250 ccg aat gat gcc atc aat ttt gag agt aat gga aat ttc att gct cca         821
Pro Asn Asp Ala Ile Asn Phe Glu Ser Asn Gly Asn Phe Ile Ala Pro
            255             260             265 gaa tat gca tac aaa att gtc aaa aaa gga ggc tca gca atc atg aaa         869
Glu Tyr Ala Tyr Lys Ile Val Lys Lys Gly Gly Ser Ala Ile Met Lys
        270             275             280 agt gga ttg gaa tat ggt aac tgc aac acc aag tgt caa act cca atg         917
Ser Gly Leu Glu Tyr Gly Asn Cys Asn Thr Lys Cys Gln Thr Pro Met
285             290             295 ggt gcg ata aac tct agt atg cca ttc cat aac ata cac cct ctc acc         965
Gly Ala Ile Asn Ser Ser Met Pro Phe His Asn Ile His Pro Leu Thr
        300             305             310 att gga gaa tgc ccc aaa tat gtg aaa tca ggt aga tta gtc ctt gca        1013
Ile Gly Glu Cys Pro Lys Tyr Val Lys Ser Gly Arg Leu Val Leu Ala
```

```
                 315                 320                 325                 330
act gga ctc aga aat gtc cct caa aga gaa aca aga gga cta ttt ggg          1061
Thr Gly Leu Arg Asn Val Pro Gln Arg Glu Thr Arg Gly Leu Phe Gly
                    335                 340                 345 gct ata gca ggc ttt ata gaa gga gga tgg caa gga atg gta gac ggt          1109
Ala Ile Ala Gly Phe Ile Glu Gly Gly Trp Gln Gly Met Val Asp Gly
            350                 355                 360 tgg tat ggg tac cac cat agc aac gag cag ggg agt gga tac gct gca          1157
Trp Tyr Gly Tyr His His Ser Asn Glu Gln Gly Ser Gly Tyr Ala Ala
        365                 370                 375 gac aaa gaa tcc act caa aag gca ata gat gga atc act aat aag gtc          1205
Asp Lys Glu Ser Thr Gln Lys Ala Ile Asp Gly Ile Thr Asn Lys Val
    380                 385                 390 aac tca atc att gac aaa atg aac act cag ttt gag gcc gtt gga aag          1253
Asn Ser Ile Ile Asp Lys Met Asn Thr Gln Phe Glu Ala Val Gly Lys
395                 400                 405                 410 gaa ttt aat aac ttg gaa agg agg ata gag aat ttg aat aag aaa atg          1301
Glu Phe Asn Asn Leu Glu Arg Arg Ile Glu Asn Leu Asn Lys Lys Met
                    415                 420                 425 gaa gac gga ttt cta gat gtc tgg act tat aat gct gaa ctt ttg gtt          1349
Glu Asp Gly Phe Leu Asp Val Trp Thr Tyr Asn Ala Glu Leu Leu Val
            430                 435                 440 cta atg gaa aat gag aga acc cta gac ttt cat gac tca aat gtc aag          1397
Leu Met Glu Asn Glu Arg Thr Leu Asp Phe His Asp Ser Asn Val Lys
        445                 450                 455 aac ctt tat gac aag gtt cga cta cag ctt agg gat aat gca aag gag          1445
Asn Leu Tyr Asp Lys Val Arg Leu Gln Leu Arg Asp Asn Ala Lys Glu
    460                 465                 470 ctg ggt aat ggt tgt ttc gag ttc tac cat aaa tgt gat aat gaa tgt          1493
Leu Gly Asn Gly Cys Phe Glu Phe Tyr His Lys Cys Asp Asn Glu Cys
475                 480                 485                 490 atg gaa agt gta aaa aac ggg acg tat gac tac ccg cag tat tca gaa          1541
Met Glu Ser Val Lys Asn Gly Thr Tyr Asp Tyr Pro Gln Tyr Ser Glu
                    495                 500                 505 gag gca aga cta aac aga gag gaa ata agt ggg gtg aaa ttg gaa tca          1589
Glu Ala Arg Leu Asn Arg Glu Glu Ile Ser Gly Val Lys Leu Glu Ser
            510                 515                 520 atg gga att tac caa ata ctg tca att tat tca aca gtg gcg agt tcc          1637
Met Gly Ile Tyr Gln Ile Leu Ser Ile Tyr Ser Thr Val Ala Ser Ser
        525                 530                 535 cta gca ctg gca atc atg ata gct ggt cta tct ttc tgg atg tgc tcc          1685
Leu Ala Leu Ala Ile Met Ile Ala Gly Leu Ser Phe Trp Met Cys Ser
    540                 545                 550 aat gga tca ttg cag tgc aga att tgc att taa atctgtgagt tcagattgta       1738
Asn Gly Ser Leu Gln Cys Arg Ile Cys Ile
555                 560 gttaaaaaca cccttgtttc tac                                                1761

<210> SEQ ID NO 4
<211> LENGTH: 564
<212> TYPE: PRT
<213> ORGANISM: Influenza A virus

<400> SEQUENCE: 4

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45
```

```
Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Val Asn Gly Leu Cys Tyr Pro Gly Asp Phe Asn
                100                 105                 110

Asp Tyr Glu Glu Leu Lys His Leu Leu Ser Ser Thr Asn His Phe Glu
            115                 120                 125

Lys Ile Arg Ile Ile Pro Arg Ser Ser Trp Ser Asn His Asp Ala Ser
        130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
210                 215                 220

Ser Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Gly Ser Ala Ile Met Lys Ser Gly Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Gly Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
```

```
                465                 470                 475                 480
Glu Phe Tyr His Lys Cys Asp Asn Glu Cys Met Glu Ser Val Lys Asn
                    485                 490                 495

Gly Thr Tyr Asp Tyr Pro Gln Tyr Ser Glu Glu Ala Arg Leu Asn Arg
                500                 505                 510

Glu Glu Ile Ser Gly Val Lys Leu Glu Ser Met Gly Ile Tyr Gln Ile
        515                 520                 525

Leu Ser Ile Tyr Ser Thr Val Ala Ser Ser Leu Ala Leu Ala Ile Met
        530                 535                 540

Ile Ala Gly Leu Ser Phe Trp Met Cys Ser Asn Gly Ser Leu Gln Cys
545                 550                 555                 560

Arg Ile Cys Ile

<210> SEQ ID NO 5
<211> LENGTH: 1015
<212> TYPE: DNA
<213> ORGANISM: Influenza A virus
<220> FEATURE:
<221> NAME/KEY: CDS
<222> LOCATION: (2)..(1015)
<223> OTHER INFORMATION:

<400> SEQUENCE: 5 c cta ctg gtc ctg tta tgt gca ctt gca gct gca gat gca gac aca ata         49
  Leu Leu Val Leu Leu Cys Ala Leu Ala Ala Ala Asp Ala Asp Thr Ile
  1               5                   10                  15 tgt ata ggc tac cat gcg aac aat tca acc gac act gtt gac aca gta          97
Cys Ile Gly Tyr His Ala Asn Asn Ser Thr Asp Thr Val Asp Thr Val
            20                  25                  30 ctc gag aag aat gtg aca gtg aca cac tct gtt aac ctg ctc gaa gac         145
Leu Glu Lys Asn Val Thr Val Thr His Ser Val Asn Leu Leu Glu Asp
        35                  40                  45 agc cac aac gga aaa cta tgt aga tta aaa gga ata gcc cca cta caa         193
Ser His Asn Gly Lys Leu Cys Arg Leu Lys Gly Ile Ala Pro Leu Gln
    50                  55                  60 ttg ggg aaa tgt aac atc gcc gga tgg ctc ttg gga aac cca gaa tgc         241
Leu Gly Lys Cys Asn Ile Ala Gly Trp Leu Leu Gly Asn Pro Glu Cys
65                  70                  75                  80 gac cca ctg ctt cca gtg aga tca tgg tcc tac att gta gaa aca cca         289
Asp Pro Leu Leu Pro Val Arg Ser Trp Ser Tyr Ile Val Glu Thr Pro
                85                  90                  95 aac tct gag aat gga ata tgt tat cca gga gat ttc atc gac tat gag         337
Asn Ser Glu Asn Gly Ile Cys Tyr Pro Gly Asp Phe Ile Asp Tyr Glu
            100                 105                 110 gag ctg agg gag caa ttg agc tca gtg tca tca ttc gaa aga ttc gaa         385
Glu Leu Arg Glu Gln Leu Ser Ser Val Ser Ser Phe Glu Arg Phe Glu
        115                 120                 125 ata ttt ccc aaa gaa agc tca tgg ccc aac cac aac aca aac gga gta         433
Ile Phe Pro Lys Glu Ser Ser Trp Pro Asn His Asn Thr Asn Gly Val
    130                 135                 140 acg gca gca tgc tcc cat gag ggg aaa agc agt ttt tac aga aat ttg         481
Thr Ala Ala Cys Ser His Glu Gly Lys Ser Ser Phe Tyr Arg Asn Leu
145                 150                 155                 160 cta tgg ctg acg gag aag gag ggc tca tac cca aag ctg aaa aat tct         529
Leu Trp Leu Thr Glu Lys Glu Gly Ser Tyr Pro Lys Leu Lys Asn Ser
                165                 170                 175 tat gtg aac aaa aaa ggg aaa gaa gtc ctt gta ctg tgg ggt att cat         577
Tyr Val Asn Lys Lys Gly Lys Glu Val Leu Val Leu Trp Gly Ile His
            180                 185                 190 cac ccg cct aac agt aag gaa caa cag aat ctc tat cag aat gaa aat         625
```

```
His Pro Pro Asn Ser Lys Glu Gln Gln Asn Leu Tyr Gln Asn Glu Asn
        195                 200                 205 gct tat gtc tct gta gtg act tca aat tat aac agg aga ttt acc ccg   673
Ala Tyr Val Ser Val Val Thr Ser Asn Tyr Asn Arg Arg Phe Thr Pro
210                 215                 220 gaa ata gca gaa aga ccc aaa gta aga gat caa gct ggg agg atg aac   721
Glu Ile Ala Glu Arg Pro Lys Val Arg Asp Gln Ala Gly Arg Met Asn
225                 230                 235                 240 tat tac tgg acc ttg cta aaa ccc gga gac aca ata ata ttt gag gca   769
Tyr Tyr Trp Thr Leu Leu Lys Pro Gly Asp Thr Ile Ile Phe Glu Ala
                245                 250                 255 aat gga aat cta ata gca cca atg tat gct ttc gca ctg agt aga ggc   817
Asn Gly Asn Leu Ile Ala Pro Met Tyr Ala Phe Ala Leu Ser Arg Gly
            260                 265                 270 ttt ggg tcc ggc atc atc acc tca aac gca tca atg cat gag tgt aac   865
Phe Gly Ser Gly Ile Ile Thr Ser Asn Ala Ser Met His Glu Cys Asn
        275                 280                 285 acg aag tgt caa aca ccc ctg gga gct ata aac agc agt ctc cct tac   913
Thr Lys Cys Gln Thr Pro Leu Gly Ala Ile Asn Ser Ser Leu Pro Tyr
290                 295                 300 cag aat ata cac cca gtc aca ata gga gag tgc cca aaa tac gtc agg   961
Gln Asn Ile His Pro Val Thr Ile Gly Glu Cys Pro Lys Tyr Val Arg
305                 310                 315                 320 agt gcc aaa ttg agg atg gtt aca gga cta agg aac att ccg tcc att  1009
Ser Ala Lys Leu Arg Met Val Thr Gly Leu Arg Asn Ile Pro Ser Ile
                325                 330                 335 caa tcc                                                          1015
Gln Ser

<210> SEQ ID NO 6
<211> LENGTH: 338
<212> TYPE: PRT
<213> ORGANISM: Influenza A virus

<400> SEQUENCE: 6

Leu Leu Val Leu Cys Ala Leu Ala Ala Ala Asp Ala Asp Thr Ile
1               5                   10                  15

Cys Ile Gly Tyr His Ala Asn Asn Ser Thr Asp Thr Val Asp Thr Val
                20                  25                  30

Leu Glu Lys Asn Val Thr Val Thr His Ser Val Asn Leu Leu Glu Asp
            35                  40                  45

Ser His Asn Gly Lys Leu Cys Arg Leu Lys Gly Ile Ala Pro Leu Gln
        50                  55                  60

Leu Gly Lys Cys Asn Ile Ala Gly Trp Leu Leu Gly Asn Pro Glu Cys
65                  70                  75                  80

Asp Pro Leu Leu Pro Val Arg Ser Trp Ser Tyr Ile Val Glu Thr Pro
                85                  90                  95

Asn Ser Glu Asn Gly Ile Cys Tyr Pro Gly Asp Phe Ile Asp Tyr Glu
            100                 105                 110

Glu Leu Arg Glu Gln Leu Ser Ser Val Ser Ser Phe Glu Arg Phe Glu
        115                 120                 125

Ile Phe Pro Lys Glu Ser Ser Trp Pro Asn His Asn Thr Asn Gly Val
130                 135                 140

Thr Ala Ala Cys Ser His Glu Gly Lys Ser Ser Phe Tyr Arg Asn Leu
145                 150                 155                 160

Leu Trp Leu Thr Glu Lys Glu Gly Ser Tyr Pro Lys Leu Lys Asn Ser
                165                 170                 175

Tyr Val Asn Lys Lys Gly Lys Glu Val Leu Val Leu Trp Gly Ile His
```

```
                      180                 185                 190
His Pro Pro Asn Ser Lys Glu Gln Gln Asn Leu Tyr Gln Asn Glu Asn
            195                 200                 205

Ala Tyr Val Ser Val Val Thr Ser Asn Tyr Asn Arg Arg Phe Thr Pro
        210                 215                 220

Glu Ile Ala Glu Arg Pro Lys Val Arg Asp Gln Ala Gly Arg Met Asn
225                 230                 235                 240

Tyr Tyr Trp Thr Leu Leu Lys Pro Gly Asp Thr Ile Ile Phe Glu Ala
                245                 250                 255

Asn Gly Asn Leu Ile Ala Pro Met Tyr Ala Phe Ala Leu Ser Arg Gly
            260                 265                 270

Phe Gly Ser Gly Ile Ile Thr Ser Asn Ala Ser Met His Glu Cys Asn
        275                 280                 285

Thr Lys Cys Gln Thr Pro Leu Gly Ala Ile Asn Ser Ser Leu Pro Tyr
290                 295                 300

Gln Asn Ile His Pro Val Thr Ile Gly Glu Cys Pro Lys Tyr Val Arg
305                 310                 315                 320

Ser Ala Lys Leu Arg Met Val Thr Gly Leu Arg Asn Ile Pro Ser Ile
                325                 330                 335

Gln Ser

<210> SEQ ID NO 7
<211> LENGTH: 1773
<212> TYPE: DNA
<213> ORGANISM: Influenza A virus
<220> FEATURE:
<221> NAME/KEY: CDS
<222> LOCATION: (44)..(1732)
<223> OTHER INFORMATION:

<400> SEQUENCE: 7
agcaaaagca ggggttatac catagacaac caaaagcaaa aca atg gcc atc att         55
                                              Met Ala Ile Ile
                                              1 tat ctc att ctc ctg ttc aca gca gtg aga ggg gac cag ata tgc att       103
Tyr Leu Ile Leu Leu Phe Thr Ala Val Arg Gly Asp Gln Ile Cys Ile
  5                  10                  15                  20 gga tac cat gcc aat aat tcc aca gag aag gtc gac aca att cta gag       151
Gly Tyr His Ala Asn Asn Ser Thr Glu Lys Val Asp Thr Ile Leu Glu
                 25                  30                  35 cgg aac gtc act gtg act cat gcc aag gac att ctt gag aag acc cat       199
Arg Asn Val Thr Val Thr His Ala Lys Asp Ile Leu Glu Lys Thr His
             40                  45                  50 aac gga aag tta tgc aaa cta aac gga atc cct cca ctt gaa cta ggg       247
Asn Gly Lys Leu Cys Lys Leu Asn Gly Ile Pro Pro Leu Glu Leu Gly
         55                  60                  65 gac tgt agc att gcc gga tgg ctc ctt gga aat cca gaa tgt gat agg       295
Asp Cys Ser Ile Ala Gly Trp Leu Leu Gly Asn Pro Glu Cys Asp Arg
 70                  75                  80 ctt cta agt gtg cca gaa tgg tcc tat ata atg gag aaa gaa aac ccg       343
Leu Leu Ser Val Pro Glu Trp Ser Tyr Ile Met Glu Lys Glu Asn Pro
85                  90                  95                 100 aga gac ggt ttg tgt tat cca ggc agc ttc aat gat tat gaa gaa ttg       391
Arg Asp Gly Leu Cys Tyr Pro Gly Ser Phe Asn Asp Tyr Glu Glu Leu
                105                 110                 115 aaa cat ctc ctc agc agc gtg aaa cat ttc gag aaa gta aag att ctg       439
Lys His Leu Leu Ser Ser Val Lys His Phe Glu Lys Val Lys Ile Leu
            120                 125                 130 ccc aaa gat aga tgg aca cag cat aca aca act gga ggt tca cgg gcc       487
```

-continued

| | | |
|---|---|---|
| Pro Lys Asp Arg Trp Thr Gln His Thr Thr Gly Gly Ser Arg Ala<br>     135                   140                   145 | | |
| tgc gcg gtg tct ggt aat cca tca ttc ttc agg aac atg gtc tgg ctg<br>Cys Ala Val Ser Gly Asn Pro Ser Phe Phe Arg Asn Met Val Trp Leu<br>     150                   155                   160 | 535 | |
| aca gag aaa gga tca aat tat ccg gtt gcc aaa gga tcg tac aac aat<br>Thr Glu Lys Gly Ser Asn Tyr Pro Val Ala Lys Gly Ser Tyr Asn Asn<br>165                   170                   175                 180 | 583 | |
| aca agc gga gaa caa atg cta ata att tgg ggg gtg cac cat ccc aat<br>Thr Ser Gly Glu Gln Met Leu Ile Ile Trp Gly Val His His Pro Asn<br>                   185                   190                 195 | 631 | |
| gat gag aaa gaa caa aga aca ttg tac cag aat gtg gga acc tat gtt<br>Asp Glu Lys Glu Gln Arg Thr Leu Tyr Gln Asn Val Gly Thr Tyr Val<br>           200                   205                   210 | 679 | |
| tcc gta ggc aca tca aca ttg aac aaa agg tca acc cca gac ata gca<br>Ser Val Gly Thr Ser Thr Leu Asn Lys Arg Ser Thr Pro Asp Ile Ala<br>                   215                   220                 225 | 727 | |
| aca agg cct aaa gtg aat gga cta gga agt aga atg gaa ttc tct tgg<br>Thr Arg Pro Lys Val Asn Gly Leu Gly Ser Arg Met Glu Phe Ser Trp<br>     230                   235                   240 | 775 | |
| acc cta ttg gat atg tgg gac acc ata aat ttt gag agt act ggt aat<br>Thr Leu Leu Asp Met Trp Asp Thr Ile Asn Phe Glu Ser Thr Gly Asn<br>245                   250                   255                 260 | 823 | |
| cta att gca cca gag tat gga ttc aaa ata tcg aaa aga ggt agt tca<br>Leu Ile Ala Pro Glu Tyr Gly Phe Lys Ile Ser Lys Arg Gly Ser Ser<br>                   265                   270                 275 | 871 | |
| ggg atc atg aaa aca gaa gga aca ctt gag aac tgt gag acc aaa tgc<br>Gly Ile Met Lys Thr Glu Gly Thr Leu Glu Asn Cys Glu Thr Lys Cys<br>           280                   285                   290 | 919 | |
| caa act cct ttg gga gca ata aat aca aca ttg cct ttt cac aat gtc<br>Gln Thr Pro Leu Gly Ala Ile Asn Thr Thr Leu Pro Phe His Asn Val<br>                   295                   300                 305 | 967 | |
| cac cca ctg aca ata ggt gag tgc ccc aaa tat gta aaa tcg gag aag<br>His Pro Leu Thr Ile Gly Glu Cys Pro Lys Tyr Val Lys Ser Glu Lys<br>     310                   315                   320 | 1015 | |
| ttg gtc tta gca aca gga cta agg aat gtt ccc cag att gaa tca aga<br>Leu Val Leu Ala Thr Gly Leu Arg Asn Val Pro Gln Ile Glu Ser Arg<br>325                   330                   335                 340 | 1063 | |
| gga ttg ttt ggg gca ata gct ggt ttt ata gaa gga gga tgg caa gga<br>Gly Leu Phe Gly Ala Ile Ala Gly Phe Ile Glu Gly Gly Trp Gln Gly<br>                   345                   350                 355 | 1111 | |
| atg att gat ggt tgg tat gga tac cat cac agc aat gac cag gga tca<br>Met Ile Asp Gly Trp Tyr Gly Tyr His His Ser Asn Asp Gln Gly Ser<br>           360                   365                   370 | 1159 | |
| ggg tat gca gca gac aaa gaa tcc act caa aag gca ttt gat gga atc<br>Gly Tyr Ala Ala Asp Lys Glu Ser Thr Gln Lys Ala Phe Asp Gly Ile<br>                   375                   380                 385 | 1207 | |
| acc aac aag gta aat tct gtg att gaa aag atg aac acc caa ttt gaa<br>Thr Asn Lys Val Asn Ser Val Ile Glu Lys Met Asn Thr Gln Phe Glu<br>     390                   395                   400 | 1255 | |
| gct gtt ggg aaa gaa ttc agt aac tta gag aga aga ctg gag aac ttg<br>Ala Val Gly Lys Glu Phe Ser Asn Leu Glu Arg Arg Leu Glu Asn Leu<br>405                   410                   415                 420 | 1303 | |
| aac aaa aag atg gaa gac ggg ttt cta gat gtg tgg aca tac aat gct<br>Asn Lys Lys Met Glu Asp Gly Phe Leu Asp Val Trp Thr Tyr Asn Ala<br>                   425                   430                 435 | 1351 | |
| gag ctt cta gtt ctg atg gaa aat gag agg aca ctt gac ttt cat gat<br>Glu Leu Leu Val Leu Met Glu Asn Glu Arg Thr Leu Asp Phe His Asp<br>           440                   445                   450 | 1399 | |
| tct aat gtc aag aat ctg tat gat aaa gtc aga atg cag ctg aga gac | 1447 | |

```
Ser Asn Val Lys Asn Leu Tyr Asp Lys Val Arg Met Gln Leu Arg Asp
        455                 460                 465 aac gtc aaa gaa cta gga aat gga tgt ttt gaa ttt tat cac aaa tgt      1495
Asn Val Lys Glu Leu Gly Asn Gly Cys Phe Glu Phe Tyr His Lys Cys
        470                 475                 480 gat gat gaa tgc atg aat agt gtg aaa aac ggg acg tat gat tat ccc      1543
Asp Asp Glu Cys Met Asn Ser Val Lys Asn Gly Thr Tyr Asp Tyr Pro
485                 490                 495                 500 aag tat gaa gaa gag tct aaa cta aat aga aat gaa atc aaa ggg gta      1591
Lys Tyr Glu Glu Glu Ser Lys Leu Asn Arg Asn Glu Ile Lys Gly Val
            505                 510                 515 aaa ttg agc agc atg ggg gtt tat caa atc ctt gcc att tat gct aca      1639
Lys Leu Ser Ser Met Gly Val Tyr Gln Ile Leu Ala Ile Tyr Ala Thr
        520                 525                 530 gta gca ggt tct ctg tca ctg gca atc atg atg gct ggg atc tct ttc      1687
Val Ala Gly Ser Leu Ser Leu Ala Ile Met Met Ala Gly Ile Ser Phe
    535                 540                 545 tgg atg tgc tcc aac ggg tct ctg cag tgc agg atc tgc ata tga          1732
Trp Met Cys Ser Asn Gly Ser Leu Gln Cys Arg Ile Cys Ile
550                 555                 560 ttataagtca ttttataatt aaaaacactc ttgtttctac t                        1773

<210> SEQ ID NO 8
<211> LENGTH: 562
<212> TYPE: PRT
<213> ORGANISM: Influenza A virus

<400> SEQUENCE: 8

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Glu Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Lys Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Ser Arg Met
```

```
                225                 230                 235                 240
Glu Phe Ser Trp Thr Leu Leu Asp Met Trp Asp Thr Ile Asn Phe Glu
                245                 250                 255
Ser Thr Gly Asn Leu Ile Ala Pro Glu Tyr Gly Phe Lys Ile Ser Lys
            260                 265                 270
Arg Gly Ser Ser Gly Ile Met Lys Thr Glu Gly Thr Leu Glu Asn Cys
        275                 280                 285
Glu Thr Lys Cys Gln Thr Pro Leu Gly Ala Ile Asn Thr Thr Leu Pro
    290                 295                 300
Phe His Asn Val His Pro Leu Thr Ile Gly Glu Cys Pro Lys Tyr Val
305                 310                 315                 320
Lys Ser Glu Lys Leu Val Leu Ala Thr Gly Leu Arg Asn Val Pro Gln
                325                 330                 335
Ile Glu Ser Arg Gly Leu Phe Gly Ala Ile Ala Gly Phe Ile Glu Gly
            340                 345                 350
Gly Trp Gln Gly Met Ile Asp Gly Trp Tyr Gly Tyr His His Ser Asn
        355                 360                 365
Asp Gln Gly Ser Gly Tyr Ala Ala Asp Lys Glu Ser Thr Gln Lys Ala
    370                 375                 380
Phe Asp Gly Ile Thr Asn Lys Val Asn Ser Val Ile Glu Lys Met Asn
385                 390                 395                 400
Thr Gln Phe Glu Ala Val Gly Lys Glu Phe Ser Asn Leu Glu Arg Arg
                405                 410                 415
Leu Glu Asn Leu Asn Lys Lys Met Glu Asp Gly Phe Leu Asp Val Trp
            420                 425                 430
Thr Tyr Asn Ala Glu Leu Leu Val Leu Met Glu Asn Glu Arg Thr Leu
        435                 440                 445
Asp Phe His Asp Ser Asn Val Lys Asn Leu Tyr Asp Lys Val Arg Met
    450                 455                 460
Gln Leu Arg Asp Asn Val Lys Glu Leu Gly Asn Gly Cys Phe Glu Phe
465                 470                 475                 480
Tyr His Lys Cys Asp Asp Glu Cys Met Asn Ser Val Lys Asn Gly Thr
                485                 490                 495
Tyr Asp Tyr Pro Lys Tyr Glu Glu Glu Ser Lys Leu Asn Arg Asn Glu
            500                 505                 510
Ile Lys Gly Val Lys Leu Ser Ser Met Gly Val Tyr Gln Ile Leu Ala
        515                 520                 525
Ile Tyr Ala Thr Val Ala Gly Ser Leu Ser Leu Ala Ile Met Met Ala
    530                 535                 540
Gly Ile Ser Phe Trp Met Cys Ser Asn Gly Ser Leu Gln Cys Arg Ile
545                 550                 555                 560
Cys Ile

<210> SEQ ID NO 9
<211> LENGTH: 1765
<212> TYPE: DNA
<213> ORGANISM: Influenza A virus
<220> FEATURE:
<221> NAME/KEY: CDS
<222> LOCATION: (30)..(1730)
<223> OTHER INFORMATION:

<400> SEQUENCE: 9
agcaaaagca ggggatactt tcattaatc atg aag acc gtt att gct tta agc      53
                                 Met Lys Thr Val Ile Ala Leu Ser
                                  1               5
```

-continued

| | | |
|---|---|---|
| tac att ctc tgt ctg act ttc gga cag gac ctc cca ggg aat gac aac<br>Tyr Ile Leu Cys Leu Thr Phe Gly Gln Asp Leu Pro Gly Asn Asp Asn<br>　 10　　　　　　　 15　　　　　　　　 20 | | 101 |
| agt aca gca aca ctg tgc ctg ggg cac cat gca gtg ccg aat ggg aca<br>Ser Thr Ala Thr Leu Cys Leu Gly His His Ala Val Pro Asn Gly Thr<br>25　　　　　　　 30　　　　　　　 35　　　　　　　　 40 | | 149 |
| ata gtg aag aca atc aca gat gat cag att gag gtg act aat gct act<br>Ile Val Lys Thr Ile Thr Asp Asp Gln Ile Glu Val Thr Asn Ala Thr<br>　　　　　　 45　　　　　　　 50　　　　　　　　 55 | | 197 |
| gag cta gtt caa agc tcc tca aca ggg aaa ata tgc aac aat cct cac<br>Glu Leu Val Gln Ser Ser Ser Thr Gly Lys Ile Cys Asn Asn Pro His<br>　　　　 60　　　　　　　 65　　　　　　　　 70 | | 245 |
| agg atc ctt gat gga agg gcc tgc aca tta ata gat gct cta ctg ggg<br>Arg Ile Leu Asp Gly Arg Ala Cys Thr Leu Ile Asp Ala Leu Leu Gly<br>　　 75　　　　　　　 80　　　　　　　　 85 | | 293 |
| gat cct cat tgc gat gtc ttt caa aat gag acg tgg gac ctt ttt gtg<br>Asp Pro His Cys Asp Val Phe Gln Asn Glu Thr Trp Asp Leu Phe Val<br>　 90　　　　　　　 95　　　　　　　 100 | | 341 |
| gag cga agc aat gct ttc agc aac tgt tac cct tat gat ata cca gat<br>Glu Arg Ser Asn Ala Phe Ser Asn Cys Tyr Pro Tyr Asp Ile Pro Asp<br>105　　　　　　　 110　　　　　　　 115　　　　　　　　 120 | | 389 |
| tat gca tcc ctt agg tcc cta gtt gcc tca tca ggc aca ttg gag ttc<br>Tyr Ala Ser Leu Arg Ser Leu Val Ala Ser Ser Gly Thr Leu Glu Phe<br>　　　　　　 125　　　　　　　 130　　　　　　　 135 | | 437 |
| atc act gag ggt ttc acc tgg aca gga gta act cag aat gga ggg agc<br>Ile Thr Glu Gly Phe Thr Trp Thr Gly Val Thr Gln Asn Gly Gly Ser<br>　　　　　 140　　　　　　　 145　　　　　　　 150 | | 485 |
| agt gct tgc aaa aga gga cct gct aac ggt ttc ttc agt aga ctg aac<br>Ser Ala Cys Lys Arg Gly Pro Ala Asn Gly Phe Phe Ser Arg Leu Asn<br>　　　　 155　　　　　　　 160　　　　　　　 165 | | 533 |
| tgg ttg act aaa tca gaa agc gca tac cca gtg ctg aac gtg act atg<br>Trp Leu Thr Lys Ser Glu Ser Ala Tyr Pro Val Leu Asn Val Thr Met<br>　　 170　　　　　　　 175　　　　　　　 180 | | 581 |
| cca aat aat gac aat ttt gac aaa cta tac atc tgg gga gta cac cac<br>Pro Asn Asn Asp Asn Phe Asp Lys Leu Tyr Ile Trp Gly Val His His<br>185　　　　　　　 190　　　　　　　 195　　　　　　　　 200 | | 629 |
| ccg agc aca aat caa gaa caa acc aac ctg tat gtt caa gca tca ggg<br>Pro Ser Thr Asn Gln Glu Gln Thr Asn Leu Tyr Val Gln Ala Ser Gly<br>　　　　　　 205　　　　　　　 210　　　　　　　 215 | | 677 |
| aga gtc aca gtc tct acc agg aga agt cag cag act ata atc ccg aat<br>Arg Val Thr Val Ser Thr Arg Arg Ser Gln Gln Thr Ile Ile Pro Asn<br>　　　　　 220　　　　　　　 225　　　　　　　 230 | | 725 |
| att gga tct aga ccc tgg gta agg ggc cag cct ggc aga ata agc atc<br>Ile Gly Ser Arg Pro Trp Val Arg Gly Gln Pro Gly Arg Ile Ser Ile<br>　　　　 235　　　　　　　 240　　　　　　　 245 | | 773 |
| tat tgg aca ata gtt aaa cct ggg gac gtg ctg gta atc aac agt aat<br>Tyr Trp Thr Ile Val Lys Pro Gly Asp Val Leu Val Ile Asn Ser Asn<br>　　 250　　　　　　　 255　　　　　　　 260 | | 821 |
| gga aac cta atc gct cct cgg ggt tac ttc aag atg cgc act ggg aaa<br>Gly Asn Leu Ile Ala Pro Arg Gly Tyr Phe Lys Met Arg Thr Gly Lys<br>265　　　　　　　 270　　　　　　　 275　　　　　　　　 280 | | 869 |
| agc tca ata atg agg tca gat gca cct att gac acc tgt atc tct gag<br>Ser Ser Ile Met Arg Ser Asp Ala Pro Ile Asp Thr Cys Ile Ser Glu<br>　　　　　　 285　　　　　　　 290　　　　　　　 295 | | 917 |
| tgc atc act cca aat gga agc att ccc aat gac aag ccc ttc caa aat<br>Cys Ile Thr Pro Asn Gly Ser Ile Pro Asn Asp Lys Pro Phe Gln Asn<br>　　　　　 300　　　　　　　 305　　　　　　　 310 | | 965 |
| gta aac aag atc aca tac gga gca tgt ccc aag tat gtt aag cag aac<br>Val Asn Lys Ile Thr Tyr Gly Ala Cys Pro Lys Tyr Val Lys Gln Asn<br>　　　　 315　　　　　　　 320　　　　　　　 325 | | 1013 |

```
acc ctg aag ttg gca aca ggg atg cgg aat gta cca gag aaa caa acc    1061
Thr Leu Lys Leu Ala Thr Gly Met Arg Asn Val Pro Glu Lys Gln Thr
    330                 335                 340 aga ggc cta ttc ggt gca ata gca ggt ttt ata gaa aat gga tgg gag    1109
Arg Gly Leu Phe Gly Ala Ile Ala Gly Phe Ile Glu Asn Gly Trp Glu
345                 350                 355                 360 gga atg ata gat ggc tgg tat ggc ttc agg cat caa aat tct gag ggt    1157
Gly Met Ile Asp Gly Trp Tyr Gly Phe Arg His Gln Asn Ser Glu Gly
                365                 370                 375 aca gga caa gca gca gac ctt aaa agc act cag gca gcc att gac caa    1205
Thr Gly Gln Ala Ala Asp Leu Lys Ser Thr Gln Ala Ala Ile Asp Gln
            380                 385                 390 atc aat agg aaa ttg aac aga gtg att gaa aag acg aat gag aag ttc    1253
Ile Asn Arg Lys Leu Asn Arg Val Ile Glu Lys Thr Asn Glu Lys Phe
        395                 400                 405 cat caa atc gaa aag gaa ttc tcc gaa gta gaa ggg agg att cag gac    1301
His Gln Ile Glu Lys Glu Phe Ser Glu Val Glu Gly Arg Ile Gln Asp
    410                 415                 420 ctt gag aaa tac gtt gaa gac acg aaa ata gat ctc tgg tct tac aat    1349
Leu Glu Lys Tyr Val Glu Asp Thr Lys Ile Asp Leu Trp Ser Tyr Asn
425                 430                 435                 440 gcg gaa ctt ctt gtt gcc cta gag aat cag cat aca atc gat ctg gct    1397
Ala Glu Leu Leu Val Ala Leu Glu Asn Gln His Thr Ile Asp Leu Ala
                445                 450                 455 gat tca gaa atg aac aaa tta ttt gaa aaa acc agg agg caa ctg agg    1445
Asp Ser Glu Met Asn Lys Leu Phe Glu Lys Thr Arg Arg Gln Leu Arg
            460                 465                 470 gaa aat gct gaa gac atg ggc aat ggt tgt ttc aag ata tac cac aaa    1493
Glu Asn Ala Glu Asp Met Gly Asn Gly Cys Phe Lys Ile Tyr His Lys
        475                 480                 485 tgt gac aat gct tgc ata gag tca att aga aac ggg act tat gat cat    1541
Cys Asp Asn Ala Cys Ile Glu Ser Ile Arg Asn Gly Thr Tyr Asp His
    490                 495                 500 gat ata tac aga gac gag gca ttg aac aac cgg ttc cag atc aaa ggt    1589
Asp Ile Tyr Arg Asp Glu Ala Leu Asn Asn Arg Phe Gln Ile Lys Gly
505                 510                 515                 520 gtc gaa cta aaa tct gga tac aaa gac tgg atc ctg tgg att tcc ttt    1637
Val Glu Leu Lys Ser Gly Tyr Lys Asp Trp Ile Leu Trp Ile Ser Phe
                525                 530                 535 gcc ata tca tgc ctt ttg ctt tgt gtt gtt ttg ctg ggt ttc att atg    1685
Ala Ile Ser Cys Leu Leu Leu Cys Val Val Leu Leu Gly Phe Ile Met
            540                 545                 550 tgg gcc tgc cag aga ggc aac att agg tgc aac att tgc att tga       1730
Trp Ala Cys Gln Arg Gly Asn Ile Arg Cys Asn Ile Cys Ile
        555                 560                 565 gtatactaat gattaaaaac acccttgttt ctact                            1765

<210> SEQ ID NO 10
<211> LENGTH: 566
<212> TYPE: PRT
<213> ORGANISM: Influenza A virus

<400> SEQUENCE: 10

Met Lys Thr Val Ile Ala Leu Ser Tyr Ile Leu Cys Leu Thr Phe Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asp Asp
        35                  40                  45

Gln Ile Glu Val Thr Asn Ala Thr Glu Leu Val Gln Ser Ser Ser Thr
```

```
                50                  55                  60
Gly Lys Ile Cys Asn Asn Pro His Arg Ile Leu Asp Gly Arg Ala Cys
 65                  70                  75                  80

Thr Leu Ile Asp Ala Leu Leu Gly Asp Pro His Cys Asp Val Phe Gln
                 85                  90                  95

Asn Glu Thr Trp Asp Leu Phe Val Glu Arg Ser Asn Ala Phe Ser Asn
                100                 105                 110

Cys Tyr Pro Tyr Asp Ile Pro Asp Tyr Ala Ser Leu Arg Ser Leu Val
                115                 120                 125

Ala Ser Ser Gly Thr Leu Glu Phe Ile Thr Glu Gly Phe Thr Trp Thr
130                 135                 140

Gly Val Thr Gln Asn Gly Gly Ser Ser Ala Cys Lys Arg Gly Pro Ala
145                 150                 155                 160

Asn Gly Phe Phe Ser Arg Leu Asn Trp Leu Thr Lys Ser Glu Ser Ala
                165                 170                 175

Tyr Pro Val Leu Asn Val Thr Met Pro Asn Asn Asp Asn Phe Asp Lys
                180                 185                 190

Leu Tyr Ile Trp Gly Val His His Pro Ser Thr Asn Gln Glu Gln Thr
                195                 200                 205

Asn Leu Tyr Val Gln Ala Ser Gly Arg Val Thr Val Ser Thr Arg Arg
210                 215                 220

Ser Gln Gln Thr Ile Ile Pro Asn Ile Gly Ser Arg Pro Trp Val Arg
225                 230                 235                 240

Gly Gln Pro Gly Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
                260                 265                 270

Tyr Phe Lys Met Arg Thr Gly Lys Ser Ser Ile Met Arg Ser Asp Ala
                275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
                340                 345                 350

Gly Phe Ile Glu Asn Gly Trp Glu Gly Met Ile Asp Gly Trp Tyr Gly
                355                 360                 365

Phe Arg His Gln Asn Ser Glu Gly Thr Gly Gln Ala Ala Asp Leu Lys
                370                 375                 380

Ser Thr Gln Ala Ala Ile Asp Gln Ile Asn Arg Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Ala Asp Ser Glu Met Asn Lys Leu Phe
                450                 455                 460

Glu Lys Thr Arg Arg Gln Leu Arg Glu Asn Ala Glu Asp Met Gly Asn
465                 470                 475                 480
```

-continued

```
Gly Cys Phe Lys Ile Tyr His Lys Cys Asp Asn Ala Cys Ile Glu Ser
            485                 490                 495

Ile Arg Asn Gly Thr Tyr Asp His Asp Ile Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Leu Leu Leu Cys
            530                 535                 540

Val Val Leu Leu Gly Phe Ile Met Trp Ala Cys Gln Arg Gly Asn Ile
545                 550                 555                 560

Arg Cys Asn Ile Cys Ile
            565

<210> SEQ ID NO 11
<211> LENGTH: 1704
<212> TYPE: DNA
<213> ORGANISM: Influenza A virus
<220> FEATURE:
<221> NAME/KEY: CDS
<222> LOCATION: (6)..(1700)
<223> O

```
                    195                 200                 205
tac aag aat aac cct gga gga gtc act gtg tct acc aaa act agt caa      674
Tyr Lys Asn Asn Pro Gly Gly Val Thr Val Ser Thr Lys Thr Ser Gln
            210                 215                 220 aca agt gta gtg cct aac att ggc agc aga ccc ttg gtg aga gga caa      722
Thr Ser Val Val Pro Asn Ile Gly Ser Arg Pro Leu Val Arg Gly Gln
        225                 230                 235 agt ggc aga gta agt ttc tac tgg act att gta gag cct gga gac ttg      770
Ser Gly Arg Val Ser Phe Tyr Trp Thr Ile Val Glu Pro Gly Asp Leu
240                 245                 250                 255 ata gtc ttc aac aca ata ggg aat cta att gcc ccg aga ggg cat tac      818
Ile Val Phe Asn Thr Ile Gly Asn Leu Ile Ala Pro Arg Gly His Tyr
                260                 265                 270 aag tta aac aat cag aag aag agc aca att cta aat act gca att ccc      866
Lys Leu Asn Asn Gln Lys Lys Ser Thr Ile Leu Asn Thr Ala Ile Pro
            275                 280                 285 ata ggc tca tgt gtc agc aaa tgt cac aca gac aaa ggt tct ctc tct      914
Ile Gly Ser Cys Val Ser Lys Cys His Thr Asp Lys Gly Ser Leu Ser
        290                 295                 300 aca act aag ccc ttc caa aat atc tcg agg ata gca gtt gga gac tgc      962
Thr Thr Lys Pro Phe Gln Asn Ile Ser Arg Ile Ala Val Gly Asp Cys
305                 310                 315 ccc aga tat gtc aaa cag ggc tct cta aaa ctt gca aca ggg atg agg     1010
Pro Arg Tyr Val Lys Gln Gly Ser Leu Lys Leu Ala Thr Gly Met Arg
320                 325                 330                 335 aac att cct gaa aag gca tca aga ggg ctt ttt gga gca ata gct ggg     1058
Asn Ile Pro Glu Lys Ala Ser Arg Gly Leu Phe Gly Ala Ile Ala Gly
                340                 345                 350 ttc ata gag aat ggc tgg caa ggt cta atc gat ggt tgg tat gga ttc     1106
Phe Ile Glu Asn Gly Trp Gln Gly Leu Ile Asp Gly Trp Tyr Gly Phe
            355                 360                 365 aga cac cag aat gca gaa gga aca gga aca gcg gca gat ctc aaa tcc     1154
Arg His Gln Asn Ala Glu Gly Thr Gly Thr Ala Ala Asp Leu Lys Ser
        370                 375                 380 act cag gca gcc att gat caa atc aat ggg aaa ctt aac cgt ctt att     1202
Thr Gln Ala Ala Ile Asp Gln Ile Asn Gly Lys Leu Asn Arg Leu Ile
385                 390                 395 gag aag aca aac gat aaa tac cat caa atc gaa aaa gag ttc gag caa     1250
Glu Lys Thr Asn Asp Lys Tyr His Gln Ile Glu Lys Glu Phe Glu Gln
400                 405                 410                 415 gtt gaa gga aga att caa gat ctg gaa aag tat gtt gag gac aca aag     1298
Val Glu Gly Arg Ile Gln Asp Leu Glu Lys Tyr Val Glu Asp Thr Lys
                420                 425                 430 att gat tta tgg tca tat aat gca gag cta tta gtc gct cta gaa aac     1346
Ile Asp Leu Trp Ser Tyr Asn Ala Glu Leu Leu Val Ala Leu Glu Asn
            435                 440                 445 caa cac act ata gac gtg act gat tca gaa atg aac aaa ctc ttt gaa     1394
Gln His Thr Ile Asp Val Thr Asp Ser Glu Met Asn Lys Leu Phe Glu
        450                 455                 460 aga gta agg cgt caa ctc aga gag aat gct gaa gac aaa gga aat ggg     1442
Arg Val Arg Arg Gln Leu Arg Glu Asn Ala Glu Asp Lys Gly Asn Gly
465                 470                 475 tgt ttc gaa ata ttc cac aag tgt gat aac aac tgc att gaa agt att     1490
Cys Phe Glu Ile Phe His Lys Cys Asp Asn Asn Cys Ile Glu Ser Ile
480                 485                 490                 495 cgg aat ggg act tat gat cat gat att tat aga gat gaa gca atc aac     1538
Arg Asn Gly Thr Tyr Asp His Asp Ile Tyr Arg Asp Glu Ala Ile Asn
                500                 505                 510 aat cga ttc caa atc cag gga gtc aaa ttg acc cag gga tat atg gac     1586
Asn Arg Phe Gln Ile Gln Gly Val Lys Leu Thr Gln Gly Tyr Met Asp
```

```
                515                 520                 525
atc att ctt tgg att tca ttc tcc ata tca tgc ttt ttg ctc gta gca      1634
Ile Ile Leu Trp Ile Ser Phe Ser Ile Ser Cys Phe Leu Leu Val Ala
        530                 535                 540 cta ctt tta gcc ttc att ttg tgg gct tgt cag aac gga aac atc cgg      1682
Leu Leu Leu Ala Phe Ile Leu Trp Ala Cys Gln Asn Gly Asn Ile Arg
545                 550                 555 tgc cag att tgt att tag agaa                                         1704
Cys Gln Ile Cys Ile
560

<210> SEQ ID NO 12
<211> LENGTH: 564
<212> TYPE: PRT
<213> ORGANISM: Influenza A virus

<400> SEQUENCE: 12

Met Leu Ser Ile Val Ile Leu Phe Leu Leu Ile Ala Glu Asn Ser Ser
1               5                   10                  15

Gln Asn Tyr Thr Gly Asn Pro Val Ile Cys Met Gly His His Ala Val
            20                  25                  30

Ala Asn Gly Thr Met Val Lys Thr Leu Ala Asp Asp Gln Val Glu Val
        35                  40                  45

Val Thr Ala Gln Glu Leu Val Glu Ser Gln Asn Leu Pro Glu Leu Cys
    50                  55                  60

Pro Ser Pro Leu Arg Leu Val Asp Gly Gln Thr Cys Asp Ile Ile Asn
65                  70                  75                  80

Gly Ala Leu Gly Ser Pro Gly Cys Asp His Leu Asn Gly Ala Glu Trp
                85                  90                  95

Asp Val Phe Ile Glu Arg Pro Asn Ala Val Asp Thr Cys Tyr Pro Phe
            100                 105                 110

Asp Val Pro Glu Tyr Gln Ser Leu Arg Ser Ile Leu Ala Asn Asn Gly
        115                 120                 125

Lys Phe Glu Phe Ile Ala Glu Glu Phe Gln Trp Asn Thr Val Lys Gln
    130                 135                 140

Asn Gly Lys Ser Gly Ala Cys Lys Arg Ala Asn Val Asn Asp Phe Phe
145                 150                 155                 160

Asn Arg Leu Asn Trp Leu Val Lys Ser Asp Gly Asn Ala Tyr Pro Leu
                165                 170                 175

Gln Asn Leu Thr Lys Ile Asn Asn Gly Asp Tyr Ala Arg Leu Tyr Ile
            180                 185                 190

Trp Gly Val His His Pro Ser Thr Asp Thr Glu Gln Thr Asn Leu Tyr
        195                 200                 205

Lys Asn Asn Pro Gly Gly Val Thr Val Ser Thr Lys Thr Ser Gln Thr
    210                 215                 220

Ser Val Val Pro Asn Ile Gly Ser Arg Pro Leu Val Arg Gly Gln Ser
225                 230                 235                 240

Gly Arg Val Ser Phe Tyr Trp Thr Ile Val Glu Pro Gly Asp Leu Ile
                245                 250                 255

Val Phe Asn Thr Ile Gly Asn Leu Ile Ala Pro Arg Gly His Tyr Lys
            260                 265                 270

Leu Asn Asn Gln Lys Lys Ser Thr Ile Leu Asn Thr Ala Ile Pro Ile
        275                 280                 285

Gly Ser Cys Val Ser Lys Cys His Thr Asp Lys Gly Ser Leu Ser Thr
    290                 295                 300

Thr Lys Pro Phe Gln Asn Ile Ser Arg Ile Ala Val Gly Asp Cys Pro
```

```
                 305                 310                 315                 320
Arg Tyr Val Lys Gln Gly Ser Leu Lys Leu Ala Thr Gly Met Arg Asn
                325                 330                 335

Ile Pro Glu Lys Ala Ser Arg Gly Leu Phe Gly Ala Ile Ala Gly Phe
            340                 345                 350

Ile Glu Asn Gly Trp Gln Gly Leu Ile Asp Gly Trp Tyr Gly Phe Arg
        355                 360                 365

His Gln Asn Ala Glu Gly Thr Gly Thr Ala Ala Asp Leu Lys Ser Thr
    370                 375                 380

Gln Ala Ala Ile Asp Gln Ile Asn Gly Lys Leu Asn Arg Leu Ile Glu
385                 390                 395                 400

Lys Thr Asn Asp Lys Tyr His Gln Ile Glu Lys Glu Phe Glu Gln Val
                405                 410                 415

Glu Gly Arg Ile Gln Asp Leu Glu Lys Tyr Val Glu Asp Thr Lys Ile
            420                 425                 430

Asp Leu Trp Ser Tyr Asn Ala Glu Leu Leu Val Ala Leu Glu Asn Gln
        435                 440                 445

His Thr Ile Asp Val Thr Asp Ser Glu Met Asn Lys Leu Phe Glu Arg
    450                 455                 460

Val Arg Arg Gln Leu Arg Glu Asn Ala Glu Asp Lys Gly Asn Gly Cys
465                 470                 475                 480

Phe Glu Ile Phe His Lys Cys Asp Asn Asn Cys Ile Glu Ser Ile Arg
                485                 490                 495

Asn Gly Thr Tyr Asp His Asp Ile Tyr Arg Asp Glu Ala Ile Asn Asn
            500                 505                 510

Arg Phe Gln Ile Gln Gly Val Lys Leu Thr Gln Gly Tyr Met Asp Ile
        515                 520                 525

Ile Leu Trp Ile Ser Phe Ser Ile Ser Cys Phe Leu Leu Val Ala Leu
    530                 535                 540

Leu Leu Ala Phe Ile Leu Trp Ala Cys Gln Asn Gly Asn Ile Arg Cys
545                 550                 555                 560

Gln Ile Cys Ile

<210> SEQ ID NO 13
<211> LENGTH: 1634
<212> TYPE: DNA
<213> ORGANISM: Influenza A virus
<220> FEATURE:
<221> NAME/KEY: CDS
<222> LOCATION: (3)..(1634)
<223> OTHER INFORMATION:
<220> FEATURE:
<221> NAME/KEY: misc_feature
<222> LOCATION: (1634)..(1634)
<223> OTHER INFORMATION: n is unknown base

<400> SEQUENCE: 13 ag aaa ata gtg ctt ctt ctt gca aca gtc agt ctt gtt aaa agt gac      47
   Lys Ile Val Leu Leu Leu Ala Thr Val Ser Leu Val Lys Ser Asp
   1               5                  10                  15 cag att tgc att ggt tac cat gca aac aac tcg aca gaa cag gtt gac      95
Gln Ile Cys Ile Gly Tyr His Ala Asn Asn Ser Thr Glu Gln Val Asp
            20                  25                  30 aca ata atg gaa aag aat gtc act gtt aca cat gcc caa gac ata ttg     143
Thr Ile Met Glu Lys Asn Val Thr Val Thr His Ala Gln Asp Ile Leu
        35                  40                  45 gaa aag aca cac aac ggg aag ctc tgc agt cta aat gga gtg aag cct     191
Glu Lys Thr His Asn Gly Lys Leu Cys Ser Leu Asn Gly Val Lys Pro
    50                  55                  60
```

| | | | | | | | | | | | | | | | | |
|---|---|---|---|---|---|---|---|---|---|---|---|---|---|---|---|---|
| ctc | att | ttg | agg | gat | tgt | agt | gta | gct | gga | tgg | ctc | ctc | gga | aac | cct | 239 |
| Leu | Ile | Leu | Arg | Asp | Cys | Ser | Val | Ala | Gly | Trp | Leu | Leu | Gly | Asn | Pro | |
| | 65 | | | | 70 | | | | | 75 | | | | | | |
| atg | tgt | gac | gaa | ttc | ctc | aat | gtg | ccg | gaa | tgg | tct | tac | ata | gtg | gag | 287 |
| Met | Cys | Asp | Glu | Phe | Leu | Asn | Val | Pro | Glu | Trp | Ser | Tyr | Ile | Val | Glu | |
| 80 | | | | | 85 | | | | | 90 | | | | | 95 | |
| aag | gac | agt | cca | gtc | aat | ggc | ctc | tgc | tac | cca | gga | gat | ttc | aac | gac | 335 |
| Lys | Asp | Ser | Pro | Val | Asn | Gly | Leu | Cys | Tyr | Pro | Gly | Asp | Phe | Asn | Asp | |
| | | | | 100 | | | | | 105 | | | | | 110 | | |
| tat | gaa | gaa | ctg | aaa | cac | cta | ttg | agc | agc | aca | aac | cat | ttt | gag | aaa | 383 |
| Tyr | Glu | Glu | Leu | Lys | His | Leu | Leu | Ser | Ser | Thr | Asn | His | Phe | Glu | Lys | |
| | | | 115 | | | | | 120 | | | | | 125 | | | |
| atc | caa | atc | atc | ccc | aga | agc | tct | tgg | tcc | aat | cat | gat | gcc | tca | tca | 431 |
| Ile | Gln | Ile | Ile | Pro | Arg | Ser | Ser | Trp | Ser | Asn | His | Asp | Ala | Ser | Ser | |
| | | 130 | | | | | 135 | | | | | 140 | | | | |
| gga | gtg | agc | tct | gca | tgt | cca | tat | ggt | ggg | agg | tcc | tcc | ttt | ttc | aga | 479 |
| Gly | Val | Ser | Ser | Ala | Cys | Pro | Tyr | Gly | Gly | Arg | Ser | Ser | Phe | Phe | Arg | |
| 145 | | | | | 150 | | | | | 155 | | | | | | |
| aat | gtg | gta | tgg | ctt | atc | aaa | aag | aac | aat | gca | tac | cca | aca | ata | aag | 527 |
| Asn | Val | Val | Trp | Leu | Ile | Lys | Lys | Asn | Asn | Ala | Tyr | Pro | Thr | Ile | Lys | |
| 160 | | | | | 165 | | | | | 170 | | | | | 175 | |
| agg | agt | tac | aat | aat | acc | aac | caa | gaa | gat | ctt | ttg | ata | ctg | tgg | ggg | 575 |
| Arg | Ser | Tyr | Asn | Asn | Thr | Asn | Gln | Glu | Asp | Leu | Leu | Ile | Leu | Trp | Gly | |
| | | | | 180 | | | | | 185 | | | | | 190 | | |
| att | cac | cat | cct | aat | gat | gcg | gca | gag | cag | aca | aaa | ctc | tat | caa | aac | 623 |
| Ile | His | His | Pro | Asn | Asp | Ala | Ala | Glu | Gln | Thr | Lys | Leu | Tyr | Gln | Asn | |
| | | | 195 | | | | | 200 | | | | | 205 | | | |
| cca | act | acc | tat | gtt | tcc | gtt | gga | aca | tca | aca | ctg | aac | cag | aga | tcg | 671 |
| Pro | Thr | Thr | Tyr | Val | Ser | Val | Gly | Thr | Ser | Thr | Leu | Asn | Gln | Arg | Ser | |
| | | 210 | | | | | 215 | | | | | 220 | | | | |
| gtt | cca | gaa | ata | gct | act | agg | ccc | aaa | gtg | aac | ggg | caa | agt | gga | aga | 719 |
| Val | Pro | Glu | Ile | Ala | Thr | Arg | Pro | Lys | Val | Asn | Gly | Gln | Ser | Gly | Arg | |
| 225 | | | | | 230 | | | | | 235 | | | | | | |
| atg | gag | ttc | ttc | tgg | aca | att | tta | aag | ccg | aat | gat | gcc | atc | aat | ttc | 767 |
| Met | Glu | Phe | Phe | Trp | Thr | Ile | Leu | Lys | Pro | Asn | Asp | Ala | Ile | Asn | Phe | |
| 240 | | | | | 245 | | | | | 250 | | | | | 255 | |
| gag | agt | aat | gga | aat | ttc | att | gct | cca | gaa | tat | gca | tac | aaa | att | gtc | 815 |
| Glu | Ser | Asn | Gly | Asn | Phe | Ile | Ala | Pro | Glu | Tyr | Ala | Tyr | Lys | Ile | Val | |
| | | | | 260 | | | | | 265 | | | | | 270 | | |
| aaa | aaa | gga | gac | tca | gca | atc | atg | aaa | agt | gga | ttg | gaa | tat | ggt | aac | 863 |
| Lys | Lys | Gly | Asp | Ser | Ala | Ile | Met | Lys | Ser | Gly | Leu | Glu | Tyr | Gly | Asn | |
| | | | 275 | | | | | 280 | | | | | 285 | | | |
| tgc | aac | acc | aag | tgt | caa | act | cca | atg | ggt | gcg | ata | aac | tct | agt | atg | 911 |
| Cys | Asn | Thr | Lys | Cys | Gln | Thr | Pro | Met | Gly | Ala | Ile | Asn | Ser | Ser | Met | |
| | | 290 | | | | | 295 | | | | | 300 | | | | |
| cca | ttc | cat | aac | ata | cac | cct | ctc | acc | att | gga | gaa | tgc | ccc | aaa | tac | 959 |
| Pro | Phe | His | Asn | Ile | His | Pro | Leu | Thr | Ile | Gly | Glu | Cys | Pro | Lys | Tyr | |
| 305 | | | | | 310 | | | | | 315 | | | | | | |
| gtg | aaa | tca | gat | aga | tta | gtc | ctt | gcg | act | gga | ctc | aga | aat | gtc | cct | 1007 |
| Val | Lys | Ser | Asp | Arg | Leu | Val | Leu | Ala | Thr | Gly | Leu | Arg | Asn | Val | Pro | |
| 320 | | | | 325 | | | | | 330 | | | | | 335 | | |
| caa | aga | gaa | aca | aga | gga | cta | ttt | ggg | gct | ata | gct | ggc | ttt | ata | gag | 1055 |
| Gln | Arg | Glu | Thr | Arg | Gly | Leu | Phe | Gly | Ala | Ile | Ala | Gly | Phe | Ile | Glu | |
| | | | | 340 | | | | | 345 | | | | | 350 | | |
| gga | gga | tgg | caa | gga | atg | gta | gac | ggt | tgg | tat | ggg | tac | cac | cat | agc | 1103 |
| Gly | Gly | Trp | Gln | Gly | Met | Val | Asp | Gly | Trp | Tyr | Gly | Tyr | His | His | Ser | |
| | | | 355 | | | | | 360 | | | | | 365 | | | |
| aac | gag | cag | ggg | agt | gga | tac | gct | gca | gac | aaa | gaa | tcc | act | caa | aag | 1151 |
| Asn | Glu | Gln | Gly | Ser | Gly | Tyr | Ala | Ala | Asp | Lys | Glu | Ser | Thr | Gln | Lys | |
| | 370 | | | | | 375 | | | | | 380 | | | | | |

-continued

```
gca ata gat gga atc act aat aag gtc aac tca atc att gac aaa atg      1199
Ala Ile Asp Gly Ile Thr Asn Lys Val Asn Ser Ile Ile Asp Lys Met
    385                 390                 395 aac act cag ttt gag gct gtt gga aag gaa ttt aat aac ttg gaa agg      1247
Asn Thr Gln Phe Glu Ala Val Gly Lys Glu Phe Asn Asn Leu Glu Arg
400                 405                 410                 415 agg ata gag aat ttg aac aag aaa atg gaa gac ggg ttt cta gat gtc      1295
Arg Ile Glu Asn Leu Asn Lys Lys Met Glu Asp Gly Phe Leu Asp Val
                420                 425                 430 tgg act tat aat gct gaa ctt ctg gtt ctc atg gaa aat gag aga acc      1343
Trp Thr Tyr Asn Ala Glu Leu Leu Val Leu Met Glu Asn Glu Arg Thr
            435                 440                 445 cta gac ttt cat gac tca aat gtc aag aac ctt tat gac aag gtt cga      1391
Leu Asp Phe His Asp Ser Asn Val Lys Asn Leu Tyr Asp Lys Val Arg
        450                 455                 460 cta cag ctt agg gat aat gca aag gag ctg ggt aat ggt tgt ttc gag      1439
Leu Gln Leu Arg Asp Asn Ala Lys Glu Leu Gly Asn Gly Cys Phe Glu
    465                 470                 475 ttc tac cac aaa tgt gat aat gaa tgt atg gaa agt gta aaa aac ggg      1487
Phe Tyr His Lys Cys Asp Asn Glu Cys Met Glu Ser Val Lys Asn Gly
480                 485                 490                 495 acg tat gac tac ccg cag tat tca gaa gag gca aga cta aac aga gag      1535
Thr Tyr Asp Tyr Pro Gln Tyr Ser Glu Glu Ala Arg Leu Asn Arg Glu
                500                 505                 510 gaa ata agt gga gtg aaa ttg gaa tca atg gga act tac caa ata ctg      1583
Glu Ile Ser Gly Val Lys Leu Glu Ser Met Gly Thr Tyr Gln Ile Leu
            515                 520                 525 tca att tat tca aca gtg gcg agt tcc cta gca ctg gca atc atg gta      1631
Ser Ile Tyr Ser Thr Val Ala Ser Ser Leu Ala Leu Ala Ile Met Val
        530                 535                 540 gcn                                                                  1634
Ala

<210> SEQ ID NO 14
<211> LENGTH: 544
<212> TYPE: PRT
<213> ORGANISM: Influenza A virus
<400> SEQUENCE: 14

Lys Ile Val Leu Leu Leu Ala Thr Val Ser Leu Val Lys Ser Asp Gln
1               5                   10                  15

Ile Cys Ile Gly Tyr His Ala Asn Asn Ser Thr Glu Gln Val Asp Thr
            20                  25                  30

Ile Met Glu Lys Asn Val Thr Val Thr His Ala Gln Asp Ile Leu Glu
        35                  40                  45

Lys Thr His Asn Gly Lys Leu Cys Ser Leu Asn Gly Val Lys Pro Leu
    50                  55                  60

Ile Leu Arg Asp Cys Ser Val Ala Gly Trp Leu Leu Gly Asn Pro Met
65                  70                  75                  80

Cys Asp Glu Phe Leu Asn Val Pro Glu Trp Ser Tyr Ile Val Glu Lys
                85                  90                  95

Asp Ser Pro Val Asn Gly Leu Cys Tyr Pro Gly Asp Phe Asn Asp Tyr
            100                 105                 110

Glu Glu Leu Lys His Leu Leu Ser Ser Thr Asn His Phe Glu Lys Ile
        115                 120                 125

Gln Ile Ile Pro Arg Ser Ser Trp Ser Asn His Asp Ala Ser Ser Gly
    130                 135                 140

Val Ser Ser Ala Cys Pro Tyr Gly Gly Arg Ser Ser Phe Phe Arg Asn
```

```
            145                 150                 155                 160
        Val Val Trp Leu Ile Lys Lys Asn Asn Ala Tyr Pro Thr Ile Lys Arg
                        165                 170                 175

Ser Tyr Asn Asn Thr Asn Gln Glu Asp Leu Leu Ile Leu Trp Gly Ile
                        180                 185                 190

His His Pro Asn Asp Ala Ala Glu Gln Thr Lys Leu Tyr Gln Asn Pro
                        195                 200                 205

Thr Thr Tyr Val Ser Val Gly Thr Ser Thr Leu Asn Gln Arg Ser Val
                        210                 215                 220

Pro Glu Ile Ala Thr Arg Pro Lys Val Asn Gly Gln Ser Gly Arg Met
        225                 230                 235                 240

Glu Phe Phe Trp Thr Ile Leu Lys Pro Asn Asp Ala Ile Asn Phe Glu
                        245                 250                 255

Ser Asn Gly Asn Phe Ile Ala Pro Glu Tyr Ala Tyr Lys Ile Val Lys
                        260                 265                 270

Lys Gly Asp Ser Ala Ile Met Lys Ser Gly Leu Glu Tyr Gly Asn Cys
                        275                 280                 285

Asn Thr Lys Cys Gln Thr Pro Met Gly Ala Ile Asn Ser Ser Met Pro
        290                 295                 300

Phe His Asn Ile His Pro Leu Thr Ile Gly Glu Cys Pro Lys Tyr Val
        305                 310                 315                 320

Lys Ser Asp Arg Leu Val Leu Ala Thr Gly Leu Arg Asn Val Pro Gln
                        325                 330                 335

Arg Glu Thr Arg Gly Leu Phe Gly Ala Ile Ala Gly Phe Ile Glu Gly
                        340                 345                 350

Gly Trp Gln Gly Met Val Asp Gly Trp Tyr Gly Tyr His His Ser Asn
                        355                 360                 365

Glu Gln Gly Ser Gly Tyr Ala Ala Asp Lys Glu Ser Thr Gln Lys Ala
                        370                 375                 380

Ile Asp Gly Ile Thr Asn Lys Val Asn Ser Ile Ile Asp Lys Met Asn
        385                 390                 395                 400

Thr Gln Phe Glu Ala Val Gly Lys Glu Phe Asn Asn Leu Glu Arg Arg
                        405                 410                 415

Ile Glu Asn Leu Asn Lys Lys Met Glu Asp Gly Phe Leu Asp Val Trp
                        420                 425                 430

Thr Tyr Asn Ala Glu Leu Leu Val Leu Met Glu Asn Glu Arg Thr Leu
                        435                 440                 445

Asp Phe His Asp Ser Asn Val Lys Asn Leu Tyr Asp Lys Val Arg Leu
        450                 455                 460

Gln Leu Arg Asp Asn Ala Lys Glu Leu Gly Asn Gly Cys Phe Glu Phe
        465                 470                 475                 480

Tyr His Lys Cys Asp Asn Glu Cys Met Glu Ser Val Lys Asn Gly Thr
                        485                 490                 495

Tyr Asp Tyr Pro Gln Tyr Ser Glu Glu Ala Arg Leu Asn Arg Glu Glu
                        500                 505                 510

Ile Ser Gly Val Lys Leu Glu Ser Met Gly Thr Tyr Gln Ile Leu Ser
                        515                 520                 525

Ile Tyr Ser Thr Val Ala Ser Ser Leu Ala Leu Ala Ile Met Val Ala
                        530                 535                 540

<210> SEQ ID NO 15
<211> LENGTH: 1714
<212> TYPE: DNA
<213> ORGANISM: Influenza A virus
<220> FEATURE:
```

```
<221> NAME/KEY: CDS
<222> LOCATION: (4)..(1707)
<223> OTHER INFORMATION:

<400> SEQUENCE: 15
```

| | | | | | | | | | | | | | | | | |
|---|---|---|---|---|---|---|---|---|---|---|---|---|---|---|---|---|
| aaa | atg | att | gca | atc | ata | ata | atc | gcg | gta | gtg | gcc | tct | acc | agc | aaa | 48 |
| | Met | Ile | Ala | Ile | Ile | Ile | Ile | Ala | Val | Val | Ala | Ser | Thr | Ser | Lys | |
| | 1 | | | 5 | | | | | 10 | | | | | 15 | | |
| tca | gac | aag | atc | tgc | att | ggg | tat | cat | gcc | aac | aac | tcg | aca | aca | caa | 96 |
| Ser | Asp | Lys | Ile | Cys | Ile | Gly | Tyr | His | Ala | Asn | Asn | Ser | Thr | Thr | Gln | |
| | | | 20 | | | | | 25 | | | | | 30 | | | |
| gtg | gac | aca | ata | tta | gag | aag | aat | gtg | aca | gtg | acg | cac | tct | gta | gag | 144 |
| Val | Asp | Thr | Ile | Leu | Glu | Lys | Asn | Val | Thr | Val | Thr | His | Ser | Val | Glu | |
| | | 35 | | | | | 40 | | | | | 45 | | | | |
| ctc | cta | gaa | agt | cag | aag | gag | gag | aga | ttc | tgc | aga | gtg | ttg | aat | aaa | 192 |
| Leu | Leu | Glu | Ser | Gln | Lys | Glu | Glu | Arg | Phe | Cys | Arg | Val | Leu | Asn | Lys | |
| | 50 | | | | | 55 | | | | | 60 | | | | | |
| aca | cct | ctg | gat | cta | aag | ggt | tgc | acc | att | gaa | gga | tgg | att | ctt | gga | 240 |
| Thr | Pro | Leu | Asp | Leu | Lys | Gly | Cys | Thr | Ile | Glu | Gly | Trp | Ile | Leu | Gly | |
| 65 | | | | | 70 | | | | | 75 | | | | | | |
| aac | ccc | caa | tgt | gac | atc | tta | ctt | ggt | gac | caa | agt | tgg | tca | tac | ata | 288 |
| Asn | Pro | Gln | Cys | Asp | Ile | Leu | Leu | Gly | Asp | Gln | Ser | Trp | Ser | Tyr | Ile | |
| 80 | | | | 85 | | | | | 90 | | | | | 95 | | |
| gta | gag | agg | cct | gga | gcc | caa | aat | ggg | ata | tgt | tac | cca | ggg | gtg | ctg | 336 |
| Val | Glu | Arg | Pro | Gly | Ala | Gln | Asn | Gly | Ile | Cys | Tyr | Pro | Gly | Val | Leu | |
| | | | 100 | | | | | 105 | | | | | 110 | | | |
| aac | gaa | gtg | gaa | gaa | ctg | aaa | gca | ttc | att | ggg | tcc | gga | gag | aaa | gta | 384 |
| Asn | Glu | Val | Glu | Glu | Leu | Lys | Ala | Phe | Ile | Gly | Ser | Gly | Glu | Lys | Val | |
| | 115 | | | | | 120 | | | | | 125 | | | | | |
| cag | aga | ttt | gaa | atg | ttt | ccc | aag | agc | acg | tgg | acc | gga | gtg | gac | act | 432 |
| Gln | Arg | Phe | Glu | Met | Phe | Pro | Lys | Ser | Thr | Trp | Thr | Gly | Val | Asp | Thr | |
| | 130 | | | | | 135 | | | | | 140 | | | | | |
| aac | agt | gga | gtt | acg | aga | gct | tgc | ccc | tat | act | acc | agt | gga | tca | tcc | 480 |
| Asn | Ser | Gly | Val | Thr | Arg | Ala | Cys | Pro | Tyr | Thr | Thr | Ser | Gly | Ser | Ser | |
| | 145 | | | | | 150 | | | | | 155 | | | | | |
| ttt | tac | agg | aat | ctt | ttg | tgg | ata | ata | aaa | aca | agg | tct | gct | gca | tac | 528 |
| Phe | Tyr | Arg | Asn | Leu | Leu | Trp | Ile | Ile | Lys | Thr | Arg | Ser | Ala | Ala | Tyr | |
| 160 | | | | | 165 | | | | | 170 | | | | | 175 | |
| cca | gta | att | aag | gga | aca | tac | aat | aat | act | ggc | tcc | cag | cca | atc | cta | 576 |
| Pro | Val | Ile | Lys | Gly | Thr | Tyr | Asn | Asn | Thr | Gly | Ser | Gln | Pro | Ile | Leu | |
| | | | 180 | | | | | 185 | | | | | 190 | | | |
| tat | ttc | tgg | ggt | gtg | cat | cat | cct | cca | aat | acc | gat | gag | caa | aat | acc | 624 |
| Tyr | Phe | Trp | Gly | Val | His | His | Pro | Pro | Asn | Thr | Asp | Glu | Gln | Asn | Thr | |
| | | 195 | | | | | 200 | | | | | 205 | | | | |
| tta | tat | ggc | tct | ggt | gac | agg | tat | gtt | aga | atg | gga | act | gaa | agc | atg | 672 |
| Leu | Tyr | Gly | Ser | Gly | Asp | Arg | Tyr | Val | Arg | Met | Gly | Thr | Glu | Ser | Met | |
| | 210 | | | | | 215 | | | | | 220 | | | | | |
| aat | ttt | gcc | aag | agt | cct | gaa | ata | gca | gcc | agg | cca | gct | gtg | aat | ggg | 720 |
| Asn | Phe | Ala | Lys | Ser | Pro | Glu | Ile | Ala | Ala | Arg | Pro | Ala | Val | Asn | Gly | |
| 225 | | | | | 230 | | | | | 235 | | | | | | |
| caa | aga | gga | aga | att | gat | tat | tat | tgg | tct | gta | ctg | aaa | cca | gga | gaa | 768 |
| Gln | Arg | Gly | Arg | Ile | Asp | Tyr | Tyr | Trp | Ser | Val | Leu | Lys | Pro | Gly | Glu | |
| 240 | | | | 245 | | | | | 250 | | | | | 255 | | |
| acc | tta | aat | gta | gaa | tcc | aat | gga | aat | tta | ata | gct | cct | tgg | tat | gct | 816 |
| Thr | Leu | Asn | Val | Glu | Ser | Asn | Gly | Asn | Leu | Ile | Ala | Pro | Trp | Tyr | Ala | |
| | | | 260 | | | | | 265 | | | | | 270 | | | |
| tac | aag | ttc | aca | agt | tcc | aac | aac | aaa | gga | gct | atc | ttc | aaa | tca | aac | 864 |
| Tyr | Lys | Phe | Thr | Ser | Ser | Asn | Asn | Lys | Gly | Ala | Ile | Phe | Lys | Ser | Asn | |
| | | 275 | | | | | 280 | | | | | 285 | | | | |
| ctc | cca | att | gag | aat | tgt | gat | gct | gta | tgt | caa | act | gtt | gct | gga | gca | 912 |
| Leu | Pro | Ile | Glu | Asn | Cys | Asp | Ala | Val | Cys | Gln | Thr | Val | Ala | Gly | Ala | |

-continued

```
                    290                 295                 300
cta aag aca aac aaa act ttc caa aat gtt agt cca ctc tgg att gga       960
Leu Lys Thr Asn Lys Thr Phe Gln Asn Val Ser Pro Leu Trp Ile Gly
    305                 310                 315 gaa tgt ccc aaa tat gtt aag agt gag agc cta aga ctg gca act ggt      1008
Glu Cys Pro Lys Tyr Val Lys Ser Glu Ser Leu Arg Leu Ala Thr Gly
320                 325                 330                 335 ctg agg aat gtc cca cag gca gaa aca aga gga ttg ttt gga gcc ata      1056
Leu Arg Asn Val Pro Gln Ala Glu Thr Arg Gly Leu Phe Gly Ala Ile
                340                 345                 350 gct ggg ttt ata gaa gga ggg tgg aca ggt atg ata gac gga tgg tac      1104
Ala Gly Phe Ile Glu Gly Gly Trp Thr Gly Met Ile Asp Gly Trp Tyr
            355                 360                 365 ggg tac cat cat gag aac tca cag ggg tcg ggt tat gca gca gat aaa      1152
Gly Tyr His His Glu Asn Ser Gln Gly Ser Gly Tyr Ala Ala Asp Lys
        370                 375                 380 gaa agt acc cag aaa gca att gac ggg atc acc aat aaa gta aat tcc      1200
Glu Ser Thr Gln Lys Ala Ile Asp Gly Ile Thr Asn Lys Val Asn Ser
    385                 390                 395 atc att gac aag atg aac aca cag ttt gaa gca gta gag cat gag ttc      1248
Ile Ile Asp Lys Met Asn Thr Gln Phe Glu Ala Val Glu His Glu Phe
400                 405                 410                 415 tca aat ctc gaa agg aga ata gac aat tta aac aaa aga atg gaa gat      1296
Ser Asn Leu Glu Arg Arg Ile Asp Asn Leu Asn Lys Arg Met Glu Asp
                420                 425                 430 gga ttt ttg gat gtg tgg acg tac aat gct gaa ctt tta gtt cta ctg      1344
Gly Phe Leu Asp Val Trp Thr Tyr Asn Ala Glu Leu Leu Val Leu Leu
            435                 440                 445 gaa aat gaa agg acc ctg gat ctg cac gat gcc aat gtg aag aac cta      1392
Glu Asn Glu Arg Thr Leu Asp Leu His Asp Ala Asn Val Lys Asn Leu
        450                 455                 460 tac gag aag gtg aaa tca caa ttg aga gat aat gca aag gat ttg ggt      1440
Tyr Glu Lys Val Lys Ser Gln Leu Arg Asp Asn Ala Lys Asp Leu Gly
    465                 470                 475 aat ggg tgt ttt gaa ttt tgg cac aaa tgc gac gat gaa tgc atc aac      1488
Asn Gly Cys Phe Glu Phe Trp His Lys Cys Asp Asp Glu Cys Ile Asn
480                 485                 490                 495 tca gtt aag aat ggc aca tac gat tac cca aag tac caa gac gag agc      1536
Ser Val Lys Asn Gly Thr Tyr Asp Tyr Pro Lys Tyr Gln Asp Glu Ser
                500                 505                 510 aaa ctt aac aga cag gag ata gac tca gtg aag ctg gaa aat ctg ggc      1584
Lys Leu Asn Arg Gln Glu Ile Asp Ser Val Lys Leu Glu Asn Leu Gly
            515                 520                 525 gta tat caa att ctt gct att tat agt acg gta tcg agc agt cta gtt      1632
Val Tyr Gln Ile Leu Ala Ile Tyr Ser Thr Val Ser Ser Ser Leu Val
        530                 535                 540 ttg gtg ggg ctg atc att gcc atg ggt ctt tgg atg tgc tca aat ggc      1680
Leu Val Gly Leu Ile Ile Ala Met Gly Leu Trp Met Cys Ser Asn Gly
    545                 550                 555 tca atg caa tgc agg ata tgt ata taa ttaggaa                          1714
Ser Met Gln Cys Arg Ile Cys Ile
560                 565

<210> SEQ ID NO 16
<211> LENGTH: 567
<212> TYPE: PRT
<213> ORGANISM: Influenza A virus

<400> SEQUENCE: 16

Met Ile Ala Ile Ile Ile Ile Ala Val Val Ala Ser Thr Ser Lys Ser
1               5                   10                  15
```

-continued

```
Asp Lys Ile Cys Ile Gly Tyr His Ala Asn Asn Ser Thr Thr Gln Val
             20                  25                  30
Asp Thr Ile Leu Glu Lys Asn Val Thr Val Thr His Ser Val Glu Leu
             35                  40                  45
Leu Glu Ser Gln Lys Glu Glu Arg Phe Cys Arg Val Leu Asn Lys Thr
 50                  55                  60
Pro Leu Asp Leu Lys Gly Cys Thr Ile Glu Gly Trp Ile Leu Gly Asn
 65                  70                  75                  80
Pro Gln Cys Asp Ile Leu Leu Gly Asp Gln Ser Trp Ser Tyr Ile Val
                     85                  90                  95
Glu Arg Pro Gly Ala Gln Asn Gly Ile Cys Tyr Pro Gly Val Leu Asn
             100                 105                 110
Glu Val Glu Glu Leu Lys Ala Phe Ile Gly Ser Gly Glu Lys Val Gln
             115                 120                 125
Arg Phe Glu Met Phe Pro Lys Ser Thr Trp Thr Gly Val Asp Thr Asn
 130                 135                 140
Ser Gly Val Thr Arg Ala Cys Pro Tyr Thr Thr Ser Gly Ser Ser Phe
 145                 150                 155                 160
Tyr Arg Asn Leu Leu Trp Ile Ile Lys Thr Arg Ser Ala Ala Tyr Pro
                     165                 170                 175
Val Ile Lys Gly Thr Tyr Asn Asn Thr Gly Ser Gln Pro Ile Leu Tyr
             180                 185                 190
Phe Trp Gly Val His His Pro Pro Asn Thr Asp Glu Gln Asn Thr Leu
             195                 200                 205
Tyr Gly Ser Gly Asp Arg Tyr Val Arg Met Gly Thr Glu Ser Met Asn
 210                 215                 220
Phe Ala Lys Ser Pro Glu Ile Ala Ala Arg Pro Ala Val Asn Gly Gln
 225                 230                 235                 240
Arg Gly Arg Ile Asp Tyr Tyr Trp Ser Val Leu Lys Pro Gly Glu Thr
                     245                 250                 255
Leu Asn Val Glu Ser Asn Gly Asn Leu Ile Ala Pro Trp Tyr Ala Tyr
             260                 265                 270
Lys Phe Thr Ser Ser Asn Asn Lys Gly Ala Ile Phe Lys Ser Asn Leu
             275                 280                 285
Pro Ile Glu Asn Cys Asp Ala Val Cys Gln Thr Val Ala Gly Ala Leu
 290                 295                 300
Lys Thr Asn Lys Thr Phe Gln Asn Val Ser Pro Leu Trp Ile Gly Glu
 305                 310                 315                 320
Cys Pro Lys Tyr Val Lys Ser Glu Ser Leu Arg Leu Ala Thr Gly Leu
                     325                 330                 335
Arg Asn Val Pro Gln Ala Glu Thr Arg Gly Leu Phe Gly Ala Ile Ala
             340                 345                 350
Gly Phe Ile Glu Gly Gly Trp Thr Gly Met Ile Asp Gly Trp Tyr Gly
             355                 360                 365
Tyr His His Glu Asn Ser Gln Gly Ser Gly Tyr Ala Ala Asp Lys Glu
 370                 375                 380
Ser Thr Gln Lys Ala Ile Asp Gly Ile Thr Asn Lys Val Asn Ser Ile
 385                 390                 395                 400
Ile Asp Lys Met Asn Thr Gln Phe Glu Ala Val Glu His Glu Phe Ser
                     405                 410                 415
Asn Leu Glu Arg Arg Ile Asp Asn Leu Asn Lys Arg Met Glu Asp Gly
             420                 425                 430
Phe Leu Asp Val Trp Thr Tyr Asn Ala Glu Leu Leu Val Leu Leu Glu
```

```
                  435              440              445
Asn Glu Arg Thr Leu Asp Leu His Asp Ala Asn Val Lys Asn Leu Tyr
450                 455                 460

Glu Lys Val Lys Ser Gln Leu Arg Asp Asn Ala Lys Asp Leu Gly Asn
465                 470                 475                 480

Gly Cys Phe Glu Phe Trp His Lys Cys Asp Asp Glu Cys Ile Asn Ser
                    485                 490                 495

Val Lys Asn Gly Thr Tyr Asp Tyr Pro Lys Tyr Gln Asp Glu Ser Lys
                500                 505                 510

Leu Asn Arg Gln Glu Ile Asp Ser Val Lys Leu Glu Asn Leu Gly Val
            515                 520                 525

Tyr Gln Ile Leu Ala Ile Tyr Ser Thr Val Ser Ser Ser Leu Val Leu
        530                 535                 540

Val Gly Leu Ile Ile Ala Met Gly Leu Trp Met Cys Ser Asn Gly Ser
545                 550                 555                 560

Met Gln Cys Arg Ile Cys Ile
                565

<210> SEQ ID NO 17
<211> LENGTH: 1697
<212> TYPE: DNA
<213> ORGANISM: Influenza A virus
<220> FEATURE:
<221> NAME/KEY: CDS
<222> LOCATION: (8)..(1690)
<223> OTHER INFORMATION:

<400> SEQUENCE: 17 atacaaa atg aac act caa att ctg gta ttc att gcc tgt gtg ctg att      49
        Met Asn Thr Gln Ile Leu Val Phe Ile Ala Cys Val Leu Ile
        1               5                   10 gaa gct aaa gga gac aaa ata tgt ctt gga cac cat gct gtg gca aat      97
Glu Ala Lys Gly Asp Lys Ile Cys Leu Gly His His Ala Val Ala Asn
15                  20                  25                  30 gga aca aag gtg aac acg cta aca gag agg ggg att gaa gta gtg aat     145
Gly Thr Lys Val Asn Thr Leu Thr Glu Arg Gly Ile Glu Val Val Asn
                35                  40                  45 gcc acg gaa aca gtg gaa acc gcg aat atc ggg aaa atc tgc acc caa     193
Ala Thr Glu Thr Val Glu Thr Ala Asn Ile Gly Lys Ile Cys Thr Gln
            50                  55                  60 ggg aaa agg cca aca gac ctg gga caa tgt ggg ctc cta gga acc cta     241
Gly Lys Arg Pro Thr Asp Leu Gly Gln Cys Gly Leu Leu Gly Thr Leu
        65                  70                  75 ata gga cct ccc caa tgt gat caa ttc ctg gag ttt gaa tca aat ttg     289
Ile Gly Pro Pro Gln Cys Asp Gln Phe Leu Glu Phe Glu Ser Asn Leu
    80                  85                  90 ata atc gaa cga agg gaa ggg aac gat gtg tgc tat cct ggg aag ttc     337
Ile Ile Glu Arg Arg Glu Gly Asn Asp Val Cys Tyr Pro Gly Lys Phe
95                  100                 105                 110 aca aat gaa gaa tca ctg agg cag atc ctt cgg ggg tca gga gga gtc     385
Thr Asn Glu Glu Ser Leu Arg Gln Ile Leu Arg Gly Ser Gly Gly Val
                115                 120                 125 gat aaa gag tca atg ggt ttc acc tat agt gga ata aga acc aat gga     433
Asp Lys Glu Ser Met Gly Phe Thr Tyr Ser Gly Ile Arg Thr Asn Gly
            130                 135                 140 gca aca agt gcc tgc aga aga tca ggt tct tcc ttc tat gcg gaa atg     481
Ala Thr Ser Ala Cys Arg Arg Ser Gly Ser Ser Phe Tyr Ala Glu Met
        145                 150                 155 aag tgg ttg ctg tcg aat tca gac aat gcg gca ttc cct caa atg acc     529
Lys Trp Leu Leu Ser Asn Ser Asp Asn Ala Ala Phe Pro Gln Met Thr
```

-continued

```
                160                 165                 170
aaa tca tat aga aat ccc aga aac aaa cca gct ctg ata gtt tgg gga       577
Lys Ser Tyr Arg Asn Pro Arg Asn Lys Pro Ala Leu Ile Val Trp Gly
175                 180                 185                 190 att cac cat tct gga tcg act acc gaa cag acc aga ctc tat gga agt       625
Ile His His Ser Gly Ser Thr Thr Glu Gln Thr Arg Leu Tyr Gly Ser
                195                 200                 205 gga aac aag ttg ata aca gta gga agc tcg aaa tat caa caa tcg ttc       673
Gly Asn Lys Leu Ile Thr Val Gly Ser Ser Lys Tyr Gln Gln Ser Phe
            210                 215                 220 acc cca agt ccg gaa gca cgg cca caa gtg aat gga caa tca ggg aga       721
Thr Pro Ser Pro Glu Ala Arg Pro Gln Val Asn Gly Gln Ser Gly Arg
        225                 230                 235 atc gat ttc cat tgg cta ctc ctt gat ccc aat gac aca gtg act ttc       769
Ile Asp Phe His Trp Leu Leu Leu Asp Pro Asn Asp Thr Val Thr Phe
    240                 245                 250 acc ttc aat gga gca ttc ata gcc cct aat agg gca agt ttc ttt aga       817
Thr Phe Asn Gly Ala Phe Ile Ala Pro Asn Arg Ala Ser Phe Phe Arg
255                 260                 265                 270 gga gaa tca cta gga gtc cag agt gat gtg cct tta gac tct aat tgt       865
Gly Glu Ser Leu Gly Val Gln Ser Asp Val Pro Leu Asp Ser Asn Cys
                275                 280                 285 gga ggg gat tgc ttt cat agt ggg ggc acg ata gtc agt tct ctg cca       913
Gly Gly Asp Cys Phe His Ser Gly Gly Thr Ile Val Ser Ser Leu Pro
            290                 295                 300 ttc caa aac atc aat tct aga acg gtg ggg aaa tgc ccc cga tat gtc       961
Phe Gln Asn Ile Asn Ser Arg Thr Val Gly Lys Cys Pro Arg Tyr Val
        305                 310                 315 aaa cag cca agc ctc ctt tcg gct aca gga atg aga aat gtc cca gag      1009
Lys Gln Pro Ser Leu Leu Ser Ala Thr Gly Met Arg Asn Val Pro Glu
    320                 325                 330 aat cca aag acc aga gga ctt ttt gga gca att gct gga ttc ata gag      1057
Asn Pro Lys Thr Arg Gly Leu Phe Gly Ala Ile Ala Gly Phe Ile Glu
335                 340                 345                 350 aat gga tgg gag ggt ctc atc gat ggg tgg tat ggt ttc agg cat caa      1105
Asn Gly Trp Glu Gly Leu Ile Asp Gly Trp Tyr Gly Phe Arg His Gln
                355                 360                 365 aat gca caa gga gaa gga act gca gct gac tac aaa agc acc caa tct      1153
Asn Ala Gln Gly Glu Gly Thr Ala Ala Asp Tyr Lys Ser Thr Gln Ser
            370                 375                 380 gca ata gat cag atc act ggc aca ttg aat cgt ctg att gac aaa aca      1201
Ala Ile Asp Gln Ile Thr Gly Thr Leu Asn Arg Leu Ile Asp Lys Thr
        385                 390                 395 aat cag cag ttt gag ctg ata gac aat gaa ttc aat gag ata gaa caa      1249
Asn Gln Gln Phe Glu Leu Ile Asp Asn Glu Phe Asn Glu Ile Glu Gln
    400                 405                 410 cag att gga aat gtc att aat tgg aca cga gac tca atg act gaa gta      1297
Gln Ile Gly Asn Val Ile Asn Trp Thr Arg Asp Ser Met Thr Glu Val
415                 420                 425                 430 tgg tcg tat aat gct gag ctg ttg gtg gcc atg gaa aat cag cac aca      1345
Trp Ser Tyr Asn Ala Glu Leu Leu Val Ala Met Glu Asn Gln His Thr
                435                 440                 445 ata gat ctt gcg gat tca gaa atg aac aaa ctt tat gag cgt gtc aga      1393
Ile Asp Leu Ala Asp Ser Glu Met Asn Lys Leu Tyr Glu Arg Val Arg
            450                 455                 460 aaa caa cta agg gag aat gct gaa gaa gat ggg act gga tgt ttt gaa      1441
Lys Gln Leu Arg Glu Asn Ala Glu Glu Asp Gly Thr Gly Cys Phe Glu
        465                 470                 475 ata ttc cat aag tgt gac gac caa tgt atg gag agc ata agg aac aac      1489
Ile Phe His Lys Cys Asp Asp Gln Cys Met Glu Ser Ile Arg Asn Asn
```

```
    480                 485                 490 act tat gac cat acc caa tac aga gca gag tca tta cag aat aga ata      1537
Thr Tyr Asp His Thr Gln Tyr Arg Ala Glu Ser Leu Gln Asn Arg Ile
495                 500                 505                 510 cag ata gac cca gtg aaa ttg agt agt gga tac aaa gac ata atc tta      1585
Gln Ile Asp Pro Val Lys Leu Ser Ser Gly Tyr Lys Asp Ile Ile Leu
                515                 520                 525 tgg ttt agc ttc ggg gca tca tgt ttc ctc ctt cta gcc att gca atg      1633
Trp Phe Ser Phe Gly Ala Ser Cys Phe Leu Leu Leu Ala Ile Ala Met
            530                 535                 540 gga ttg gtc ttc att tgc ata aag aat gga aac atg cgg tgc act att      1681
Gly Leu Val Phe Ile Cys Ile Lys Asn Gly Asn Met Arg Cys Thr Ile
        545                 550                 555 tgt ata tag tttgaga                                                  1697
Cys Ile
    560

<210> SEQ ID NO 18
<211> LENGTH: 560
<212> TYPE: PRT
<213> ORGANISM: Influenza A virus

<400> SEQUENCE: 18

Met Asn Thr Gln Ile Leu Val Phe Ile Ala Cys Val Leu Ile Glu Ala
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Ala Asn Ile Gly Lys Ile Cys Thr Gln Gly Lys
    50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Glu Ser Asn Leu Ile Ile
                85                  90                  95

Glu Arg Arg Glu Gly Asn Asp Val Cys Tyr Pro Gly Lys Phe Thr Asn
            100                 105                 110

Glu Glu Ser Leu Arg Gln Ile Leu Arg Gly Ser Gly Gly Val Asp Lys
        115                 120                 125

Glu Ser Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Val Trp Gly Ile His
            180                 185                 190

His Ser Gly Ser Thr Thr Glu Gln Thr Arg Leu Tyr Gly Ser Gly Asn
        195                 200                 205

Lys Leu Ile Thr Val Gly Ser Ser Lys Tyr Gln Gln Ser Phe Thr Pro
    210                 215                 220

Ser Pro Glu Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asn Arg Ala Ser Phe Phe Arg Gly Glu
            260                 265                 270
```

```
Ser Leu Gly Val Gln Ser Asp Val Pro Leu Asp Ser Asn Cys Gly Gly
            275                 280                 285

Asp Cys Phe His Ser Gly Gly Thr Ile Val Ser Ser Leu Pro Phe Gln
        290                 295                 300

Asn Ile Asn Ser Arg Thr Val Gly Lys Cys Pro Arg Tyr Val Lys Gln
305                 310                 315                 320

Pro Ser Leu Leu Ser Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Thr Leu Asn Arg Leu Ile Asp Lys Thr Asn Gln
385                 390                 395                 400

Gln Phe Glu Leu Ile Asp Asn Glu Phe Asn Glu Ile Glu Gln Gln Ile
                405                 410                 415

Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Arg Lys Gln
    450                 455                 460

Leu Arg Glu Asn Ala Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asp His Thr Gln Tyr Arg Ala Glu Ser Leu Gln Asn Arg Ile Gln Ile
            500                 505                 510

Asp Pro Val Lys Leu Ser Ser Gly Tyr Lys Asp Ile Ile Leu Trp Phe
        515                 520                 525

Ser Phe Gly Ala Ser Cys Phe Leu Leu Ala Ile Ala Met Gly Leu
    530                 535                 540

Val Phe Ile Cys Ile Lys Asn Gly Asn Met Arg Cys Thr Ile Cys Ile
545                 550                 555                 560

<210> SEQ ID NO 19
<211> LENGTH: 1710
<212> TYPE: DNA
<213> ORGANISM: Influenza A virus
<220> FEATURE:
<221> NAME/KEY: CDS
<222> LOCATION: (6)..(1706)
<223> OTHER INFORMATION:

<400> SEQUENCE: 19 tcaca atg gag aaa ttc atc gcc ata gca atg ctc ttg gcg agc aca aat      50
      Met Glu Lys Phe Ile Ala Ile Ala Met Leu Leu Ala Ser Thr Asn
      1               5                   10                  15 gca tac gat agg ata tgc att ggg tac caa tca aac aac tcc aca gac      98
Ala Tyr Asp Arg Ile Cys Ile Gly Tyr Gln Ser Asn Asn Ser Thr Asp
                20                  25                  30 aca gtg aac act ctc ata gaa cag aat gtg cca gtc acc caa aca atg     146
Thr Val Asn Thr Leu Ile Glu Gln Asn Val Pro Val Thr Gln Thr Met
            35                  40                  45 gag ctc gtg gaa aca gag aaa cat ccc gct tat tgt aac act gat tta     194
```

|   |   |   |   |   |   |   |   |   |   |   |   |   |   |
|---|---|---|---|---|---|---|---|---|---|---|---|---|---|
| Glu | Leu | Val<br>50 | Glu | Thr | Glu | Lys | His<br>55 | Pro | Ala | Tyr | Cys | Asn<br>60 | Thr | Asp | Leu |

```
ggt gcc cca ttg gaa ctg cga gac tgc aag gtt gag gca gta atc tat       242
Gly Ala Pro Leu Glu Leu Arg Asp Cys Lys Val Glu Ala Val Ile Tyr
 65              70                  75 ggg aac ccc aag tgt gac atc cat ctg aag gat caa ggt tgg tca tac       290
Gly Asn Pro Lys Cys Asp Ile His Leu Lys Asp Gln Gly Trp Ser Tyr
 80              85                  90                  95 ata gtg gag agg ccc agc gca cca gaa ggg atg tgt tac cct gga tct       338
Ile Val Glu Arg Pro Ser Ala Pro Glu Gly Met Cys Tyr Pro Gly Ser
                100                 105                 110 gtg gaa aat cta gaa gaa ctg agg ttt gtc ttc tcc agt gct gca tct       386
Val Glu Asn Leu Glu Glu Leu Arg Phe Val Phe Ser Ser Ala Ala Ser
            115                 120                 125 tac aag aga ata aga cta ttt gac tat tcc agg tgg aat gtg act aga       434
Tyr Lys Arg Ile Arg Leu Phe Asp Tyr Ser Arg Trp Asn Val Thr Arg
        130                 135                 140 tct gga acg agt aaa gca tgc aat gca tca aca ggt ggc caa tcc ttc       482
Ser Gly Thr Ser Lys Ala Cys Asn Ala Ser Thr Gly Gly Gln Ser Phe
145                 150                 155 tat agg agc atc aat tgg ttg acc aaa aag aaa cca gac act tat gac       530
Tyr Arg Ser Ile Asn Trp Leu Thr Lys Lys Lys Pro Asp Thr Tyr Asp
160                 165                 170                 175 ttc aat gaa gga gct tat gtt aat aat gaa gat gga gac atc att ttc       578
Phe Asn Glu Gly Ala Tyr Val Asn Asn Glu Asp Gly Asp Ile Ile Phe
                180                 185                 190 tta tgg ggg atc cat cat ccg ccg gac aca aaa gag cag aca aca cta       626
Leu Trp Gly Ile His His Pro Pro Asp Thr Lys Glu Gln Thr Thr Leu
            195                 200                 205 tat aaa aat gca aac act ttg agt agt gtt act act aac act ata aac       674
Tyr Lys Asn Ala Asn Thr Leu Ser Ser Val Thr Thr Asn Thr Ile Asn
        210                 215                 220 aga agc ttt caa cca aat att ggt ccc aga cca tta gta aga gga cag       722
Arg Ser Phe Gln Pro Asn Ile Gly Pro Arg Pro Leu Val Arg Gly Gln
225                 230                 235 caa ggg agg atg gat tac tat tgg ggc att ctg aaa aga ggg gag act       770
Gln Gly Arg Met Asp Tyr Tyr Trp Gly Ile Leu Lys Arg Gly Glu Thr
240                 245                 250                 255 ctg aag atc agg acc aac gga aat tta atc gca cct gaa ttt ggc tat       818
Leu Lys Ile Arg Thr Asn Gly Asn Leu Ile Ala Pro Glu Phe Gly Tyr
                260                 265                 270 ctg ctc aaa ggt gaa agc tac ggc aga ata att caa aat gag gat ata       866
Leu Leu Lys Gly Glu Ser Tyr Gly Arg Ile Ile Gln Asn Glu Asp Ile
            275                 280                 285 ccc atc ggg aac tgt aac aca aaa tgt caa aca tat gcg gga gca atc       914
Pro Ile Gly Asn Cys Asn Thr Lys Cys Gln Thr Tyr Ala Gly Ala Ile
        290                 295                 300 aat agc agc aaa ccc ttt cag aat gca agt agg cat tac atg gga gaa       962
Asn Ser Ser Lys Pro Phe Gln Asn Ala Ser Arg His Tyr Met Gly Glu
305                 310                 315 tgt ccc aaa tat gtg aag aag gca agc ttg cga ctt gca gtt ggg ctt      1010
Cys Pro Lys Tyr Val Lys Lys Ala Ser Leu Arg Leu Ala Val Gly Leu
320                 325                 330                 335 agg aat acg cct tct gtt gaa ccc aga gga ctg ttt gga gcc att gct      1058
Arg Asn Thr Pro Ser Val Glu Pro Arg Gly Leu Phe Gly Ala Ile Ala
                340                 345                 350 ggt ttc att gaa gga gga tgg tct gga atg att gat ggg tgg tat gga      1106
Gly Phe Ile Glu Gly Gly Trp Ser Gly Met Ile Asp Gly Trp Tyr Gly
            355                 360                 365 ttt cat cac agc aat tca gag gga aca gga atg gca gct gac cag aaa      1154
```

```
Phe His His Ser Asn Ser Glu Gly Thr Gly Met Ala Ala Asp Gln Lys
        370                 375                 380 tca aca caa gaa gcc atc gat aag atc acc aat aaa gtc aac aat ata      1202
Ser Thr Gln Glu Ala Ile Asp Lys Ile Thr Asn Lys Val Asn Asn Ile
385                 390                 395 gtt gac aag atg aac agg gag ttt gaa gtt gtg aat cat gag ttc tct      1250
Val Asp Lys Met Asn Arg Glu Phe Glu Val Val Asn His Glu Phe Ser
400                 405                 410                 415 gaa gtt gaa aaa aga ata aac atg ata aac gat aaa ata gat gac caa      1298
Glu Val Glu Lys Arg Ile Asn Met Ile Asn Asp Lys Ile Asp Asp Gln
                420                 425                 430 att gaa gat ctt tgg gct tac aat gca gag ctc ctt gtg ctc tta gag      1346
Ile Glu Asp Leu Trp Ala Tyr Asn Ala Glu Leu Leu Val Leu Leu Glu
            435                 440                 445 aac cag aaa acg cta gac gaa cat gat tcc aat gtc aaa aac ctt ttt      1394
Asn Gln Lys Thr Leu Asp Glu His Asp Ser Asn Val Lys Asn Leu Phe
        450                 455                 460 gat gaa gtg aaa agg aga ctg tca gcc aat gca ata gat gct ggg aac      1442
Asp Glu Val Lys Arg Arg Leu Ser Ala Asn Ala Ile Asp Ala Gly Asn
465                 470                 475 ggt tgc ttt gac ata ctt cac aaa tgc gac aat gag tgt atg gaa act      1490
Gly Cys Phe Asp Ile Leu His Lys Cys Asp Asn Glu Cys Met Glu Thr
480                 485                 490                 495 ata aag aac gga act tac gat cat aag gaa tat gaa gag gag gct aaa      1538
Ile Lys Asn Gly Thr Tyr Asp His Lys Glu Tyr Glu Glu Glu Ala Lys
                500                 505                 510 cta gaa agg agc aag ata aat gga gta aaa cta gaa gag aac acc act      1586
Leu Glu Arg Ser Lys Ile Asn Gly Val Lys Leu Glu Glu Asn Thr Thr
            515                 520                 525 tac aaa att ctt agc att tac agt aca gtg gcg gcc agt ctt tgc ttg      1634
Tyr Lys Ile Leu Ser Ile Tyr Ser Thr Val Ala Ala Ser Leu Cys Leu
        530                 535                 540 gca atc ctg att gct gga ggt tta atc ctg ggc atg caa aat gga tct      1682
Ala Ile Leu Ile Ala Gly Gly Leu Ile Leu Gly Met Gln Asn Gly Ser
545                 550                 555 tgt aga tgc atg ttc tgt att tga agaa                                 1710
Cys Arg Cys Met Phe Cys Ile
560                 565

<210> SEQ ID NO 20
<211> LENGTH: 566
<212> TYPE: PRT
<213> ORGANISM: Influenza A virus

<400> SEQUENCE: 20

Met Glu Lys Phe Ile Ala Ile Ala Met Leu Leu Ala Ser Thr Asn Ala
1               5                   10                  15

Tyr Asp Arg Ile Cys Ile Gly Tyr Gln Ser Asn Asn Ser Thr Asp Thr
            20                  25                  30

Val Asn Thr Leu Ile Glu Gln Asn Val Pro Val Thr Gln Thr Met Glu
        35                  40                  45

Leu Val Glu Thr Glu Lys His Pro Ala Tyr Cys Asn Thr Asp Leu Gly
    50                  55                  60

Ala Pro Leu Glu Leu Arg Asp Cys Lys Val Glu Ala Val Ile Tyr Gly
65                  70                  75                  80

Asn Pro Lys Cys Asp Ile His Leu Lys Asp Gln Gly Trp Ser Tyr Ile
                85                  90                  95

Val Glu Arg Pro Ser Ala Pro Glu Gly Met Cys Tyr Pro Gly Ser Val
            100                 105                 110
```

```
Glu Asn Leu Glu Glu Leu Arg Phe Val Phe Ser Ser Ala Ala Ser Tyr
            115                 120                 125

Lys Arg Ile Arg Leu Phe Asp Tyr Ser Arg Trp Asn Val Thr Arg Ser
        130                 135                 140

Gly Thr Ser Lys Ala Cys Asn Ala Ser Thr Gly Gly Gln Ser Phe Tyr
145                 150                 155                 160

Arg Ser Ile Asn Trp Leu Thr Lys Lys Pro Asp Thr Tyr Asp Phe
                165                 170                 175

Asn Glu Gly Ala Tyr Val Asn Asn Glu Asp Gly Asp Ile Ile Phe Leu
                180                 185                 190

Trp Gly Ile His His Pro Pro Asp Thr Lys Glu Gln Thr Thr Leu Tyr
            195                 200                 205

Lys Asn Ala Asn Thr Leu Ser Ser Val Thr Thr Asn Thr Ile Asn Arg
210                 215                 220

Ser Phe Gln Pro Asn Ile Gly Pro Arg Pro Leu Val Arg Gly Gln Gln
225                 230                 235                 240

Gly Arg Met Asp Tyr Tyr Trp Gly Ile Leu Lys Arg Gly Glu Thr Leu
                245                 250                 255

Lys Ile Arg Thr Asn Gly Asn Leu Ile Ala Pro Glu Phe Gly Tyr Leu
                260                 265                 270

Leu Lys Gly Glu Ser Tyr Gly Arg Ile Ile Gln Asn Glu Asp Ile Pro
            275                 280                 285

Ile Gly Asn Cys Asn Thr Lys Cys Gln Thr Tyr Ala Gly Ala Ile Asn
290                 295                 300

Ser Ser Lys Pro Phe Gln Asn Ala Ser Arg His Tyr Met Gly Glu Cys
305                 310                 315                 320

Pro Lys Tyr Val Lys Lys Ala Ser Leu Arg Leu Ala Val Gly Leu Arg
                325                 330                 335

Asn Thr Pro Ser Val Glu Pro Arg Gly Leu Phe Gly Ala Ile Ala Gly
                340                 345                 350

Phe Ile Glu Gly Gly Trp Ser Gly Met Ile Asp Gly Trp Tyr Gly Phe
            355                 360                 365

His His Ser Asn Ser Glu Gly Thr Gly Met Ala Ala Asp Gln Lys Ser
370                 375                 380

Thr Gln Glu Ala Ile Asp Lys Ile Thr Asn Lys Val Asn Asn Ile Val
385                 390                 395                 400

Asp Lys Met Asn Arg Glu Phe Glu Val Val Asn His Glu Phe Ser Glu
                405                 410                 415

Val Glu Lys Arg Ile Asn Met Ile Asn Asp Lys Ile Asp Gln Ile
                420                 425                 430

Glu Asp Leu Trp Ala Tyr Asn Ala Glu Leu Leu Val Leu Leu Glu Asn
            435                 440                 445

Gln Lys Thr Leu Asp Glu His Asp Ser Asn Val Lys Asn Leu Phe Asp
450                 455                 460

Glu Val Lys Arg Arg Leu Ser Ala Asn Ala Ile Asp Ala Gly Asn Gly
465                 470                 475                 480

Cys Phe Asp Ile Leu His Lys Cys Asp Asn Glu Cys Met Glu Thr Ile
                485                 490                 495

Lys Asn Gly Thr Tyr Asp His Lys Glu Tyr Glu Glu Ala Lys Leu
                500                 505                 510

Glu Arg Ser Lys Ile Asn Gly Val Lys Leu Glu Glu Asn Thr Thr Tyr
            515                 520                 525

Lys Ile Leu Ser Ile Tyr Ser Thr Val Ala Ala Ser Leu Cys Leu Ala
530                 535                 540
```

```
Ile Leu Ile Ala Gly Gly Leu Ile Leu Gly Met Gln Asn Gly Ser Cys
545                 550                 555                 560

Arg Cys Met Phe Cys Ile
            565
```

<210> SEQ ID NO 21
<211> LENGTH: 1708
<212> TYPE: DNA
<213> ORGANISM: Influenza A virus
<220> FEATURE:
<221> NAME/KEY: CDS
<222> LOCATION: (20)..(1702)
<223> OTHER INFORMATION:

<400> SEQUENCE: 21

```
aacaacatag ccaatcaag atg gaa aca aaa gca ata att gct gca ctg cta        52
                    Met Glu Thr Lys Ala Ile Ile Ala Ala Leu Leu
                     1               5                   10 atg gta aca gca gcc aat gct gat aaa atc tgc att ggc tat caa tca       100
Met Val Thr Ala Ala Asn Ala Asp Lys Ile Cys Ile Gly Tyr Gln Ser
                 15                  20                  25 aca aac tcc acc gaa act gtc gac aca cta aca gag agc aat gtt cct       148
Thr Asn Ser Thr Glu Thr Val Asp Thr Leu Thr Glu Ser Asn Val Pro
         30                  35                  40 gta aca cac act aaa gaa ttg ctc cac aca gaa cac aat ggg atg ttg       196
Val Thr His Thr Lys Glu Leu Leu His Thr Glu His Asn Gly Met Leu
     45                  50                  55 tgt gca act gat cta gga cat ccc ctc att cta gac acc tgc act att       244
Cys Ala Thr Asp Leu Gly His Pro Leu Ile Leu Asp Thr Cys Thr Ile
 60                  65                  70                  75 gaa gga cta atc tat gga aat cct tcc tgt gac ata cta cta gga gga       292
Glu Gly Leu Ile Tyr Gly Asn Pro Ser Cys Asp Ile Leu Leu Gly Gly
                 80                  85                  90 aaa gaa tgg tcc tac atc gtt gaa agg tcg tca gcc gtc aat gga atg       340
Lys Glu Trp Ser Tyr Ile Val Glu Arg Ser Ser Ala Val Asn Gly Met
             95                 100                 105 tgt tac cca ggg aat gta gag aac cta gaa gag ctt agg tca ctt ttc       388
Cys Tyr Pro Gly Asn Val Glu Asn Leu Glu Glu Leu Arg Ser Leu Phe
        110                 115                 120 agt tct gca aaa tct tac aaa aga atc caa atc ttt cca gat aaa act       436
Ser Ser Ala Lys Ser Tyr Lys Arg Ile Gln Ile Phe Pro Asp Lys Thr
    125                 130                 135 tgg aat gta aca tac agc gga aca agc aga gca tgc tca aat tca ttc       484
Trp Asn Val Thr Tyr Ser Gly Thr Ser Arg Ala Cys Ser Asn Ser Phe
140                 145                 150                 155 tat agg agc atg aga tgg ctg acc cac aag agt aat tcc tac cct ttt       532
Tyr Arg Ser Met Arg Trp Leu Thr His Lys Ser Asn Ser Tyr Pro Phe
                160                 165                 170 cag aac gct cat tac acc aac aat gag agg gag aac att ctt ttc atg       580
Gln Asn Ala His Tyr Thr Asn Asn Glu Arg Glu Asn Ile Leu Phe Met
            175                 180                 185 tgg ggc ata cac cat cca cct acc gac aca gaa cag aca gac tta tac       628
Trp Gly Ile His His Pro Pro Thr Asp Thr Glu Gln Thr Asp Leu Tyr
        190                 195                 200 aag aat gcc gat aca aca aca agt gtg aca aca gaa gat ata aat cgc       676
Lys Asn Ala Asp Thr Thr Thr Ser Val Thr Thr Glu Asp Ile Asn Arg
    205                 210                 215 act ttc aaa cca gta ata ggg cca agg ccc ctt gtc aac ggc cag cag       724
Thr Phe Lys Pro Val Ile Gly Pro Arg Pro Leu Val Asn Gly Gln Gln
220                 225                 230                 235 gga aga atc gat tac tat tgg tct gta cta aaa cct ggg cag act ttg       772
```

```
                   Gly Arg Ile Asp Tyr Tyr Trp Ser Val Leu Lys Pro Gly Gln Thr Leu
                                   240                 245                 250 aga ata agg tcc aat gga aat cta att gcc cct tgg tat gga cat gtt        820
Arg Ile Arg Ser Asn Gly Asn Leu Ile Ala Pro Trp Tyr Gly His Val
                    255                 260                 265 ctt acg gga gag agc cat gga aga atc cta aag act gat ttg aac aat        868
Leu Thr Gly Glu Ser His Gly Arg Ile Leu Lys Thr Asp Leu Asn Asn
                270                 275                 280 ggt aat tgt gtg gta caa tgt cag act gaa aaa gga ctc aat aca            916
Gly Asn Cys Val Val Gln Cys Gln Thr Glu Lys Gly Leu Asn Thr
            285                 290                 295 acc ttg cca ttt cac aat att agc aaa tat gca ttt ggg aat tgt cct        964
Thr Leu Pro Phe His Asn Ile Ser Lys Tyr Ala Phe Gly Asn Cys Pro
300                 305                 310                 315 aag tat gtt gga gtg aaa agt ctc aaa ttg gca gtt ggt tta agg aat       1012
Lys Tyr Val Gly Val Lys Ser Leu Lys Leu Ala Val Gly Leu Arg Asn
                320                 325                 330 gtg cct gct gta tct agt aga gga ctg ttc gga gca ata gct ggg ttc       1060
Val Pro Ala Val Ser Ser Arg Gly Leu Phe Gly Ala Ile Ala Gly Phe
                335                 340                 345 ata gag gga ggt tgg cca ggg cta gtg gcc gga tgg tat ggt ttt caa       1108
Ile Glu Gly Gly Trp Pro Gly Leu Val Ala Gly Trp Tyr Gly Phe Gln
            350                 355                 360 cat tca aac gat cag gga gtt ggg atg gcc gca gac aag gga tct acc       1156
His Ser Asn Asp Gln Gly Val Gly Met Ala Ala Asp Lys Gly Ser Thr
        365                 370                 375 caa aaa gca atc gat aaa ata aca tca aaa gtg aac aac ata atc gat       1204
Gln Lys Ala Ile Asp Lys Ile Thr Ser Lys Val Asn Asn Ile Ile Asp
380                 385                 390                 395 aaa atg aac aag caa tat gag gtc att gat cat gaa ttc aat gag ctt       1252
Lys Met Asn Lys Gln Tyr Glu Val Ile Asp His Glu Phe Asn Glu Leu
                400                 405                 410 gag gcc agg ctg aac atg atc aac aac aaa att gat gat cag att caa       1300
Glu Ala Arg Leu Asn Met Ile Asn Asn Lys Ile Asp Asp Gln Ile Gln
                415                 420                 425 gac att tgg gct tat aat gca gag ttg ctg gtc ttg ctt gaa aac cag       1348
Asp Ile Trp Ala Tyr Asn Ala Glu Leu Leu Val Leu Leu Glu Asn Gln
            430                 435                 440 aaa act cta gat gag cat gat gca aat gtg aac aac cta tac aac aaa       1396
Lys Thr Leu Asp Glu His Asp Ala Asn Val Asn Asn Leu Tyr Asn Lys
        445                 450                 455 gtg aaa aga gcc ttg ggt tcc aat gct gta gag gat gga aac gga tgc       1444
Val Lys Arg Ala Leu Gly Ser Asn Ala Val Glu Asp Gly Asn Gly Cys
460                 465                 470                 475 ttt gaa ctg tac cac aaa tgt gat gat caa tgc atg gaa aca atc aga       1492
Phe Glu Leu Tyr His Lys Cys Asp Asp Gln Cys Met Glu Thr Ile Arg
                480                 485                 490 aat gga acc tac gac agg cag aaa tac caa gaa gaa tca aga tta gaa       1540
Asn Gly Thr Tyr Asp Arg Gln Lys Tyr Gln Glu Glu Ser Arg Leu Glu
                495                 500                 505 agg cag aaa ata gaa ggg gta aag ctg gaa tct gag ggc act tac aag       1588
Arg Gln Lys Ile Glu Gly Val Lys Leu Glu Ser Glu Gly Thr Tyr Lys
            510                 515                 520 atc ctc acc att tat tcg act gtc gcc tca tct ctt gtg ctt gca atg       1636
Ile Leu Thr Ile Tyr Ser Thr Val Ala Ser Ser Leu Val Leu Ala Met
        525                 530                 535 ggg ttt gct gcc ttc cta ttc tgg gcc atg tcc aat ggc tct tgc aga       1684
Gly Phe Ala Ala Phe Leu Phe Trp Ala Met Ser Asn Gly Ser Cys Arg
540                 545                 550                 555 tgc aac att tgt ata taa ttagca                                        1708
```

```
Cys Asn Ile Cys Ile
            560

<210> SEQ ID NO 22
<211> LENGTH: 560
<212> TYPE: PRT
<213> ORGANISM: Influenza A virus

<400> SEQUENCE: 22

Met Glu Thr Lys Ala Ile Ile Ala Ala Leu Leu Met Val Thr Ala Ala
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Ser Asn Val Pro Val Thr His Thr Lys
        35                  40                  45

Glu Leu Leu His Thr Glu His Asn Gly Met Leu Cys Ala Thr Asp Leu
    50                  55                  60

Gly His Pro Leu Ile Leu Asp Thr Cys Thr Ile Glu Gly Leu Ile Tyr
65                  70                  75                  80

Gly Asn Pro Ser Cys Asp Ile Leu Leu Gly Gly Lys Glu Trp Ser Tyr
                85                  90                  95

Ile Val Glu Arg Ser Ser Ala Val Asn Gly Met Cys Tyr Pro Gly Asn
            100                 105                 110

Val Glu Asn Leu Glu Glu Leu Arg Ser Leu Phe Ser Ser Ala Lys Ser
        115                 120                 125

Tyr Lys Arg Ile Gln Ile Phe Pro Asp Lys Thr Trp Asn Val Thr Tyr
    130                 135                 140

Ser Gly Thr Ser Arg Ala Cys Ser Asn Ser Phe Tyr Arg Ser Met Arg
145                 150                 155                 160

Trp Leu Thr His Lys Ser Asn Ser Tyr Pro Phe Gln Asn Ala His Tyr
                165                 170                 175

Thr Asn Asn Glu Arg Glu Asn Ile Leu Phe Met Trp Gly Ile His His
            180                 185                 190

Pro Pro Thr Asp Thr Glu Gln Thr Asp Leu Tyr Lys Asn Ala Asp Thr
        195                 200                 205

Thr Thr Ser Val Thr Thr Glu Asp Ile Asn Arg Thr Phe Lys Pro Val
    210                 215                 220

Ile Gly Pro Arg Pro Leu Val Asn Gly Gln Gln Gly Arg Ile Asp Tyr
225                 230                 235                 240

Tyr Trp Ser Val Leu Lys Pro Gly Gln Thr Leu Arg Ile Arg Ser Asn
                245                 250                 255

Gly Asn Leu Ile Ala Pro Trp Tyr Gly His Val Leu Thr Gly Glu Ser
            260                 265                 270

His Gly Arg Ile Leu Lys Thr Asp Leu Asn Asn Gly Asn Cys Val Val
        275                 280                 285

Gln Cys Gln Thr Glu Lys Gly Gly Leu Asn Thr Thr Leu Pro Phe His
    290                 295                 300

Asn Ile Ser Lys Tyr Ala Phe Gly Asn Cys Pro Lys Tyr Val Gly Val
305                 310                 315                 320

Lys Ser Leu Lys Leu Ala Val Gly Leu Arg Asn Val Pro Ala Val Ser
                325                 330                 335

Ser Arg Gly Leu Phe Gly Ala Ile Ala Gly Phe Ile Glu Gly Gly Trp
            340                 345                 350

Pro Gly Leu Val Ala Gly Trp Tyr Gly Phe Gln His Ser Asn Asp Gln
        355                 360                 365
```

```
Gly Val Gly Met Ala Ala Asp Lys Gly Ser Thr Gln Lys Ala Ile Asp
        370                 375                 380
Lys Ile Thr Ser Lys Val Asn Asn Ile Ile Asp Lys Met Asn Lys Gln
385                 390                 395                 400
Tyr Glu Val Ile Asp His Glu Phe Asn Glu Leu Glu Ala Arg Leu Asn
                405                 410                 415
Met Ile Asn Asn Lys Ile Asp Asp Gln Ile Gln Asp Ile Trp Ala Tyr
            420                 425                 430
Asn Ala Glu Leu Leu Val Leu Leu Glu Asn Gln Lys Thr Leu Asp Glu
        435                 440                 445
His Asp Ala Asn Val Asn Asn Leu Tyr Asn Lys Val Lys Arg Ala Leu
    450                 455                 460
Gly Ser Asn Ala Val Glu Asp Gly Asn Gly Cys Phe Glu Leu Tyr His
465                 470                 475                 480
Lys Cys Asp Asp Gln Cys Met Glu Thr Ile Arg Asn Gly Thr Tyr Asp
                485                 490                 495
Arg Gln Lys Tyr Gln Glu Glu Ser Arg Leu Glu Arg Gln Lys Ile Glu
            500                 505                 510
Gly Val Lys Leu Glu Ser Glu Gly Thr Tyr Lys Ile Leu Thr Ile Tyr
        515                 520                 525
Ser Thr Val Ala Ser Ser Leu Val Leu Ala Met Gly Phe Ala Ala Phe
530                 535                 540
Leu Phe Trp Ala Met Ser Asn Gly Ser Cys Arg Cys Asn Ile Cys Ile
545                 550                 555                 560

<210> SEQ ID NO 23
<211> LENGTH: 1694
<212> TYPE: DNA
<213> ORGANISM: Influenza A virus
<220> FEATURE:
<221> NAME/KEY: CDS
<222> LOCATION: (6)..(1691)
<223> OTHER INFORMATION:

<400> SEQUENCE: 23 tcaca atg tac aaa gta gta gta ata att gcg ctc ctt gga gca gtg aaa        50
      Met Tyr Lys Val Val Val Ile Ile Ala Leu Leu Gly Ala Val Lys
      1               5                   10                  15 ggt ctt gac aga atc tgc cta gga cac cat gcg gtt gcc aat gga acc         98
Gly Leu Asp Arg Ile Cys Leu Gly His His Ala Val Ala Asn Gly Thr
            20                  25                  30 att gtg aag acc ctt aca aat gaa caa gag gaa gtg acc aat gct act        146
Ile Val Lys Thr Leu Thr Asn Glu Gln Glu Glu Val Thr Asn Ala Thr
        35                  40                  45 gag acg gta gag agc aca aat ttg aat aaa ttg tgt atg aaa gga aga        194
Glu Thr Val Glu Ser Thr Asn Leu Asn Lys Leu Cys Met Lys Gly Arg
    50                  55                  60 agc tac aag gac ttg ggc aat tgt cac ccg gta gga atg tta ata gga        242
Ser Tyr Lys Asp Leu Gly Asn Cys His Pro Val Gly Met Leu Ile Gly
65                  70                  75 aca cct gtt tgt gat ccg cac ttg acc ggg acc tgg gac act ctc att        290
Thr Pro Val Cys Asp Pro His Leu Thr Gly Thr Trp Asp Thr Leu Ile
80                  85                  90                  95 gag cga gag aat gcc att gcc cac tgt tat cca ggg gca acc ata aat        338
Glu Arg Glu Asn Ala Ile Ala His Cys Tyr Pro Gly Ala Thr Ile Asn
                100                 105                 110 gaa gaa gca ttg agg cag aaa ata atg gaa agt gga gga atc agc aag        386
Glu Glu Ala Leu Arg Gln Lys Ile Met Glu Ser Gly Gly Ile Ser Lys
            115                 120                 125
```

```
atg agc act ggc ttc act tat ggg tct tcc atc aac tca gct ggg acc       434
Met Ser Thr Gly Phe Thr Tyr Gly Ser Ser Ile Asn Ser Ala Gly Thr
    130                 135                 140 act aag gca tgc atg aga aat gga gga gat agt ttc tat gca gag ctc       482
Thr Lys Ala Cys Met Arg Asn Gly Gly Asp Ser Phe Tyr Ala Glu Leu
145                 150                 155 aaa tgg cta gtg tca aag aca aag gga caa aat ttc cct cag aca aca       530
Lys Trp Leu Val Ser Lys Thr Lys Gly Gln Asn Phe Pro Gln Thr Thr
160                 165                 170                 175 aac acc tat cgg aat acg gac aca gca gaa cat ctc ata ata tgg gga       578
Asn Thr Tyr Arg Asn Thr Asp Thr Ala Glu His Leu Ile Ile Trp Gly
                180                 185                 190 att cat cac cct tcc agc aca cag gaa aag aat gac tta tac gga act       626
Ile His His Pro Ser Ser Thr Gln Glu Lys Asn Asp Leu Tyr Gly Thr
                195                 200                 205 cag tca cta tct ata tca gtt gag agt tct aca tat cag aac aac ttt       674
Gln Ser Leu Ser Ile Ser Val Glu Ser Ser Thr Tyr Gln Asn Asn Phe
        210                 215                 220 gtt cca gtt gtt ggg gca aga cct cag gtc aat gga caa agt ggg cga       722
Val Pro Val Val Gly Ala Arg Pro Gln Val Asn Gly Gln Ser Gly Arg
        225                 230                 235 att gac ttt cac tgg aca cta gta cag ccg ggt gac aac ata acc ttc       770
Ile Asp Phe His Trp Thr Leu Val Gln Pro Gly Asp Asn Ile Thr Phe
240                 245                 250                 255 tca cac aat gga ggt cta ata gca cca agt cga gtt agc aaa tta act       818
Ser His Asn Gly Gly Leu Ile Ala Pro Ser Arg Val Ser Lys Leu Thr
                260                 265                 270 gga agg gga ttg gga atc caa tca gaa gcg ttg ata gac aac agt tgt       866
Gly Arg Gly Leu Gly Ile Gln Ser Glu Ala Leu Ile Asp Asn Ser Cys
                275                 280                 285 gaa tcc aaa tgc ttt tgg aga ggg ggt tct ata aat aca aag ctc cct       914
Glu Ser Lys Cys Phe Trp Arg Gly Gly Ser Ile Asn Thr Lys Leu Pro
        290                 295                 300 ttt caa aat ctg tca ccc aga aca gta ggt caa tgc ccc aaa tac gta       962
Phe Gln Asn Leu Ser Pro Arg Thr Val Gly Gln Cys Pro Lys Tyr Val
305                 310                 315 aat cag agg agt tta ctg ctt gca aca ggg atg agg aat gtg cca gaa      1010
Asn Gln Arg Ser Leu Leu Leu Ala Thr Gly Met Arg Asn Val Pro Glu
320                 325                 330                 335 gtg gtg cag gga agg ggt ctg ttt ggt gca ata gca ggg ttc ata gaa      1058
Val Val Gln Gly Arg Gly Leu Phe Gly Ala Ile Ala Gly Phe Ile Glu
                340                 345                 350 aac gga tgg gaa gga atg gta gac ggc tgg tat ggt ttc aga cac caa      1106
Asn Gly Trp Glu Gly Met Val Asp Gly Trp Tyr Gly Phe Arg His Gln
                355                 360                 365 aat gcc cag ggc aca ggc caa gct gct gat tac aag agt act caa gca      1154
Asn Ala Gln Gly Thr Gly Gln Ala Ala Asp Tyr Lys Ser Thr Gln Ala
        370                 375                 380 gct att gac caa atc aca ggg aaa ctg aac agg ttg att gag aag acc      1202
Ala Ile Asp Gln Ile Thr Gly Lys Leu Asn Arg Leu Ile Glu Lys Thr
385                 390                 395 aac act gag ttt gag tca ata gaa tct gaa ttc agt gag act gag cat      1250
Asn Thr Glu Phe Glu Ser Ile Glu Ser Glu Phe Ser Glu Thr Glu His
400                 405                 410                 415 caa att ggt aac gtc att aat tgg acc aaa gat tca ata acc gac att      1298
Gln Ile Gly Asn Val Ile Asn Trp Thr Lys Asp Ser Ile Thr Asp Ile
                420                 425                 430 tgg act tat caa gca gag cta tta gtg gca atg gag aat cag cac aca      1346
Trp Thr Tyr Gln Ala Glu Leu Leu Val Ala Met Glu Asn Gln His Thr
            435                 440                 445
```

```
att gac atg gct gat tca gag atg cta aat ctg tat gaa agg gta aga      1394
Ile Asp Met Ala Asp Ser Glu Met Leu Asn Leu Tyr Glu Arg Val Arg
        450                 455                 460 aag caa ctc aga cag aat gca gaa gaa gac gga aag gga tgt ttt gag      1442
Lys Gln Leu Arg Gln Asn Ala Glu Glu Asp Gly Lys Gly Cys Phe Glu
465                 470                 475 ata tat cat act tgt gat gat tcg tgc atg gag agt ata agg aac aat      1490
Ile Tyr His Thr Cys Asp Asp Ser Cys Met Glu Ser Ile Arg Asn Asn
480                 485                 490                 495 act tat gac cat tca caa tac aga gag gag gct ctt ctg aat aga ctg      1538
Thr Tyr Asp His Ser Gln Tyr Arg Glu Glu Ala Leu Leu Asn Arg Leu
                500                 505                 510 aac atc aac tca gtg aaa ctt tct tcg ggg tac aaa gac atc ata ctt      1586
Asn Ile Asn Ser Val Lys Leu Ser Ser Gly Tyr Lys Asp Ile Ile Leu
            515                 520                 525 tgg ttt agc ttc ggg gca tca tgc ttt gtt ctt cta gcc gtt gtt atg      1634
Trp Phe Ser Phe Gly Ala Ser Cys Phe Val Leu Leu Ala Val Val Met
        530                 535                 540 ggt ctt gtt ttc ttc tgc ctg aaa aat gga aac atg cga tgc aca atc      1682
Gly Leu Val Phe Phe Cys Leu Lys Asn Gly Asn Met Arg Cys Thr Ile
545                 550                 555 tgt att tag tta                                                       1694
Cys Ile
560

<210> SEQ ID NO 24
<211> LENGTH: 561
<212> TYPE: PRT
<213> ORGANISM: Influenza A virus

<400> SEQUENCE: 24

Met Tyr Lys Val Val Ile Ala Leu Leu Gly Ala Val Lys Gly
1               5                   10                  15

Leu Asp Arg Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
        35                  40                  45

Thr Val Glu Ser Thr Asn Leu Asn Lys Leu Cys Met Lys Gly Arg Ser
    50                  55                  60

Tyr Lys Asp Leu Gly Asn Cys His Pro Val Gly Met Leu Ile Gly Thr
65                  70                  75                  80

Pro Val Cys Asp Pro His Leu Thr Gly Thr Trp Asp Thr Leu Ile Glu
                85                  90                  95

Arg Glu Asn Ala Ile Ala His Cys Tyr Pro Gly Ala Thr Ile Asn Glu
            100                 105                 110

Glu Ala Leu Arg Gln Lys Ile Met Glu Ser Gly Gly Ile Ser Lys Met
        115                 120                 125

Ser Thr Gly Phe Thr Tyr Gly Ser Ser Ile Asn Ser Ala Gly Thr Thr
    130                 135                 140

Lys Ala Cys Met Arg Asn Gly Gly Asp Ser Phe Tyr Ala Glu Leu Lys
145                 150                 155                 160

Trp Leu Val Ser Lys Thr Lys Gly Gln Asn Phe Pro Gln Thr Thr Asn
                165                 170                 175

Thr Tyr Arg Asn Thr Asp Thr Ala Glu His Leu Ile Ile Trp Gly Ile
            180                 185                 190

His His Pro Ser Ser Thr Gln Glu Lys Asn Asp Leu Tyr Gly Thr Gln
        195                 200                 205

Ser Leu Ser Ile Ser Val Glu Ser Ser Thr Tyr Gln Asn Asn Phe Val
```

|  |  |  |  |  | 210 |  |  |  |  | 215 |  |  |  |  | 220 |  |  |
|--|--|--|--|--|--|--|--|--|--|--|--|--|--|--|--|--|--|

Pro Val Val Gly Ala Arg Pro Gln Val Asn Gly Gln Ser Gly Arg Ile
225                 230                 235                 240

Asp Phe His Trp Thr Leu Val Gln Pro Gly Asp Asn Ile Thr Phe Ser
            245                 250                 255

His Asn Gly Gly Leu Ile Ala Pro Ser Arg Val Ser Lys Leu Thr Gly
            260                 265                 270

Arg Gly Leu Gly Ile Gln Ser Glu Ala Leu Ile Asp Asn Ser Cys Glu
            275                 280                 285

Ser Lys Cys Phe Trp Arg Gly Gly Ser Ile Asn Thr Lys Leu Pro Phe
290                 295                 300

Gln Asn Leu Ser Pro Arg Thr Val Gly Gln Cys Pro Lys Tyr Val Asn
305                 310                 315                 320

Gln Arg Ser Leu Leu Leu Ala Thr Gly Met Arg Asn Val Pro Glu Val
            325                 330                 335

Val Gln Gly Arg Gly Leu Phe Gly Ala Ile Ala Gly Phe Ile Glu Asn
            340                 345                 350

Gly Trp Glu Gly Met Val Asp Gly Trp Tyr Gly Phe Arg His Gln Asn
            355                 360                 365

Ala Gln Gly Thr Gly Gln Ala Ala Asp Tyr Lys Ser Thr Gln Ala Ala
370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Thr Glu His Gln
            405                 410                 415

Ile Gly Asn Val Ile Asn Trp Thr Lys Asp Ser Ile Thr Asp Ile Trp
            420                 425                 430

Thr Tyr Gln Ala Glu Leu Leu Val Ala Met Glu Asn Gln His Thr Ile
            435                 440                 445

Asp Met Ala Asp Ser Glu Met Leu Asn Leu Tyr Glu Arg Val Arg Lys
450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
            485                 490                 495

Tyr Asp His Ser Gln Tyr Arg Glu Glu Ala Leu Leu Asn Arg Leu Asn
            500                 505                 510

Ile Asn Ser Val Lys Leu Ser Ser Gly Tyr Lys Asp Ile Ile Leu Trp
            515                 520                 525

Phe Ser Phe Gly Ala Ser Cys Phe Val Leu Leu Ala Val Val Met Gly
530                 535                 540

Leu Val Phe Phe Cys Leu Lys Asn Gly Asn Met Arg Cys Thr Ile Cys
545                 550                 555                 560

Ile

<210> SEQ ID NO 25
<211> LENGTH: 281
<212> TYPE: DNA
<213> ORGANISM: Influenza A virus
<220> FEATURE:
<221> NAME/KEY: CDS
<222> LOCATION: (33)..(281)
<223> OTHER INFORMATION:

<400> SEQUENCE: 25
agcaaaagca ggggatctat caagaagtcg aa atg gag aaa atc ctg cta ttt    53

```
                        Met Glu Lys Ile Leu Leu Phe
                         1               5
gca gct att ttc ctt tgt gtg aaa gca gat gag atc tgt atc ggg tat     101
Ala Ala Ile Phe Leu Cys Val Lys Ala Asp Glu Ile Cys Ile Gly Tyr
         10                  15                  20 tta agc aac aac tcg aca gac aaa gtt gac aca ata att gag aac aat     149
Leu Ser Asn Asn Ser Thr Asp Lys Val Asp Thr Ile Ile Glu Asn Asn
     25                  30                  35 gtc acg gtc act agc tca gtg gaa ctg gtt gag aca gaa cac act gga     197
Val Thr Val Thr Ser Ser Val Glu Leu Val Glu Thr Glu His Thr Gly
 40                  45                  50                  55 tca ttc tgt tca atc aat gga aaa caa cca atc agc ctt gga gat tgt     245
Ser Phe Cys Ser Ile Asn Gly Lys Gln Pro Ile Ser Leu Gly Asp Cys
                 60                  65                  70 tca ttt gct gga tgg ata tta ggc aac cct atg tgt                     281
Ser Phe Ala Gly Trp Ile Leu Gly Asn Pro Met Cys
             75                  80

<210> SEQ ID NO 26
<211> LENGTH: 83
<212> TYPE: PRT
<213> ORGANISM: Influenza A virus

<400> SEQUENCE: 26

Met Glu Lys Ile Leu Leu Phe Ala Ala Ile Phe Leu Cys Val Lys Ala
 1               5                  10                  15

Asp Glu Ile Cys Ile Gly Tyr Leu Ser Asn Asn Ser Thr Asp Lys Val
             20                  25                  30

Asp Thr Ile Ile Glu Asn Asn Val Thr Val Thr Ser Ser Val Glu Leu
         35                  40                  45

Val Glu Thr Glu His Thr Gly Ser Phe Cys Ser Ile Asn Gly Lys Gln
     50                  55                  60

Pro Ile Ser Leu Gly Asp Cys Ser Phe Ala Gly Trp Ile Leu Gly Asn
 65                  70                  75                  80

Pro Met Cys

<210> SEQ ID NO 27
<211> LENGTH: 322
<212> TYPE: DNA
<213> ORGANISM: Influenza A virus
<220> FEATURE:
<221> NAME/KEY: CDS
<222> LOCATION: (20)..(322)
<223> OTHER INFORMATION:

<400> SEQUENCE: 27
agcaaaagca ggggtcaca atg gaa aaa ttc atc att ttg agt act gtc ttg     52
                    Met Glu Lys Phe Ile Ile Leu Ser Thr Val Leu
                     1               5                  10 gca gca agc ttt gca tat gac aaa att tgc att gga tac cag aca aac    100
Ala Ala Ser Phe Ala Tyr Asp Lys Ile Cys Ile Gly Tyr Gln Thr Asn
             15                  20                  25 aac tcg act gaa acg gta aac aca cta agt gaa tta aac gtt ccg gtg    148
Asn Ser Thr Glu Thr Val Asn Thr Leu Ser Glu Leu Asn Val Pro Val
         30                  35                  40 acg cag gtg gaa gaa ctt gta cat ggt ggg att gat ccg atc ctg tgt    196
Thr Gln Val Glu Glu Leu Val His Gly Gly Ile Asp Pro Ile Leu Cys
     45                  50                  55 gga acg gaa cta gga tca cca cta gtg ctt gat gac tgt tca tta gag    244
Gly Thr Glu Leu Gly Ser Pro Leu Val Leu Asp Asp Cys Ser Leu Glu
 60                  65                  70                  75
```

```
ggc cta atc cta ggc aat ccc aaa tgt gat ctt tat ttg aat ggc agg      292
Gly Leu Ile Leu Gly Asn Pro Lys Cys Asp Leu Tyr Leu Asn Gly Arg
                80                  85                  90 gaa tgg tca tac ata gta gag agg ccc aaa                              322
Glu Trp Ser Tyr Ile Val Glu Arg Pro Lys
            95                  100

<210> SEQ ID NO 28
<211> LENGTH: 101
<212> TYPE: PRT
<213> ORGANISM: Influenza A virus

<400> SEQUENCE: 28

Met Glu Lys Phe Ile Ile Leu Ser Thr Val Leu Ala Ala Ser Phe Ala
1               5                   10                  15

Tyr Asp Lys Ile Cys Ile Gly Tyr Gln Thr Asn Asn Ser Thr Glu Thr
            20                  25                  30

Val Asn Thr Leu Ser Glu Leu Asn Val Pro Val Thr Gln Val Glu Glu
        35                  40                  45

Leu Val His Gly Gly Ile Asp Pro Ile Leu Cys Gly Thr Glu Leu Gly
    50                  55                  60

Ser Pro Leu Val Leu Asp Asp Cys Ser Leu Glu Gly Leu Ile Leu Gly
65                  70                  75                  80

Asn Pro Lys Cys Asp Leu Tyr Leu Asn Gly Arg Glu Trp Ser Tyr Ile
                85                  90                  95

Val Glu Arg Pro Lys
            100

<210> SEQ ID NO 29
<211> LENGTH: 1734
<212> TYPE: DNA
<213> ORGANISM: Influenza A virus
<220> FEATURE:
<221> NAME/KEY: CDS
<222> LOCATION: (28)..(1728)
<223> OTHER INFORMATION:

<400> SEQUENCE: 29
aaatcttaac aatcagaaac aaacaag atg gct cta aat gtc att gca act ttg     54
                              Met Ala Leu Asn Val Ile Ala Thr Leu
                              1               5 aca ctt ata agt gta tgt gta cat gca gac aga ata tgc gtg ggg tat      102
Thr Leu Ile Ser Val Cys Val His Ala Asp Arg Ile Cys Val Gly Tyr
10                  15                  20                  25 ctg agc acc aat tca tca gaa agg gtc gac acg ctc ctt gaa aat ggg      150
Leu Ser Thr Asn Ser Ser Glu Arg Val Asp Thr Leu Leu Glu Asn Gly
                30                  35                  40 gtc cca gtc acc agc tcc att gat ctg att gag aca aac cac aca gga      198
Val Pro Val Thr Ser Ser Ile Asp Leu Ile Glu Thr Asn His Thr Gly
            45                  50                  55 aca tac tgt tct cta aat gga gtc agt cca gtg cat ttg gga gat tgc      246
Thr Tyr Cys Ser Leu Asn Gly Val Ser Pro Val His Leu Gly Asp Cys
        60                  65                  70 agc ttt gaa gga tgg att gta gga aac cca gcc tgc acc agc aac ttt      294
Ser Phe Glu Gly Trp Ile Val Gly Asn Pro Ala Cys Thr Ser Asn Phe
    75                  80                  85 ggg acc aga gag tgg tca tac ctg att gag gac ccc gcg gcc cct cat      342
Gly Thr Arg Glu Trp Ser Tyr Leu Ile Glu Asp Pro Ala Ala Pro His
90                  95                  100                 105 ggg ctt tgc tac cct gga gaa tta aac aac aat ggt gaa ctc aga cac      390
Gly Leu Cys Tyr Pro Gly Glu Leu Asn Asn Asn Gly Glu Leu Arg His
                110                 115                 120
```

```
ttg ttc agt gga atc agg tca ttc agt aga acg gaa ttg atc cca cct       438
Leu Phe Ser Gly Ile Arg Ser Phe Ser Arg Thr Glu Leu Ile Pro Pro
        125                 130                 135 acc tcc tgg ggg gaa gta ctt gac ggt aca aca tct gct tgc aga gat       486
Thr Ser Trp Gly Glu Val Leu Asp Gly Thr Thr Ser Ala Cys Arg Asp
        140                 145                 150 aac acg gga acc aac agc ttc tat cga aat tta gtt tgg ttt ata aag       534
Asn Thr Gly Thr Asn Ser Phe Tyr Arg Asn Leu Val Trp Phe Ile Lys
        155                 160                 165 aag aat aat aga tat cca gtt atc agt aag acc tac aac aat aca acg       582
Lys Asn Asn Arg Tyr Pro Val Ile Ser Lys Thr Tyr Asn Asn Thr Thr
170                 175                 180                 185 gga agg gat gtt tta gtt tta tgg gga ata cat cac cca gtg tct gtg       630
Gly Arg Asp Val Leu Val Leu Trp Gly Ile His His Pro Val Ser Val
                190                 195                 200 gat gag aca aag act ctg tat gtc aat agt gat cca tac aca ctg gtt       678
Asp Glu Thr Lys Thr Leu Tyr Val Asn Ser Asp Pro Tyr Thr Leu Val
                205                 210                 215 tcc acc aag tct tgg agc gag aaa tat aaa cta gaa acg gga gtc cga       726
Ser Thr Lys Ser Trp Ser Glu Lys Tyr Lys Leu Glu Thr Gly Val Arg
        220                 225                 230 cct ggc tat aat gga cag agg agc tgg atg aaa att tat tgg tct ttg       774
Pro Gly Tyr Asn Gly Gln Arg Ser Trp Met Lys Ile Tyr Trp Ser Leu
        235                 240                 245 ata cat cca ggg gag atg att act ttc gag agt aat ggt gga ttt tta       822
Ile His Pro Gly Glu Met Ile Thr Phe Glu Ser Asn Gly Gly Phe Leu
250                 255                 260                 265 gcc cca aga tat ggg tac ata att gaa gaa tat gga aaa gga agg att       870
Ala Pro Arg Tyr Gly Tyr Ile Ile Glu Glu Tyr Gly Lys Gly Arg Ile
                270                 275                 280 ttc cag agt cgc atc aga atg tct agg tgc aac acc aag tgc cag act       918
Phe Gln Ser Arg Ile Arg Met Ser Arg Cys Asn Thr Lys Cys Gln Thr
                285                 290                 295 tcg gtt gga ggg ata aac aca aac aga acg ttc caa aac atc gat aag       966
Ser Val Gly Gly Ile Asn Thr Asn Arg Thr Phe Gln Asn Ile Asp Lys
        300                 305                 310 aat gct ctt ggt gac tgt ccc aaa tac ata aag tct ggc caa ctc aag      1014
Asn Ala Leu Gly Asp Cys Pro Lys Tyr Ile Lys Ser Gly Gln Leu Lys
315                 320                 325 cta gcc act gga ctc aga aat gtg cca gct ata tcg aat aga gga ttg      1062
Leu Ala Thr Gly Leu Arg Asn Val Pro Ala Ile Ser Asn Arg Gly Leu
330                 335                 340                 345 ttc gga gca att gca ggg ttc ata gaa gga ggc tgg cca ggt tta atc      1110
Phe Gly Ala Ile Ala Gly Phe Ile Glu Gly Gly Trp Pro Gly Leu Ile
                350                 355                 360 aat ggt tgg tac ggt ttt cag cat caa aat gaa cag gga aca gga ata      1158
Asn Gly Trp Tyr Gly Phe Gln His Gln Asn Glu Gln Gly Thr Gly Ile
        365                 370                 375 gct gca gac aaa gaa tca aca cag aaa gct ata gac cag ata aca acc      1206
Ala Ala Asp Lys Glu Ser Thr Gln Lys Ala Ile Asp Gln Ile Thr Thr
        380                 385                 390 aaa ata aat aac att att gat aaa atg aat ggg aac tat gat tca att      1254
Lys Ile Asn Asn Ile Ile Asp Lys Met Asn Gly Asn Tyr Asp Ser Ile
395                 400                 405 agg ggt gaa ttc aat caa gtt gag aag cgt ata aac atg ctt gca gac      1302
Arg Gly Glu Phe Asn Gln Val Glu Lys Arg Ile Asn Met Leu Ala Asp
410                 415                 420                 425 aga ata gat gat gcc gtg acg gac att tgg tca tac aat gcc aaa ctt      1350
Arg Ile Asp Asp Ala Val Thr Asp Ile Trp Ser Tyr Asn Ala Lys Leu
                430                 435                 440
```

```
ctt gta ttg ctg gaa aat gat aaa act tta gat atg cat gat gct aat      1398
Leu Val Leu Leu Glu Asn Asp Lys Thr Leu Asp Met His Asp Ala Asn
            445                 450                 455 gta aag aat tta cat gag caa gta cga aga gaa ttg aag gac aat gca      1446
Val Lys Asn Leu His Glu Gln Val Arg Arg Glu Leu Lys Asp Asn Ala
        460                 465                 470 att gac gaa gga aat ggc tgt ttt gaa ctc ctt cat aaa tgc aat gac      1494
Ile Asp Glu Gly Asn Gly Cys Phe Glu Leu Leu His Lys Cys Asn Asp
    475                 480                 485 tcc tgc atg gaa act ata aga aat gga acg tat gac cac act gag tat      1542
Ser Cys Met Glu Thr Ile Arg Asn Gly Thr Tyr Asp His Thr Glu Tyr
490                 495                 500                 505 gca gag gag tca aag tta aag agg caa gaa atc gat ggg atc aaa ctc      1590
Ala Glu Glu Ser Lys Leu Lys Arg Gln Glu Ile Asp Gly Ile Lys Leu
                510                 515                 520 aaa tca gaa gac aac gtt tac aaa gca tta tca ata tac agt tgc att      1638
Lys Ser Glu Asp Asn Val Tyr Lys Ala Leu Ser Ile Tyr Ser Cys Ile
            525                 530                 535 gca agt agt gtt gta cta gta gga ctc ata ctc tct ttc atc atg tgg      1686
Ala Ser Ser Val Val Leu Val Gly Leu Ile Leu Ser Phe Ile Met Trp
        540                 545                 550 gcc tgt agt agt ggg aat tgc cga ttc aat gtt tgt ata taa gtagaa       1734
Ala Cys Ser Ser Gly Asn Cys Arg Phe Asn Val Cys Ile
    555                 560                 565

<210> SEQ ID NO 30
<211> LENGTH: 566
<212> TYPE: PRT
<213> ORGANISM: Influenza A virus

<400> SEQUENCE: 30

Met Ala Leu Asn Val Ile Ala Thr Leu Thr Leu Ile Ser Val Cys Val
1               5                   10                  15

His Ala Asp Arg Ile Cys Val Gly Tyr Leu Ser Thr Asn Ser Ser Glu
            20                  25                  30

Arg Val Asp Thr Leu Leu Glu Asn Gly Val Pro Val Thr Ser Ser Ile
        35                  40                  45

Asp Leu Ile Glu Thr Asn His Thr Gly Thr Tyr Cys Ser Leu Asn Gly
    50                  55                  60

Val Ser Pro Val His Leu Gly Asp Cys Ser Phe Glu Gly Trp Ile Val
65                  70                  75                  80

Gly Asn Pro Ala Cys Thr Ser Asn Phe Gly Thr Arg Glu Trp Ser Tyr
                85                  90                  95

Leu Ile Glu Asp Pro Ala Ala Pro His Gly Leu Cys Tyr Pro Gly Glu
            100                 105                 110

Leu Asn Asn Asn Gly Glu Leu Arg His Leu Phe Ser Gly Ile Arg Ser
        115                 120                 125

Phe Ser Arg Thr Glu Leu Ile Pro Pro Thr Ser Trp Gly Glu Val Leu
    130                 135                 140

Asp Gly Thr Thr Ser Ala Cys Arg Asp Asn Thr Gly Thr Asn Ser Phe
145                 150                 155                 160

Tyr Arg Asn Leu Val Trp Phe Ile Lys Lys Asn Asn Arg Tyr Pro Val
                165                 170                 175

Ile Ser Lys Thr Tyr Asn Asn Thr Thr Gly Arg Asp Val Leu Val Leu
            180                 185                 190

Trp Gly Ile His His Pro Val Ser Val Asp Glu Thr Lys Thr Leu Tyr
        195                 200                 205
```

```
Val Asn Ser Asp Pro Tyr Thr Leu Val Ser Thr Lys Ser Trp Ser Glu
            210                 215                 220

Lys Tyr Lys Leu Glu Thr Gly Val Arg Pro Gly Tyr Asn Gly Gln Arg
225                 230                 235                 240

Ser Trp Met Lys Ile Tyr Trp Ser Leu Ile His Pro Gly Glu Met Ile
                245                 250                 255

Thr Phe Glu Ser Asn Gly Gly Phe Leu Ala Pro Arg Tyr Gly Tyr Ile
            260                 265                 270

Ile Glu Glu Tyr Gly Lys Gly Arg Ile Phe Gln Ser Arg Ile Arg Met
        275                 280                 285

Ser Arg Cys Asn Thr Lys Cys Gln Thr Ser Val Gly Gly Ile Asn Thr
290                 295                 300

Asn Arg Thr Phe Gln Asn Ile Asp Lys Asn Ala Leu Gly Asp Cys Pro
305                 310                 315                 320

Lys Tyr Ile Lys Ser Gly Gln Leu Lys Leu Ala Thr Gly Leu Arg Asn
                325                 330                 335

Val Pro Ala Ile Ser Asn Arg Gly Leu Phe Gly Ala Ile Ala Gly Phe
            340                 345                 350

Ile Glu Gly Gly Trp Pro Gly Leu Ile Asn Gly Trp Tyr Gly Phe Gln
        355                 360                 365

His Gln Asn Glu Gln Gly Thr Gly Ile Ala Ala Asp Lys Glu Ser Thr
370                 375                 380

Gln Lys Ala Ile Asp Gln Ile Thr Thr Lys Ile Asn Asn Ile Ile Asp
385                 390                 395                 400

Lys Met Asn Gly Asn Tyr Asp Ser Ile Arg Gly Glu Phe Asn Gln Val
                405                 410                 415

Glu Lys Arg Ile Asn Met Leu Ala Asp Arg Ile Asp Asp Ala Val Thr
            420                 425                 430

Asp Ile Trp Ser Tyr Asn Ala Lys Leu Leu Val Leu Leu Glu Asn Asp
        435                 440                 445

Lys Thr Leu Asp Met His Asp Ala Asn Val Lys Asn Leu His Glu Gln
450                 455                 460

Val Arg Arg Glu Leu Lys Asp Asn Ala Ile Asp Glu Gly Asn Gly Cys
465                 470                 475                 480

Phe Glu Leu Leu His Lys Cys Asn Asp Ser Cys Met Glu Thr Ile Arg
                485                 490                 495

Asn Gly Thr Tyr Asp His Thr Glu Tyr Ala Glu Glu Ser Lys Leu Lys
            500                 505                 510

Arg Gln Glu Ile Asp Gly Ile Lys Leu Lys Ser Glu Asp Asn Val Tyr
        515                 520                 525

Lys Ala Leu Ser Ile Tyr Ser Cys Ile Ala Ser Val Val Leu Val
530                 535                 540

Gly Leu Ile Leu Ser Phe Ile Met Trp Ala Cys Ser Ser Gly Asn Cys
545                 550                 555                 560

Arg Phe Asn Val Cys Ile
                565

<210> SEQ ID NO 31
<211> LENGTH: 1714
<212> TYPE: DNA
<213> ORGANISM: Influenza A virus
<220> FEATURE:
<221> NAME/KEY: CDS
<222> LOCATION: (4)..(1710)
<223> OTHER INFORMATION:

<400> SEQUENCE: 31
```

| | | |
|---|---|---|
| aaa atg att gca ctc ata ttg gtt gca ctg gct ctg agc cac act gct<br>    Met Ile Ala Leu Ile Leu Val Ala Leu Ala Leu Ser His Thr Ala<br>    1                5                    10                  15 | 48 | |
| tat tct cag atc aca aat ggg aca aca gga aac ccc att ata tgc ttg<br>Tyr Ser Gln Ile Thr Asn Gly Thr Thr Gly Asn Pro Ile Ile Cys Leu<br>                20                    25                    30 | 96 | |
| ggg cat cat gca gtg gaa aac ggc aca tct gtt aaa aca cta aca gac<br>Gly His His Ala Val Glu Asn Gly Thr Ser Val Lys Thr Leu Thr Asp<br>          35                    40                    45 | 144 | |
| aat cac gta gaa gtt gtg tca gct aaa gaa tta gtt gag acg aac cac<br>Asn His Val Glu Val Val Ser Ala Lys Glu Leu Val Glu Thr Asn His<br>        50                    55                    60 | 192 | |
| act gat gaa ctg tgc cca agc ccc ttg aag ctt gtc gac ggg caa gac<br>Thr Asp Glu Leu Cys Pro Ser Pro Leu Lys Leu Val Asp Gly Gln Asp<br>    65                    70                    75 | 240 | |
| tgc gac ctc atc aat ggt gca ttg ggg agt cca ggc tgt gac cgt ttg<br>Cys Asp Leu Ile Asn Gly Ala Leu Gly Ser Pro Gly Cys Asp Arg Leu<br>80                    85                    90                    95 | 288 | |
| cag gac acc act tgg gat gtc ttc att gaa agg ccc act gca gta gac<br>Gln Asp Thr Thr Trp Asp Val Phe Ile Glu Arg Pro Thr Ala Val Asp<br>                100                 105              110 | 336 | |
| aca tgt tat cca ttc gac gtc cca gat tac cag agt ctc aga agc atc<br>Thr Cys Tyr Pro Phe Asp Val Pro Asp Tyr Gln Ser Leu Arg Ser Ile<br>            115                 120              125 | 384 | |
| cta gca agc agt ggg agt ttg gag ttc atc gcc gaa caa ttc acc tgg<br>Leu Ala Ser Ser Gly Ser Leu Glu Phe Ile Ala Glu Gln Phe Thr Trp<br>        130                 135              140 | 432 | |
| aat ggt gtc aaa gtt gac gga tca agc agt gct tgt ttg agg ggc ggt<br>Asn Gly Val Lys Val Asp Gly Ser Ser Ser Ala Cys Leu Arg Gly Gly<br>    145                 150              155 | 480 | |
| cgc aac agc ttc ttc tcc cga cta aac tgg cta acc aaa gaa aca aat<br>Arg Asn Ser Phe Phe Ser Arg Leu Asn Trp Leu Thr Lys Glu Thr Asn<br>160                    165                 170              175 | 528 | |
| gga aac tat gga cct att aac gtc act aaa gaa aat acg ggc tct tat<br>Gly Asn Tyr Gly Pro Ile Asn Val Thr Lys Glu Asn Thr Gly Ser Tyr<br>                180                 185              190 | 576 | |
| gtc agg ctc tat ctc tgg gga gtg cat cac cca tca agc gat aat gag<br>Val Arg Leu Tyr Leu Trp Gly Val His His Pro Ser Ser Asp Asn Glu<br>            195                 200              205 | 624 | |
| caa acg gat ctc tac aag gtg gca aca ggg aga gta aca gta tct acc<br>Gln Thr Asp Leu Tyr Lys Val Ala Thr Gly Arg Val Thr Val Ser Thr<br>        210                 215              220 | 672 | |
| cgc tcg gac caa atc agt att gtt ccc aat ata gga agt aga ccg agg<br>Arg Ser Asp Gln Ile Ser Ile Val Pro Asn Ile Gly Ser Arg Pro Arg<br>    225                 230              235 | 720 | |
| gta agg aat cag agc ggc agg ata agc atc tac tgg acc cta gta aac<br>Val Arg Asn Gln Ser Gly Arg Ile Ser Ile Tyr Trp Thr Leu Val Asn<br>240                    245                 250              255 | 768 | |
| cca ggg gac tcc atc att ttc aac agt att ggg aat ttg att gca cca<br>Pro Gly Asp Ser Ile Ile Phe Asn Ser Ile Gly Asn Leu Ile Ala Pro<br>                260                 265              270 | 816 | |
| aga ggc cac tac aaa ata agc aaa tct act aag agc aca gtg ctt aaa<br>Arg Gly His Tyr Lys Ile Ser Lys Ser Thr Lys Ser Thr Val Leu Lys<br>            275                 280              285 | 864 | |
| agt gac aaa agg att ggg tca tgc aca agc cct tgc tta act gat aaa<br>Ser Asp Lys Arg Ile Gly Ser Cys Thr Ser Pro Cys Leu Thr Asp Lys<br>        290                 295              300 | 912 | |
| ggt tcg atc caa agt gac aaa cct ttt cag aat gta tca agg att gct<br>Gly Ser Ile Gln Ser Asp Lys Pro Phe Gln Asn Val Ser Arg Ile Ala<br>    305                 310              315 | 960 | |

```
ata gga aac tgc ccg aaa tat gta aag caa ggg tcc ctg atg tta gca    1008
Ile Gly Asn Cys Pro Lys Tyr Val Lys Gln Gly Ser Leu Met Leu Ala
320                 325                 330                 335 act gga atg cgc aac atc cct ggc aaa cag gca aag ggc tta ttt ggg    1056
Thr Gly Met Arg Asn Ile Pro Gly Lys Gln Ala Lys Gly Leu Phe Gly
            340                 345                 350 gca att gct gga ttc att gaa aat ggt tgg caa ggc ctg att gat ggg    1104
Ala Ile Ala Gly Phe Ile Glu Asn Gly Trp Gln Gly Leu Ile Asp Gly
        355                 360                 365 tgg tat gga ttc agg cac caa aat gct gaa gga aca gga act gct gca    1152
Trp Tyr Gly Phe Arg His Gln Asn Ala Glu Gly Thr Gly Thr Ala Ala
    370                 375                 380 gac ctg aag tca act cag gca gcc att gat cag ata aat ggc aag ctg    1200
Asp Leu Lys Ser Thr Gln Ala Ala Ile Asp Gln Ile Asn Gly Lys Leu
385                 390                 395 aac aga ttg ata gag aag aca aat gaa aaa tat cac caa ata gaa aag    1248
Asn Arg Leu Ile Glu Lys Thr Asn Glu Lys Tyr His Gln Ile Glu Lys
400                 405                 410                 415 gaa ttc gaa cag gtg gaa gga aga ata caa gac ctt gag aag tac gtt    1296
Glu Phe Glu Gln Val Glu Gly Arg Ile Gln Asp Leu Glu Lys Tyr Val
            420                 425                 430 gag gac act aag att gat ttg tgg tca tac aat gct gaa ttg cta gta    1344
Glu Asp Thr Lys Ile Asp Leu Trp Ser Tyr Asn Ala Glu Leu Leu Val
        435                 440                 445 gca cta gag aat cag cac aca ata gat gtc aca gac tcc gaa atg aac    1392
Ala Leu Glu Asn Gln His Thr Ile Asp Val Thr Asp Ser Glu Met Asn
    450                 455                 460 aag ctt ttt gaa aga gta aga agg caa tta aga gag aat gca gaa gat    1440
Lys Leu Phe Glu Arg Val Arg Arg Gln Leu Arg Glu Asn Ala Glu Asp
465                 470                 475 caa ggc aac ggt tgt ttc gag ata ttc cat cag tgt gac aac aat tgt    1488
Gln Gly Asn Gly Cys Phe Glu Ile Phe His Gln Cys Asp Asn Asn Cys
480                 485                 490                 495 ata gaa agc att aga aac gga act tat gac cac aac atc tac agg gat    1536
Ile Glu Ser Ile Arg Asn Gly Thr Tyr Asp His Asn Ile Tyr Arg Asp
            500                 505                 510 gaa gcc atc aac aat cga atc aaa ata aat cct gtc act ttg acg atg    1584
Glu Ala Ile Asn Asn Arg Ile Lys Ile Asn Pro Val Thr Leu Thr Met
        515                 520                 525 ggg tac aag gac ata atc ctg tgg att tct ttc tcc atg tca tgc ttt    1632
Gly Tyr Lys Asp Ile Ile Leu Trp Ile Ser Phe Ser Met Ser Cys Phe
    530                 535                 540 gtc ttc gtg gca ctg att ctg gga ttt gtt cta tgg gct tgt caa aac    1680
Val Phe Val Ala Leu Ile Leu Gly Phe Val Leu Trp Ala Cys Gln Asn
545                 550                 555 ggg aat atc cga tgc caa atc tgt ata taa agaa                       1714
Gly Asn Ile Arg Cys Gln Ile Cys Ile
560                 565

<210> SEQ ID NO 32
<211> LENGTH: 568
<212> TYPE: PRT
<213> ORGANISM: Influenza A virus

<400> SEQUENCE: 32

Met Ile Ala Leu Ile Leu Val Ala Leu Ala Leu Ser His Thr Ala Tyr
1               5                   10                  15

Ser Gln Ile Thr Asn Gly Thr Thr Gly Asn Pro Ile Ile Cys Leu Gly
            20                  25                  30

His His Ala Val Glu Asn Gly Thr Ser Val Lys Thr Leu Thr Asp Asn
```

```
                35                  40                  45
His Val Glu Val Val Ser Ala Lys Glu Leu Val Glu Thr Asn His Thr
 50                  55                  60

Asp Glu Leu Cys Pro Ser Pro Leu Lys Leu Val Asp Gly Gln Asp Cys
 65                  70                  75                  80

Asp Leu Ile Asn Gly Ala Leu Gly Ser Pro Gly Cys Asp Arg Leu Gln
                 85                  90                  95

Asp Thr Thr Trp Asp Val Phe Ile Glu Arg Pro Thr Ala Val Asp Thr
                100                 105                 110

Cys Tyr Pro Phe Asp Val Pro Asp Tyr Gln Ser Leu Arg Ser Ile Leu
                115                 120                 125

Ala Ser Ser Gly Ser Leu Glu Phe Ile Ala Glu Gln Phe Thr Trp Asn
130                 135                 140

Gly Val Lys Val Asp Gly Ser Ser Ala Cys Leu Arg Gly Gly Arg
145                 150                 155                 160

Asn Ser Phe Phe Ser Arg Leu Asn Trp Leu Thr Lys Glu Thr Asn Gly
                165                 170                 175

Asn Tyr Gly Pro Ile Asn Val Thr Lys Glu Asn Thr Gly Ser Tyr Val
                180                 185                 190

Arg Leu Tyr Leu Trp Gly Val His His Pro Ser Ser Asp Asn Glu Gln
                195                 200                 205

Thr Asp Leu Tyr Lys Val Ala Thr Gly Arg Val Thr Val Ser Thr Arg
210                 215                 220

Ser Asp Gln Ile Ser Ile Val Pro Asn Ile Gly Ser Arg Pro Arg Val
225                 230                 235                 240

Arg Asn Gln Ser Gly Arg Ile Ser Ile Tyr Trp Thr Leu Val Asn Pro
                245                 250                 255

Gly Asp Ser Ile Ile Phe Asn Ser Ile Gly Asn Leu Ile Ala Pro Arg
                260                 265                 270

Gly His Tyr Lys Ile Ser Lys Ser Thr Lys Ser Thr Val Leu Lys Ser
                275                 280                 285

Asp Lys Arg Ile Gly Ser Cys Thr Ser Pro Cys Leu Thr Asp Lys Gly
290                 295                 300

Ser Ile Gln Ser Asp Lys Pro Phe Gln Asn Val Ser Arg Ile Ala Ile
305                 310                 315                 320

Gly Asn Cys Pro Lys Tyr Val Lys Gln Gly Ser Leu Met Leu Ala Thr
                325                 330                 335

Gly Met Arg Asn Ile Pro Gly Leu Gln Ala Lys Gly Leu Phe Gly Ala
                340                 345                 350

Ile Ala Gly Phe Ile Glu Asn Gly Trp Gln Gly Leu Ile Asp Gly Trp
                355                 360                 365

Tyr Gly Phe Arg His Gln Asn Ala Glu Gly Thr Gly Thr Ala Ala Asp
                370                 375                 380

Leu Lys Ser Thr Gln Ala Ala Ile Asp Gln Ile Asn Gly Lys Leu Asn
385                 390                 395                 400

Arg Leu Ile Glu Lys Thr Asn Glu Lys Tyr His Gln Ile Glu Lys Glu
                405                 410                 415

Phe Glu Gln Val Glu Gly Arg Ile Gln Asp Leu Glu Lys Tyr Val Glu
                420                 425                 430

Asp Thr Lys Ile Asp Leu Trp Ser Tyr Asn Ala Glu Leu Leu Val Ala
                435                 440                 445

Leu Glu Asn Gln His Thr Ile Asp Val Thr Asp Ser Glu Met Asn Lys
450                 455                 460
```

```
Leu Phe Glu Arg Val Arg Arg Gln Leu Arg Glu Asn Ala Glu Asp Gln
465                 470                 475                 480

Gly Asn Gly Cys Phe Glu Ile Phe His Gln Cys Asp Asn Asn Cys Ile
            485                 490                 495

Glu Ser Ile Arg Asn Gly Thr Tyr Asp His Asn Ile Tyr Arg Asp Glu
        500                 505                 510

Ala Ile Asn Asn Arg Ile Lys Ile Asn Pro Val Thr Leu Thr Met Gly
    515                 520                 525

Tyr Lys Asp Ile Ile Leu Trp Ile Ser Phe Ser Met Ser Cys Phe Val
530                 535                 540

Phe Val Ala Leu Ile Leu Gly Phe Val Leu Trp Ala Cys Gln Asn Gly
545                 550                 555                 560

Asn Ile Arg Cys Gln Ile Cys Ile
                565
```

<210> SEQ ID NO 33
<211> LENGTH: 1728
<212> TYPE: DNA
<213> ORGANISM: Influenza A virus
<220> FEATURE:
<221> NAME/KEY: CDS
<222> LOCATION: (8)..(1720)
<223> OTHER INFORMATION:

<400> SEQUENCE: 33

```
aaacaaa atg aac act caa atc atc gtc att cta gtc ctc gga ctg tcg        49
        Met Asn Thr Gln Ile Ile Val Ile Leu Val Leu Gly Leu Ser
        1               5                   10 atg gtg aga tct gac aag att tgt ctc ggg cac cat gcc gta gca aat        97
Met Val Arg Ser Asp Lys Ile Cys Leu Gly His His Ala Val Ala Asn
15              20                  25                  30 ggg aca aaa gtc aac aca cta act gag aaa gga gtg gaa gtg tca aat       145
Gly Thr Lys Val Asn Thr Leu Thr Glu Lys Gly Val Glu Val Ser Asn
                35                  40                  45 gcc acg gag aca gtg gag att aca gga ata aat aaa gtg tgc aca aaa       193
Ala Thr Glu Thr Val Glu Ile Thr Gly Ile Asn Lys Val Cys Thr Lys
            50                  55                  60 ggg aag aaa gcg gtg gac ttg gga tct tgt gga ata ctg gga act atc       241
Gly Lys Lys Ala Val Asp Leu Gly Ser Cys Gly Ile Leu Gly Thr Ile
        65                  70                  75 att ggg cct cca caa tgt gac tct cat ctt aaa ttc aaa gct gat ctg       289
Ile Gly Pro Pro Gln Cys Asp Ser His Leu Lys Phe Lys Ala Asp Leu
80                  85                  90 ata ata gaa aga aga aat tca agt gac atc tgt tac cca ggg aaa ttc       337
Ile Ile Glu Arg Arg Asn Ser Ser Asp Ile Cys Tyr Pro Gly Lys Phe
95                  100                 105                 110 act aat gag gaa gca ctg aga caa ata atc aga gaa tct ggt gga att       385
Thr Asn Glu Glu Ala Leu Arg Gln Ile Ile Arg Glu Ser Gly Gly Ile
                115                 120                 125 gac aaa gag cca atg gga ttt aga tat tca gga ata aaa aca gac ggg       433
Asp Lys Glu Pro Met Gly Phe Arg Tyr Ser Gly Ile Lys Thr Asp Gly
            130                 135                 140 gca acc agt gcg tgt aag aga aca gtg tcc tct ttc tac tca gaa atg       481
Ala Thr Ser Ala Cys Lys Arg Thr Val Ser Ser Phe Tyr Ser Glu Met
        145                 150                 155 aaa tgg ctt tta tcc agc aag gat aac cag gtg ttc cca caa ctg aat       529
Lys Trp Leu Leu Ser Ser Lys Asp Asn Gln Val Phe Pro Gln Leu Asn
    160                 165                 170 cag aca tac agg aac aac aga aaa gaa cca gcc cta att gtt tgg gga       577
Gln Thr Tyr Arg Asn Asn Arg Lys Glu Pro Ala Leu Ile Val Trp Gly
175                 180                 185                 190
```

```
gta cat cat tca agc tcc ttg gat gag caa aat aag cta tat gga gct      625
Val His His Ser Ser Ser Leu Asp Glu Gln Asn Lys Leu Tyr Gly Ala
            195                 200                 205 ggg aac aag ctg ata aca gta gga agc tca aaa tac caa caa tcg ttt      673
Gly Asn Lys Leu Ile Thr Val Gly Ser Ser Lys Tyr Gln Gln Ser Phe
        210                 215                 220 tca cca agt cca ggg gac agg ccc aaa gtg aat ggt cag gcc ggg agg      721
Ser Pro Ser Pro Gly Asp Arg Pro Lys Val Asn Gly Gln Ala Gly Arg
                225                 230                 235 atc gac ttt cat tgg atg cta ttg gac cca ggg gat aca gtc act ttt      769
Ile Asp Phe His Trp Met Leu Leu Asp Pro Gly Asp Thr Val Thr Phe
            240                 245                 250 acc ttc aat ggt gca ttc ata gcc cca gat aga gcc acc ttt ctc cgc      817
Thr Phe Asn Gly Ala Phe Ile Ala Pro Asp Arg Ala Thr Phe Leu Arg
255                 260                 265                 270 tct aat gcc cca tcg gga gtt gag tac aat ggg aag tca ctg gga ata      865
Ser Asn Ala Pro Ser Gly Val Glu Tyr Asn Gly Lys Ser Leu Gly Ile
                275                 280                 285 cag agt gat gca caa att gat gaa tca tgt gaa ggg gaa tgc ttc tac      913
Gln Ser Asp Ala Gln Ile Asp Glu Ser Cys Glu Gly Glu Cys Phe Tyr
            290                 295                 300 agt gga ggg aca ata aac agc cct ttg cca ttt caa aac atc gat agt      961
Ser Gly Gly Thr Ile Asn Ser Pro Leu Pro Phe Gln Asn Ile Asp Ser
        305                 310                 315 tgg gct gtc gga agg tgc ccc aga tat gta aag caa tca agc ctg ccg     1009
Trp Ala Val Gly Arg Cys Pro Arg Tyr Val Lys Gln Ser Ser Leu Pro
320                 325                 330 ctg gcc tta gga atg aaa aat gta cca gag aaa ata cat act agg gga     1057
Leu Ala Leu Gly Met Lys Asn Val Pro Glu Lys Ile His Thr Arg Gly
335                 340                 345                 350 ctg ttc ggt gca att gca gga ttc atc gag aat gga tgg gaa gga ctc     1105
Leu Phe Gly Ala Ile Ala Gly Phe Ile Glu Asn Gly Trp Glu Gly Leu
            355                 360                 365 att gat gga tgg tat gga ttt agg cat cag aat gca cag ggg cag gga     1153
Ile Asp Gly Trp Tyr Gly Phe Arg His Gln Asn Ala Gln Gly Gln Gly
        370                 375                 380 aca gct gct gac tac aag agt act cag gct gca att gac cag ata aca     1201
Thr Ala Ala Asp Tyr Lys Ser Thr Gln Ala Ala Ile Asp Gln Ile Thr
            385                 390                 395 ggg aaa ctt aat aga tta att gaa aaa acc aac aca cag ttt gaa ctc     1249
Gly Lys Leu Asn Arg Leu Ile Glu Lys Thr Asn Thr Gln Phe Glu Leu
        400                 405                 410 ata gac aat gag ttc act gaa gtg gag cag cag ata ggc aat gta ata     1297
Ile Asp Asn Glu Phe Thr Glu Val Glu Gln Gln Ile Gly Asn Val Ile
415                 420                 425                 430 aac tgg aca agg gac tcc ttg act gag atc tgg tca tac aat gct gaa     1345
Asn Trp Thr Arg Asp Ser Leu Thr Glu Ile Trp Ser Tyr Asn Ala Glu
                435                 440                 445 ctt cta gta gca atg gaa aat cag cat aca att gac ctt gca gat tct     1393
Leu Leu Val Ala Met Glu Asn Gln His Thr Ile Asp Leu Ala Asp Ser
            450                 455                 460 gaa atg aac aaa ctc tat gag aga gtg aga aga cag cta agg gag aat     1441
Glu Met Asn Lys Leu Tyr Glu Arg Val Arg Arg Gln Leu Arg Glu Asn
        465                 470                 475 gcc gag gag gat gga act gga tgt ttt gag att ttc cac cga tgt gac     1489
Ala Glu Glu Asp Gly Thr Gly Cys Phe Glu Ile Phe His Arg Cys Asp
            480                 485                 490 gat caa tgt atg gag agc ata cga aat aat act tac aat cac act gaa     1537
Asp Gln Cys Met Glu Ser Ile Arg Asn Asn Thr Tyr Asn His Thr Glu
495                 500                 505                 510
```

```
tat cga cag gaa gcc tta cag aat agg ata atg atc aat ccg gta aag    1585
Tyr Arg Gln Glu Ala Leu Gln Asn Arg Ile Met Ile Asn Pro Val Lys
                515                 520                 525 ctt agt ggt ggg tac aaa gat gtg ata cta tgg ttt agc ttc ggg gca    1633
Leu Ser Gly Gly Tyr Lys Asp Val Ile Leu Trp Phe Ser Phe Gly Ala
            530                 535                 540 tca tgt gta atg ctt cta gcc att gct atg ggt ctt att ttc atg tgt    1681
Ser Cys Val Met Leu Leu Ala Ile Ala Met Gly Leu Ile Phe Met Cys
        545                 550                 555 gtg aaa aac ggg aat ctg cgg tgc act atc tgt ata taa ttatttga       1728
Val Lys Asn Gly Asn Leu Arg Cys Thr Ile Cys Ile
    560                 565                 570

<210> SEQ ID NO 34
<211> LENGTH: 570
<212> TYPE: PRT
<213> ORGANISM: Influenza A virus

<400> SEQUENCE: 34

Met Asn Thr Gln Ile Ile Val Ile Leu Val Leu Gly Leu Ser Met Val
1               5                   10                  15

Arg Ser Asp Lys Ile Cys Leu Gly His His Ala Val Ala Asn Gly Thr
            20                  25                  30

Lys Val Asn Thr Leu Thr Glu Lys Gly Val Glu Val Val Asn Ala Thr
        35                  40                  45

Glu Thr Val Glu Ile Thr Gly Ile Asn Lys Val Cys Thr Lys Gly Lys
    50                  55                  60

Lys Ala Val Asp Leu Gly Ser Cys Gly Ile Leu Gly Thr Ile Ile Gly
65                  70                  75                  80

Pro Pro Gln Cys Asp Ser His Leu Lys Phe Lys Ala Asp Leu Ile Ile
                85                  90                  95

Glu Arg Arg Asn Ser Ser Asp Ile Cys Tyr Pro Gly Lys Phe Thr Asn
            100                 105                 110

Glu Glu Ala Leu Arg Gln Ile Ile Arg Glu Ser Gly Gly Ile Asp Lys
        115                 120                 125

Glu Pro Met Gly Phe Arg Tyr Ser Gly Ile Lys Thr Asp Gly Ala Thr
    130                 135                 140

Ser Ala Cys Lys Arg Thr Val Ser Ser Phe Tyr Ser Glu Met Lys Trp
145                 150                 155                 160

Leu Leu Ser Ser Lys Asp Asn Gln Val Phe Pro Gln Leu Asn Gln Thr
                165                 170                 175

Tyr Arg Asn Asn Arg Lys Glu Pro Ala Leu Ile Val Trp Gly Val His
            180                 185                 190

His Ser Ser Ser Leu Asp Glu Gln Asn Lys Leu Tyr Gly Ala Gly Asn
        195                 200                 205

Lys Leu Ile Thr Val Gly Ser Ser Lys Tyr Gln Gln Ser Phe Ser Pro
    210                 215                 220

Ser Pro Gly Asp Arg Pro Lys Val Asn Gly Gln Ala Gly Arg Ile Asp
225                 230                 235                 240

Phe His Trp Met Leu Leu Asp Pro Gly Asp Thr Val Thr Phe Thr Phe
                245                 250                 255

Asn Gly Ala Phe Ile Ala Pro Arg Ala Thr Phe Leu Arg Ser Asn
            260                 265                 270

Ala Pro Ser Gly Val Glu Tyr Asn Gly Lys Ser Leu Gly Ile Gln Ser
        275                 280                 285

Asp Ala Gln Ile Asp Glu Ser Cys Glu Gly Glu Cys Phe Tyr Ser Gly
```

```
                  290                 295                 300
Gly Thr Ile Asn Ser Pro Leu Pro Phe Gln Asn Ile Asp Ser Trp Ala
305                 310                 315                 320

Val Gly Arg Cys Pro Arg Tyr Val Lys Gln Ser Ser Leu Pro Leu Ala
                325                 330                 335

Leu Gly Met Lys Asn Val Pro Glu Lys Ile His Thr Arg Gly Leu Phe
                340                 345                 350

Gly Ala Ile Ala Gly Phe Ile Glu Asn Gly Trp Glu Gly Leu Ile Asp
                355                 360                 365

Gly Trp Tyr Gly Phe Arg His Gln Asn Ala Gln Gly Gln Gly Thr Ala
                370                 375                 380

Ala Asp Tyr Lys Ser Thr Gln Ala Ala Ile Asp Gln Ile Thr Gly Lys
385                 390                 395                 400

Leu Asn Arg Leu Ile Glu Lys Thr Asn Thr Gln Phe Glu Leu Ile Asp
                405                 410                 415

Asn Glu Phe Thr Glu Val Glu Gln Gln Ile Gly Asn Val Ile Asn Trp
                420                 425                 430

Thr Arg Asp Ser Leu Thr Glu Ile Trp Ser Tyr Asn Ala Glu Leu Leu
                435                 440                 445

Val Ala Met Glu Asn Gln His Thr Ile Asp Leu Ala Asp Ser Glu Met
                450                 455                 460

Asn Lys Leu Tyr Glu Arg Val Arg Arg Gln Leu Arg Glu Asn Ala Glu
465                 470                 475                 480

Glu Asp Gly Thr Gly Cys Phe Glu Ile Phe His Arg Cys Asp Asp Gln
                485                 490                 495

Cys Met Glu Ser Ile Arg Asn Asn Thr Tyr Asn His Thr Glu Tyr Arg
                500                 505                 510

Gln Glu Ala Leu Gln Asn Arg Ile Met Ile Asn Pro Val Lys Leu Ser
                515                 520                 525

Gly Gly Tyr Lys Asp Val Ile Leu Trp Phe Ser Phe Gly Ala Ser Cys
                530                 535                 540

Val Met Leu Leu Ala Ile Ala Met Gly Leu Ile Phe Met Cys Val Lys
545                 550                 555                 560

Asn Gly Asn Leu Arg Cys Thr Ile Cys Ile
                565                 570

<210> SEQ ID NO 35
<211> LENGTH: 1779
<212> TYPE: DNA
<213> ORGANISM: Influenza A virus
<220> FEATURE:
<221> NAME/KEY: CDS
<222> LOCATION: (29)..(1735)
<223> OTHER INFORMATION:

<400> SEQUENCE: 35
agcaaaagca ggggtctaat ctattaaa atg gag aga ata gtg ctt ttt ctt        52
                                 Met Glu Arg Ile Val Leu Phe Leu
                                  1               5 gca ata gtc agt ctt gtc aaa agt gac cag att tgc att ggt tat cat       100
Ala Ile Val Ser Leu Val Lys Ser Asp Gln Ile Cys Ile Gly Tyr His
         10                  15                  20 gca aat aac tcg aca gaa cag gtt gac aca ata atg gag aag aat gtg       148
Ala Asn Asn Ser Thr Glu Gln Val Asp Thr Ile Met Glu Lys Asn Val
 25                  30                  35                  40 act gtc aca cat gcc caa gac ata ctc gaa aag aca cac aac ggg aag       196
Thr Val Thr His Ala Gln Asp Ile Leu Glu Lys Thr His Asn Gly Lys
                 45                  50                  55
```

```
ctc tgc agt cta aat gga gtg aag cct ctc atc ttg agg gat tgt agt      244
Leu Cys Ser Leu Asn Gly Val Lys Pro Leu Ile Leu Arg Asp Cys Ser
         60                  65                  70 gta gct gga tgg ctc ctt gga aat ccc atg tgt gac gag ttc ctt aat      292
Val Ala Gly Trp Leu Leu Gly Asn Pro Met Cys Asp Glu Phe Leu Asn
     75                  80                  85 gtg cca gaa tgg tct tac ata gtg gag aag gac aat cca atc aac agc      340
Val Pro Glu Trp Ser Tyr Ile Val Glu Lys Asp Asn Pro Ile Asn Ser
 90                  95                 100 ctt tgc tac cca ggg gac ttt aat gac tac gaa gaa ttg aaa cac cta      388
Leu Cys Tyr Pro Gly Asp Phe Asn Asp Tyr Glu Glu Leu Lys His Leu
105                 110                 115                 120 ttg agc agt aca aac cac ttt gag aaa att caa atc atc ccc agg agt      436
Leu Ser Ser Thr Asn His Phe Glu Lys Ile Gln Ile Ile Pro Arg Ser
                125                 130                 135 tct tgg tcc aat cat gat gcc tca tca gga gta agc tct gca tgt cca      484
Ser Trp Ser Asn His Asp Ala Ser Ser Gly Val Ser Ser Ala Cys Pro
             140                 145                 150 tac aat ggg agg tcc tcc ttt ttt aga aat gtg gta tgg ctt atc gaa      532
Tyr Asn Gly Arg Ser Ser Phe Phe Arg Asn Val Val Trp Leu Ile Glu
         155                 160                 165 aag aac aat gca tac cca aca ata aag agg agt tac aac aat acc aac      580
Lys Asn Asn Ala Tyr Pro Thr Ile Lys Arg Ser Tyr Asn Asn Thr Asn
     170                 175                 180 caa gag gat ctt cta ata ttg tgg ggg att cac cat cct aat gac gca      628
Gln Glu Asp Leu Leu Ile Leu Trp Gly Ile His His Pro Asn Asp Ala
185                 190                 195                 200 gca gaa cag aca aag ctc tat caa aat cca acc act tat gtc tct gtc      676
Ala Glu Gln Thr Lys Leu Tyr Gln Asn Pro Thr Thr Tyr Val Ser Val
                205                 210                 215 ggg aca tca aca ctg aat cag aga tca att cca gaa ata gcc acc agg      724
Gly Thr Ser Thr Leu Asn Gln Arg Ser Ile Pro Glu Ile Ala Thr Arg
             220                 225                 230 ccc aaa gta aat gga cag agc gga aga gtg gaa ttc ttt tgg aca att      772
Pro Lys Val Asn Gly Gln Ser Gly Arg Val Glu Phe Phe Trp Thr Ile
         235                 240                 245 tta aag ccc aat gat gca att aat ttt gag agt aat ggg aac ttc ata      820
Leu Lys Pro Asn Asp Ala Ile Asn Phe Glu Ser Asn Gly Asn Phe Ile
     250                 255                 260 gct cca gaa tat gca tac aaa att gtc aag aag ggg gac tct gca atc      868
Ala Pro Glu Tyr Ala Tyr Lys Ile Val Lys Lys Gly Asp Ser Ala Ile
265                 270                 275                 280 atg aaa agc gat ttg gaa tat ggt aac tgt aat gct aag tgt caa act      916
Met Lys Ser Asp Leu Glu Tyr Gly Asn Cys Asn Ala Lys Cys Gln Thr
                285                 290                 295 cca gtg ggt gcg ata aac tcc agc atg ccc ttc cac aat ata cac cct      964
Pro Val Gly Ala Ile Asn Ser Ser Met Pro Phe His Asn Ile His Pro
             300                 305                 310 ctc acc atc ggg gaa tgc ccc aaa tac gta aaa tca gat agg ttg gtc     1012
Leu Thr Ile Gly Glu Cys Pro Lys Tyr Val Lys Ser Asp Arg Leu Val
         315                 320                 325 ctt gca act ggg ctc agg aac gtc cct cag agg gag acg cgc agg cag     1060
Leu Ala Thr Gly Leu Arg Asn Val Pro Gln Arg Glu Thr Arg Arg Gln
     330                 335                 340 aaa aga ggt cta ttt ggg gct ata gca ggt ttt ata gaa ggg gga tgg     1108
Lys Arg Gly Leu Phe Gly Ala Ile Ala Gly Phe Ile Glu Gly Gly Trp
345                 350                 355                 360 cag gga atg gta gac ggt tgg tat gga tac cat cat agc aac gag cag     1156
Gln Gly Met Val Asp Gly Trp Tyr Gly Tyr His His Ser Asn Glu Gln
                365                 370                 375
```

```
ggg agc ggg tat gct gcg gac aaa gag tcc act caa aag gca att gat    1204
Gly Ser Gly Tyr Ala Ala Asp Lys Glu Ser Thr Gln Lys Ala Ile Asp
        380                 385                 390 ggg atc acc aat aag gtc aac tca atc att gac aaa atg aac act caa    1252
Gly Ile Thr Asn Lys Val Asn Ser Ile Ile Asp Lys Met Asn Thr Gln
        395                 400                 405 ttt gag acc gtt gga aag gaa ttt aat aat ttg gag agg agg ata gag    1300
Phe Glu Thr Val Gly Lys Glu Phe Asn Asn Leu Glu Arg Arg Ile Glu
410                 415                 420 aat ttg aac aag aaa atg gaa gac ggg ttt cta gat gtc tgg act tac    1348
Asn Leu Asn Lys Lys Met Glu Asp Gly Phe Leu Asp Val Trp Thr Tyr
425                 430                 435                 440 aat gcc gaa ctt cta gtt ctc atg gaa aat gaa agg act ctg gat ttt    1396
Asn Ala Glu Leu Leu Val Leu Met Glu Asn Glu Arg Thr Leu Asp Phe
                445                 450                 455 cat gac tca aac gtc aaa aac ctt tat gat aaa gtc cga cta cag ctt    1444
His Asp Ser Asn Val Lys Asn Leu Tyr Asp Lys Val Arg Leu Gln Leu
                460                 465                 470 aag gat aat gct aag gaa ctg ggt aat ggt tgt ttc gag ttc tac cat    1492
Lys Asp Asn Ala Lys Glu Leu Gly Asn Gly Cys Phe Glu Phe Tyr His
        475                 480                 485 aaa tgt gac aat gaa tgt atg gaa agc gtg aga aac ggg aca tat gac    1540
Lys Cys Asp Asn Glu Cys Met Glu Ser Val Arg Asn Gly Thr Tyr Asp
490                 495                 500 tac cca cag tat tca gaa gaa gca aga ctg aac aga gag gaa ata agt    1588
Tyr Pro Gln Tyr Ser Glu Glu Ala Arg Leu Asn Arg Glu Glu Ile Ser
505                 510                 515                 520 ggg gtt aaa ttg gaa tta atg gga gtt tac caa ata ctg tca att tat    1636
Gly Val Lys Leu Glu Leu Met Gly Val Tyr Gln Ile Leu Ser Ile Tyr
                525                 530                 535 tca aca gtg gca agt tcc cta gca ctg gca atc atg ata gct ggt cta    1684
Ser Thr Val Ala Ser Ser Leu Ala Leu Ala Ile Met Ile Ala Gly Leu
                540                 545                 550 tct ttt tgg atg tgt tcc aat gga tca ttg cag tgc aga att tgc att    1732
Ser Phe Trp Met Cys Ser Asn Gly Ser Leu Gln Cys Arg Ile Cys Ile
        555                 560                 565 taa atttatgagt tcagattgta gttaaaaaca cccttgtttc tact              1779

<210> SEQ ID NO 36
<211> LENGTH: 568
<212> TYPE: PRT
<213> ORGANISM: Influenza A virus

<400> SEQUENCE: 36

Met Glu Arg Ile Val Leu Phe Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Ile Asn Ser Leu Cys Tyr Pro Gly Asp Phe Asn
            100                 105                 110
```

```
Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asn His Asp Ala Ser
130                 135                 140

Ser Gly Val Ser Ser Ala Cys Pro Tyr Asn Gly Arg Ser Ser Phe Phe
145                 150                 155                 160

Arg Asn Val Val Trp Leu Ile Glu Lys Asn Asn Ala Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Ser Gly
225                 230                 235                 240

Arg Val Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Asp Leu Glu Tyr Gly
        275                 280                 285

Asn Cys Asn Ala Lys Cys Gln Thr Pro Val Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Glu Thr Arg Arg Gln Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Ile Thr Asn Lys Val Asn Ser
385                 390                 395                 400

Ile Ile Asp Lys Met Asn Thr Gln Phe Glu Thr Val Gly Lys Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Lys Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Leu Met Gly
        515                 520                 525

Val Tyr Gln Ile Leu Ser Ile Tyr Ser Thr Val Ala Ser Ser Leu Ala
530                 535                 540
```

```
Leu Ala Ile Met Ile Ala Gly Leu Ser Phe Trp Met Cys Ser Asn Gly
545                 550                 555                 560

Ser Leu Gln Cys Arg Ile Cys Ile
                565

<210> SEQ ID NO 37
<211> LENGTH: 1665
<212> TYPE: DNA
<213> ORGANISM: Influenza A virus
<220> FEATURE:
<221> NAME/KEY: CDS
<222> LOCATION: (1)..(1665)
<223> OTHER INFORMATION:

<400> SEQUENCE: 37 atg gag aaa ata gtg ctt ctt ctt gca aca gtc agt ctt gtt aaa agt      48
Met Glu Lys Ile Val Leu Leu Leu Ala Thr Val Ser Leu Val Lys Ser
1               5                   10                  15 gac cag att tgc att ggt tac cat gca aac aac tcg aca gag cag gtt      96
Asp Gln Ile Cys Ile Gly Tyr His Ala Asn Asn Ser Thr Glu Gln Val
            20                  25                  30 gac aca ata atg gaa aag aat gtt act gtt aca cat gcc caa gac ata     144
Asp Thr Ile Met Glu Lys Asn Val Thr Val Thr His Ala Gln Asp Ile
        35                  40                  45 ctg gaa agg aca cac aac ggg aag ctc tgc gat cta aat gga gtg aag     192
Leu Glu Arg Thr His Asn Gly Lys Leu Cys Asp Leu Asn Gly Val Lys
    50                  55                  60 cct ctg att ttg agg gat tgt agt gta gct gga tgg ctc ctc gga aac     240
Pro Leu Ile Leu Arg Asp Cys Ser Val Ala Gly Trp Leu Leu Gly Asn
65                  70                  75                  80 cct atg tgt gac gaa ttc atc aat gtg ccg gaa tgg tct tac ata gtg     288
Pro Met Cys Asp Glu Phe Ile Asn Val Pro Glu Trp Ser Tyr Ile Val
                85                  90                  95 gag aag gcc agt cca gcc aat gac ctc tgt tat cca ggg aat ttc aac     336
Glu Lys Ala Ser Pro Ala Asn Asp Leu Cys Tyr Pro Gly Asn Phe Asn
            100                 105                 110 gac tat gaa gaa ctg aaa cac cta ttg agc aga ata aac cat ttt gag     384
Asp Tyr Glu Glu Leu Lys His Leu Leu Ser Arg Ile Asn His Phe Glu
        115                 120                 125 aaa att cag atc atc ccc aaa agt tct tgg tcc aat cat gat gcc tca     432
Lys Ile Gln Ile Ile Pro Lys Ser Ser Trp Ser Asn His Asp Ala Ser
    130                 135                 140 tca ggg gta agc tca gca tgt cca tac ctt ggg aag tcc tcc ttt ttc     480
Ser Gly Val Ser Ser Ala Cys Pro Tyr Leu Gly Lys Ser Ser Phe Phe
145                 150                 155                 160 aga aat gtg gta tgg ctt atc aaa aag aac agt aca tac cca aca ata     528
Arg Asn Val Val Trp Leu Ile Lys Lys Asn Ser Thr Tyr Pro Thr Ile
                165                 170                 175 aag agg agc tac aat aat acc aac caa gaa gat ctt ttg gta ctg tgg     576
Lys Arg Ser Tyr Asn Asn Thr Asn Gln Glu Asp Leu Leu Val Leu Trp
            180                 185                 190 ggg att cac cat cct aat gat gcg gca gag cag aca aag ctc tat caa     624
Gly Ile His His Pro Asn Asp Ala Ala Glu Gln Thr Lys Leu Tyr Gln
        195                 200                 205 aac cca acc acc tac att tcc gtt gga aca tca aca ctg aac cag aga     672
Asn Pro Thr Thr Tyr Ile Ser Val Gly Thr Ser Thr Leu Asn Gln Arg
    210                 215                 220 ttg gtt cca gaa ata gct act aga ccc aaa gta aac ggg caa agt gga     720
Leu Val Pro Glu Ile Ala Thr Arg Pro Lys Val Asn Gly Gln Ser Gly
225                 230                 235                 240 aga ata gag ttc ttc tgg aca att tta aag ccg aat gat gcc atc aat     768
Arg Ile Glu Phe Phe Trp Thr Ile Leu Lys Pro Asn Asp Ala Ile Asn
```

```
Arg Ile Glu Phe Phe Trp Thr Ile Leu Lys Pro Asn Asp Ala Ile Asn
                245                 250                 255 ttc gag agt aat gga aat ttc att gct cca gaa tat gca tac aaa att        816
Phe Glu Ser Asn Gly Asn Phe Ile Ala Pro Glu Tyr Ala Tyr Lys Ile
                260                 265                 270 gtc aag aaa ggg gac tca aca att atg aaa agt gaa ttg gaa tat ggt        864
Val Lys Lys Gly Asp Ser Thr Ile Met Lys Ser Glu Leu Glu Tyr Gly
                275                 280                 285 aac tgc aac acc aag tgt caa act cca atg ggg gcg ata aac tct agt        912
Asn Cys Asn Thr Lys Cys Gln Thr Pro Met Gly Ala Ile Asn Ser Ser
            290                 295                 300 atg cca ttc cac aac ata cac ccc ctc acc atc ggg gaa tgc ccc aaa        960
Met Pro Phe His Asn Ile His Pro Leu Thr Ile Gly Glu Cys Pro Lys
305                 310                 315                 320 tat gtg aaa tca aac aga tta gtc ctt gcg act gga ctc aga aat gcc       1008
Tyr Val Lys Ser Asn Arg Leu Val Leu Ala Thr Gly Leu Arg Asn Ala
                325                 330                 335 cct caa aga gag aga aga aga aaa aag aga gga cta ttt gga gct ata       1056
Pro Gln Arg Glu Arg Arg Arg Lys Lys Arg Gly Leu Phe Gly Ala Ile
                340                 345                 350 gca ggt ttt ata gag gga gga tgg cag gga atg gta gat ggt tgg tat       1104
Ala Gly Phe Ile Glu Gly Gly Trp Gln Gly Met Val Asp Gly Trp Tyr
                355                 360                 365 ggg tac cac cat agc aat gag cag ggg agt gga tac gct gca gac caa       1152
Gly Tyr His His Ser Asn Glu Gln Gly Ser Gly Tyr Ala Ala Asp Gln
            370                 375                 380 gaa tcc act caa aag gca ata gat gga gtc acc aat aag gtc aac tcg       1200
Glu Ser Thr Gln Lys Ala Ile Asp Gly Val Thr Asn Lys Val Asn Ser
385                 390                 395                 400 atc att aac aaa atg aac act cag ttt gag gcc gtt gga agg gaa ttt       1248
Ile Ile Asn Lys Met Asn Thr Gln Phe Glu Ala Val Gly Arg Glu Phe
                405                 410                 415 aat aac ttg gaa agg agg ata gag aat tta aac aag aag atg gaa gac       1296
Asn Asn Leu Glu Arg Arg Ile Glu Asn Leu Asn Lys Lys Met Glu Asp
                420                 425                 430 gga ttc cta gat gtc tgg act tac aat gcc gaa ctt ctg gtt ctc atg       1344
Gly Phe Leu Asp Val Trp Thr Tyr Asn Ala Glu Leu Leu Val Leu Met
                435                 440                 445 gaa aat gag aga act cta gac ttt cat gac tca aat gtc aag aac ctt       1392
Glu Asn Glu Arg Thr Leu Asp Phe His Asp Ser Asn Val Lys Asn Leu
450                 455                 460 tac gac aag gtc cga cta cag ctt agg gat aat gca aag gag ctg ggt       1440
Tyr Asp Lys Val Arg Leu Gln Leu Arg Asp Asn Ala Lys Glu Leu Gly
465                 470                 475                 480 aat ggt tgt ttc gaa ttc tat cac aaa tgt gat aac gaa tgt atg gaa       1488
Asn Gly Cys Phe Glu Phe Tyr His Lys Cys Asp Asn Glu Cys Met Glu
                485                 490                 495 agt gta aaa aac gga acg tat gac tac ccg cag tat tca gaa gaa gca       1536
Ser Val Lys Asn Gly Thr Tyr Asp Tyr Pro Gln Tyr Ser Glu Glu Ala
                500                 505                 510 aga cta aac aga gag gaa ata agt gga gta aaa ttg gaa tca atg gga       1584
Arg Leu Asn Arg Glu Glu Ile Ser Gly Val Lys Leu Glu Ser Met Gly
            515                 520                 525 act tac caa ata ctg tca ctt tat tca aca gtg gcg agt tcc cta gca       1632
Thr Tyr Gln Ile Leu Ser Leu Tyr Ser Thr Val Ala Ser Ser Leu Ala
                530                 535                 540 ctg gca atc atg gta gct ggt cta tct tta tgg                            1665
Leu Ala Ile Met Val Ala Gly Leu Ser Leu Trp
545                 550                 555
```

<210> SEQ ID NO 38
<211> LENGTH: 555
<212> TYPE: PRT
<213> ORGANISM: Influenza A virus

<400> SEQUENCE: 38

```
Met Glu Lys Ile Val Leu Leu Leu Ala Thr Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
    130                 135                 140

Ser Gly Val Ser Ser Ala Cys Pro Tyr Leu Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Glu Ile Ala Thr Arg Pro Lys Val Asn Gly Gln Ser Gly
225                 230                 235                 240

Arg Ile Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ala
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Gln
    370                 375                 380

Glu Ser Thr Gln Lys Ala Ile Asp Gly Val Thr Asn Lys Val Asn Ser
```

```
                385                 390                 395                 400
Ile Ile Asn Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
            485                 490                 495

Ser Val Lys Asn Gly Thr Tyr Asp Tyr Pro Gln Tyr Ser Glu Glu Ala
        500                 505                 510

Arg Leu Asn Arg Glu Glu Ile Ser Gly Val Lys Leu Glu Ser Met Gly
    515                 520                 525

Thr Tyr Gln Ile Leu Ser Leu Tyr Ser Thr Val Ala Ser Ser Leu Ala
    530                 535                 540

Leu Ala Ile Met Val Ala Gly Leu Ser Leu Trp
545                 550                 555

<210> SEQ ID NO 39
<211> LENGTH: 1707
<212> TYPE: DNA
<213> ORGANISM: Influenza A virus
<220> FEATURE:
<221> NAME/KEY: CDS
<222> LOCATION: (1)..(1707)
<223> OTHER INFORMATION:

<400> SEQUENCE: 39 atg gag aaa ata gtg ctt ctt ctt gca ata gtc agt ctt gtt aaa agt        48
Met Glu Lys Ile Val Leu Leu Leu Ala Ile Val Ser Leu Val Lys Ser
1               5                   10                  15 gat cag att tgc atc ggt tac cat gca aac aac

| | |
|---|---|
| tca ggg gtg agc tca gca tgt cca tac cag ggg agg tcc tcc ttt ttc<br>Ser Gly Val Ser Ser Ala Cys Pro Tyr Gln Gly Arg Ser Ser Phe Phe<br>145                        150                            155                        160 | 480 |
| aga aat gtg gta tgg ctc atc aaa aag aac ggt gca tac cca aca ata<br>Arg Asn Val Val Trp Leu Ile Lys Lys Asn Gly Ala Tyr Pro Thr Ile<br>                        165                            170                        175 | 528 |
| aag agg agc tac aat aat acc aat caa gaa gat ctt ttg gta ctg tgg<br>Lys Arg Ser Tyr Asn Asn Thr Asn Gln Glu Asp Leu Leu Val Leu Trp<br>                180                            185                        190 | 576 |
| ggg att cac cat cct aat gat gcg gca gag cag aca aag ctc tat caa<br>Gly Ile His His Pro Asn Asp Ala Ala Glu Gln Thr Lys Leu Tyr Gln<br>        195                            200                        205 | 624 |
| aac cca acc acc tat att tcc gtt gga aca tca aca cta aat cag aga<br>Asn Pro Thr Thr Tyr Ile Ser Val Gly Thr Ser Thr Leu Asn Gln Arg<br>210                        215                            220 | 672 |
| ttg gta cca aaa ata gct act aga tcc aaa gta aac ggg caa agt gga<br>Leu Val Pro Lys Ile Ala Thr Arg Ser Lys Val Asn Gly Gln Ser Gly<br>225                        230                        235                    240 | 720 |
| aga atg gag ttc ttc tgg aca att tta aag ccg aat gat gct atc aac<br>Arg Met Glu Phe Phe Trp Thr Ile Leu Lys Pro Asn Asp Ala Ile Asn<br>                        245                            250                        255 | 768 |
| ttc gag agt aat gga aat ttc att gct cca gaa tat gca tac aaa att<br>Phe Glu Ser Asn Gly Asn Phe Ile Ala Pro Glu Tyr Ala Tyr Lys Ile<br>                260                            265                        270 | 816 |
| gtc aag aaa ggg gac tca gca att atg aaa agt gaa ttg gaa tat ggt<br>Val Lys Lys Gly Asp Ser Ala Ile Met Lys Ser Glu Leu Glu Tyr Gly<br>        275                            280                        285 | 864 |
| aac tgc aac acc aag tgt caa act cca atg ggg gcg ata aac tct agt<br>Asn Cys Asn Thr Lys Cys Gln Thr Pro Met Gly Ala Ile Asn Ser Ser<br>290                        295                            300 | 912 |
| atg cca ttc cac aac ata cac cct ctc acc atc ggg gaa tgc ccc aaa<br>Met Pro Phe His Asn Ile His Pro Leu Thr Ile Gly Glu Cys Pro Lys<br>305                        310                        315                    320 | 960 |
| tat gtg aaa tca aac aga tta gtc ctt gcg aca ggg ctc aga aat agc<br>Tyr Val Lys Ser Asn Arg Leu Val Leu Ala Thr Gly Leu Arg Asn Ser<br>                        325                            330                        335 | 1008 |
| cct caa aga gag aga agg aga aaa aag aga gga ctg ttt gga gct ata<br>Pro Gln Arg Glu Arg Arg Arg Lys Lys Arg Gly Leu Phe Gly Ala Ile<br>        340                            345                        350 | 1056 |
| gca ggt ttt ata gag gga gga tgg cag gga atg gta gat ggt tgg tat<br>Ala Gly Phe Ile Glu Gly Gly Trp Gln Gly Met Val Asp Gly Trp Tyr<br>                355                            360                        365 | 1104 |
| ggg tac cac cat agc aat gag cag ggg agt gga tac gct gca gac aaa<br>Gly Tyr His His Ser Asn Glu Gln Gly Ser Gly Tyr Ala Ala Asp Lys<br>370                        375                            380 | 1152 |
| gaa tcc act caa aag gca ata gat gga gtc acc aat aag gtc aac tcg<br>Glu Ser Thr Gln Lys Ala Ile Asp Gly Val Thr Asn Lys Val Asn Ser<br>385                        390                        395                    400 | 1200 |
| atc att gac aaa atg aac act cag ttt gag gca gtt gga agg gaa ttt<br>Ile Ile Asp Lys Met Asn Thr Gln Phe Glu Ala Val Gly Arg Glu Phe<br>                        405                            410                        415 | 1248 |
| aat aac tta gaa agg aga ata gag aat tta aac aag aag atg gaa gac<br>Asn Asn Leu Glu Arg Arg Ile Glu Asn Leu Asn Lys Lys Met Glu Asp<br>                      420                        425                        430 | 1296 |
| gga ttc cta gat gtc tgg act tat aat gct gaa ctt ctg gtt ctc atg<br>Gly Phe Leu Asp Val Trp Thr Tyr Asn Ala Glu Leu Leu Val Leu Met<br>                435                            440                        445 | 1344 |
| gaa aat gag aga act cta gac ttt cat gac tca aat gtc aag aac ctt<br>Glu Asn Glu Arg Thr Leu Asp Phe His Asp Ser Asn Val Lys Asn Leu<br>450                        455                        460 | 1392 |

```
tac gac aag gtc cga cta caa ctt agg gat aat gca aag gag ctg ggt    1440
Tyr Asp Lys Val Arg Leu Gln Leu Arg Asp Asn Ala Lys Glu Leu Gly
465                 470                 475                 480 aac ggt tgt ttc gag ttc tat cac aaa tgt gat aat gaa tgt atg gaa    1488
Asn Gly Cys Phe Glu Phe Tyr His Lys Cys Asp Asn Glu Cys Met Glu
                485                 490                 495 agt gta aga aac gga acg tat gac tac ccg cag tat tca gaa gaa gca    1536
Ser Val Arg Asn Gly Thr Tyr Asp Tyr Pro Gln Tyr Ser Glu Glu Ala
            500                 505                 510 aga cta aac aga gag gaa ata agt gga gta aaa ttg gaa tca ata gga    1584
Arg Leu Asn Arg Glu Glu Ile Ser Gly Val Lys Leu Glu Ser Ile Gly
        515                 520                 525 act tac caa ata ctg tca att tat tca aca gtg gcg agt tcc cta gca    1632
Thr Tyr Gln Ile Leu Ser Ile Tyr Ser Thr Val Ala Ser Ser Leu Ala
    530                 535                 540 ctg gca atc atg gta gct ggt cta tct tta tgg atg tgc tcc aat gga    1680
Leu Ala Ile Met Val Ala Gly Leu Ser Leu Trp Met Cys Ser Asn Gly
545                 550                 555                 560 tcg tta caa tgc aga att tgc att taa                                1707
Ser Leu Gln Cys Arg Ile Cys Ile
                565
```

<210> SEQ ID NO 40
<211> LENGTH: 568
<212> TYPE: PRT
<213> ORGANISM: Influenza A virus

<400> SEQUENCE: 40

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Thr Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Gly Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Gly Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240
```

```
Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
            405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
            485                 490                 495

Ser Val Arg Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
            565
```

<210> SEQ ID NO 41
<211> LENGTH: 1741
<212> TYPE: DNA
<213> ORGANISM: Influenza A virus
<220> FEATURE:
<221> NAME/KEY: CDS
<222> LOCATION: (9)..(1715)
<223> OTHER INFORMATION:

<400> SEQUENCE: 41

```
ctgtcaaa atg gag aaa ata gtg ctt ctt ttt gca ata gtc agt ctt gtt      50
         Met Glu Lys Ile Val Leu Leu Phe Ala Ile Val Ser Leu Val
         1               5                   10
```

```
aaa agt gat cag att tgc att ggt tac cat gca aac aac tcg aca gag     98
Lys Ser Asp Gln Ile Cys Ile Gly Tyr His Ala Asn Asn Ser Thr Glu
 15              20                  25                  30 cag gtt gac aca ata atg gaa aag aac gtt act gtt aca cat gcc caa    146
Gln Val Asp Thr Ile Met Glu Lys Asn Val Thr Val Thr His Ala Gln
                 35                  40                  45 gac ata ctg gaa aag aca cac aat ggg aag ctc tgc gat cta gat gga    194
Asp Ile Leu Glu Lys Thr His Asn Gly Lys Leu Cys Asp Leu Asp Gly
         50                  55                  60 gtg aag cct cta att ttg aga gat tgt agt gta gct gga tgg ctc ctc    242
Val Lys Pro Leu Ile Leu Arg Asp Cys Ser Val Ala Gly Trp Leu Leu
         65                  70                  75 gga aac cca atg tgt gac gaa ttc atc aat gtg ccg gaa tgg tct tac    290
Gly Asn Pro Met Cys Asp Glu Phe Ile Asn Val Pro Glu Trp Ser Tyr
 80                  85                  90 ata gtg gag aag gcc aat cca gtc aat gac ctc tgt tac cca ggg gat    338
Ile Val Glu Lys Ala Asn Pro Val Asn Asp Leu Cys Tyr Pro Gly Asp
 95                 100                 105                 110 ttc aat gac tat gaa gaa ttg aaa cac cta ttg agc aga ata aac cat    386
Phe Asn Asp Tyr Glu Glu Leu Lys His Leu Leu Ser Arg Ile Asn His
                115                 120                 125 ttt gag aaa att cag atc atc ccc aaa agt tct tgg tcc agt cat gaa    434
Phe Glu Lys Ile Gln Ile Ile Pro Lys Ser Ser Trp Ser Ser His Glu
        130                 135                 140 gcc tca ttg ggg gtg agc tca gca tgt cca tac cag gga aag tcc tcc    482
Ala Ser Leu Gly Val Ser Ser Ala Cys Pro Tyr Gln Gly Lys Ser Ser
        145                 150                 155 ttt ttc aga aat gtg gta tgg ctt atc aaa aag aac agt aca tac cca    530
Phe Phe Arg Asn Val Val Trp Leu Ile Lys Lys Asn Ser Thr Tyr Pro
160                 165                 170 aca ata aag agg agc tac aat aat acc aac caa gaa gat ctt ttg gta    578
Thr Ile Lys Arg Ser Tyr Asn Asn Thr Asn Gln Glu Asp Leu Leu Val
175                 180                 185                 190 ctg tgg ggg att cac cat cct aat gat gcg gca gag cag aca aag ctc    626
Leu Trp Gly Ile His His Pro Asn Asp Ala Ala Glu Gln Thr Lys Leu
                195                 200                 205 tat caa aac cca acc acc tat att tcc gtt ggg aca tct aca cta aac    674
Tyr Gln Asn Pro Thr Thr Tyr Ile Ser Val Gly Thr Ser Thr Leu Asn
        210                 215                 220 cag aga ttg gta cca aga ata gct act aga tcc aaa gta aac ggg caa    722
Gln Arg Leu Val Pro Arg Ile Ala Thr Arg Ser Lys Val Asn Gly Gln
        225                 230                 235 agt gga agg atg gag ttc ttc tgg aca att tta aaa ccg aat gat gca    770
Ser Gly Arg Met Glu Phe Phe Trp Thr Ile Leu Lys Pro Asn Asp Ala
240                 245                 250 atc aac ttc gag agt aat gga aat ttc att gct cca gaa tat gca tac    818
Ile Asn Phe Glu Ser Asn Gly Asn Phe Ile Ala Pro Glu Tyr Ala Tyr
255                 260                 265                 270 aaa att gtc aag aaa ggg gac tca aca att atg aaa agt gaa ttg gaa    866
Lys Ile Val Lys Lys Gly Asp Ser Thr Ile Met Lys Ser Glu Leu Glu
                275                 280                 285 tat ggt aac tgc aac acc aag tgt caa act cca atg ggg gcg ata aac    914
Tyr Gly Asn Cys Asn Thr Lys Cys Gln Thr Pro Met Gly Ala Ile Asn
        290                 295                 300 tct agc atg cca ttc cac aat ata cac cct ctc acc atc ggg gaa tgc    962
Ser Ser Met Pro Phe His Asn Ile His Pro Leu Thr Ile Gly Glu Cys
        305                 310                 315 ccc aaa tat gtg aaa tca aac aga tta gtc ctt gcg act ggg ctc aga   1010
Pro Lys Tyr Val Lys Ser Asn Arg Leu Val Leu Ala Thr Gly Leu Arg
320                 325                 330
```

```
aat agc cct caa aga gag aga aga aaa aag aga gga tta ttt gga      1058
Asn Ser Pro Gln Arg Glu Arg Arg Lys Lys Arg Gly Leu Phe Gly
335                 340                 345                 350 gct ata gca ggt ttt ata gag gga gga tgg cag gga atg gta gat ggt  1106
Ala Ile Ala Gly Phe Ile Glu Gly Gly Trp Gln Gly Met Val Asp Gly
                355                 360                 365 tgg tat ggg tac cac cat agc aac gag cag ggg agt ggg tac gct gca  1154
Trp Tyr Gly Tyr His His Ser Asn Glu Gln Gly Ser Gly Tyr Ala Ala
    370                 375                 380 gac aaa gaa tcc act caa aag gca ata gat gga gtc acc aat aag gtc  1202
Asp Lys Glu Ser Thr Gln Lys Ala Ile Asp Gly Val Thr Asn Lys Val
385                 390                 395 aac tcg att att gac aaa atg aac act cag ttt gag gcc gtt gga agg  1250
Asn Ser Ile Ile Asp Lys Met Asn Thr Gln Phe Glu Ala Val Gly Arg
        400                 405                 410 gaa ttt aac aac tta gaa agg aga ata gag aat tta aac aag aag atg  1298
Glu Phe Asn Asn Leu Glu Arg Arg Ile Glu Asn Leu Asn Lys Lys Met
415                 420                 425                 430 gaa gac ggg ttc cta gat gtc tgg act tat aat gct gaa ctt cta gtt  1346
Glu Asp Gly Phe Leu Asp Val Trp Thr Tyr Asn Ala Glu Leu Leu Val
                435                 440                 445 ctc atg gaa aac gag aga act cta gac ttt cat gac tca aat gtc aag  1394
Leu Met Glu Asn Glu Arg Thr Leu Asp Phe His Asp Ser Asn Val Lys
    450                 455                 460 aac ctt tac gac aag gtc cga cta cag ctt agg gat aat gca aag gag  1442
Asn Leu Tyr Asp Lys Val Arg Leu Gln Leu Arg Asp Asn Ala Lys Glu
465                 470                 475 ctg ggt aac ggt tgt ttc gag ttc tat cat aaa tgt gat aat gaa tgt  1490
Leu Gly Asn Gly Cys Phe Glu Phe Tyr His Lys Cys Asp Asn Glu Cys
        480                 485                 490 atg gaa agt gta aga aac gga acg tat gac tac ccg cag tat tca gaa  1538
Met Glu Ser Val Arg Asn Gly Thr Tyr Asp Tyr Pro Gln Tyr Ser Glu
495                 500                 505                 510 gaa gca aga cta aaa aga gag gaa ata agt gga gta aaa ttg gaa tca  1586
Glu Ala Arg Leu Lys Arg Glu Glu Ile Ser Gly Val Lys Leu Glu Ser
                515                 520                 525 ata gga att tac caa ata ttg tca att tat tct aca gtg gcg agc tcc  1634
Ile Gly Ile Tyr Gln Ile Leu Ser Ile Tyr Ser Thr Val Ala Ser Ser
    530                 535                 540 cta gca ctg gca atc atg gta gct ggt cta tcc tta tgg atg tgc tcc  1682
Leu Ala Leu Ala Ile Met Val Ala Gly Leu Ser Leu Trp Met Cys Ser
545                 550                 555 aat ggg tcg tta caa tgc aga att tgc att taa atttgtgagt tcagattgta  1735
Asn Gly Ser Leu Gln Cys Arg Ile Cys Ile
        560                 565 gttaaa                                                            1741

<210> SEQ ID NO 42
<211> LENGTH: 568
<212> TYPE: PRT
<213> ORGANISM: Influenza A virus

<400> SEQUENCE: 42

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
```

```
                50                  55                  60
Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
                100                 105                 110

Asp Tyr Glu Glu Leu Lys His Leu Leu Ser Arg Ile Asn His Phe Glu
                115                 120                 125

Lys Ile Gln Ile Ile Pro Lys Ser Ser Trp Ser Ser His Glu Ala Ser
130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Lys Leu Tyr Gln
                195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
                275                 280                 285

Asn Cys Asn Thr Lys Cys Gln Thr Pro Met Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Asp Lys
                370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
                450                 455                 460

Tyr Asp Lys Val Arg Leu Gln Leu Arg Asp Asn Ala Lys Glu Leu Gly
465                 470                 475                 480
```

```
                    Asn Gly Cys Phe Glu Phe Tyr His Lys Cys Asp Asn Glu Cys Met Glu
                                    485                 490                 495

Ser Val Arg Asn Gly Thr Tyr Asp Tyr Pro Gln Tyr Ser Glu Glu Ala
                                500                 505                 510

Arg Leu Lys Arg Glu Glu Ile Ser Gly Val Lys Leu Glu Ser Ile Gly
                                515                 520                 525

Ile Tyr Gln Ile Leu Ser Ile Tyr Ser Thr Val Ala Ser Ser Leu Ala
                                530                 535                 540

Leu Ala Ile Met Val Ala Gly Leu Ser Leu Trp Met Cys Ser Asn Gly
                    545                 550                 555                 560

Ser Leu Gln Cys Arg Ile Cys Ile
                                565

<210> SEQ ID NO 43
<211> LENGTH: 1704
<212> TYPE: DNA
<213> ORGANISM: Influenza A virus
<220> FEATURE:
<221> NAME/KEY: CDS
<222> LOCATION: (1)..(1704)
<223> OTHER INFORMATION:

<400> SEQUENCE: 43 atg gag aaa ata gtg ctt ctt ctt gca ata gtc agt ctt gtt aaa agt       48
Met Glu Lys Ile Val Leu Leu Leu Ala Ile Val Ser Leu Val Lys Ser
1               5                   10                  15 gat cag att tgc att ggt tac cat gca aac aac tcg aca gag cag gtt       96
Asp Gln Ile Cys Ile Gly Tyr His Ala Asn Asn Ser Thr Glu Gln Val
            20                  25                  30 gac aca ata atg gaa aag aac gtc act gtt aca cat gcc caa gac ata      144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag      192
Leu Glu Lys Thr His Asn Gly Lys Leu Cys Asp Leu Asp Gly Val Lys
    50                  55                  60 cct cta att tta aga gat tgt agt gta gct gga tgg ctc ctc ggg aac      240
Pro Leu Ile Leu Arg Asp Cys Ser Val Ala Gly Trp Leu Leu Gly Asn
65                  70                  75                  80 cca atg tgt gac gaa ttc atc aat gtg ccg gaa tgg tct tac ata gtg      288
Pro Met Cys Asp Glu Phe Ile Asn Val Pro Glu Trp Ser Tyr Ile Val
                85                  90                  95 gag aag gcc aat cca tcc aat gac ctc tgt tac cca ggg aat ttc aac      336
Glu Lys Ala Asn Pro Ser Asn Asp Leu Cys Tyr Pro Gly Asn Phe Asn
            100                 105                 110 gac tat gaa gaa ctg aaa cac cta ttg agc aga ata aac cat ttt gaa      384
Asp Tyr Glu Glu Leu Lys His Leu Leu Ser Arg Ile Asn His Phe Glu
        115                 120                 125 aaa att cag atc atc ccc aaa agt tct tgg tcc gat cat gaa gcc tca      432
Lys Ile Gln Ile Ile Pro Lys Ser Ser Trp Ser Asp His Glu Ala Ser
    130                 135                 140 tca ggg gtg agc tca gca tgt cca tac cag gga agg tcc tcc ttt ttc      480
Ser Gly Val Ser Ser Ala Cys Pro Tyr Gln Gly Arg Ser Ser Phe Phe
145                 150                 155                 160 aga aat gtg gta tgg ctt atc aaa aag aac agt gca tac cca aca ata      528
Arg Asn Val Val Trp Leu Ile Lys Lys Asn Ser Ala Tyr Pro Thr Ile
                165                 170                 175 aag aga agc tac aat aat acc aac caa gaa gat ctt ttg gta ctg tgg      576
Lys Arg Ser Tyr Asn Asn Thr Asn Gln Glu Asp Leu Leu Val Leu Trp
            180                 185                 190 ggg att cac cat cca aat gat gcg gca gag cag aca aga ctc tat caa      624
Gly Ile His His Pro Asn Asp Ala Ala Glu Gln Thr Arg Leu Tyr Gln
```

-continued

```
                    195                     200                     205
aac cca acc aca tat att tcc gtt ggg aca tca aca cta aac cag aga     672
Asn Pro Thr Thr Tyr Ile Ser Val Gly Thr Ser Thr Leu Asn Gln Arg
        210                     215                     220 ttg gta cca aaa ata gct act aga tcc aaa ata aac ggg caa agt gga     720
Leu Val Pro Lys Ile Ala Thr Arg Ser Lys Ile Asn Gly Gln Ser Gly
225                     230                     235                     240 agg atg gag ttc ttc tgg aca att tta aaa ccg aat gat gca atc agc     768
Arg Met Glu Phe Phe Trp Thr Ile Leu Lys Pro Asn Asp Ala Ile Ser
                245                     250                     255 ttt gag agt aat gga aat ttc att gct cca gaa tat gca tac aaa att     816
Phe Glu Ser Asn Gly Asn Phe Ile Ala Pro Glu Tyr Ala Tyr Lys Ile
            260                     265                     270 gtc aag aaa ggg gac tca gca att atg aaa agt gaa ttg gaa tat ggt     864
Val Lys Lys Gly Asp Ser Ala Ile Met Lys Ser Glu Leu Glu Tyr Gly
        275                     280                     285 aac tgc aac acc aag tgt caa act cca atg ggg gcg ata aac tct agt     912
Asn Cys Asn Thr Lys Cys Gln Thr Pro Met Gly Ala Ile Asn Ser Ser
290                     295                     300 atg cca ttc cac aac ata cac cct ctc acc atc gga gaa tgc ccc aaa     960
Met Pro Phe His Asn Ile His Pro Leu Thr Ile Gly Glu Cys Pro Lys
305                     310                     315                     320 tat gtg aaa tca agc aga tta gtc ctt gcg act ggg ctc aga aat agc    1008
Tyr Val Lys Ser Ser Arg Leu Val Leu Ala Thr Gly Leu Arg Asn Ser
                325                     330                     335 cct caa aga gag aga aga aag aga gga cta ttt gga gct ata gca        1056
Pro Gln Arg Glu Arg Arg Lys Lys Arg Gly Leu Phe Gly Ala Ile Ala
            340                     345                     350 ggt ttt ata gag gga gga tgg cag ggg atg gta gat ggt tgg tat ggg    1104
Gly Phe Ile Glu Gly Gly Trp Gln Gly Met Val Asp Gly Trp Tyr Gly
        355                     360                     365 tac cac cat agc aat gag cag ggg agt ggg tac gct gca gac aaa gaa    1152
Tyr His His Ser Asn Glu Gln Gly Ser Gly Tyr Ala Ala Asp Lys Glu
370                     375                     380 tcc act caa aag gca ata gat gga gtc acc aat aag gtc aac tcg atc    1200
Ser Thr Gln Lys Ala Ile Asp Gly Val Thr Asn Lys Val Asn Ser Ile
385                     390                     395                     400 att gac aaa atg aac act cag ttt gag gcc gtt gga agg gaa ttt aat    1248
Ile Asp Lys Met Asn Thr Gln Phe Glu Ala Val Gly Arg Glu Phe Asn
                405                     410                     415 aac tta gaa agg aga ata gaa aat tta aac aag aag atg gaa gac gga    1296
Asn Leu Glu Arg Arg Ile Glu Asn Leu Asn Lys Lys Met Glu Asp Gly
            420                     425                     430 ttc cta gat gtc tgg act tat aat gct gaa ctt ctg gtt ctc atg gaa    1344
Phe Leu Asp Val Trp Thr Tyr Asn Ala Glu Leu Leu Val Leu Met Glu
        435                     440                     445 aat gag aga act cta gac ttt cat gac tca aat gtc aag aac ctt tac    1392
Asn Glu Arg Thr Leu Asp Phe His Asp Ser Asn Val Lys Asn Leu Tyr
450                     455                     460 gac aag gtc cga cta cag ctt agg gat aat gca aag gag ctg ggt aac    1440
Asp Lys Val Arg Leu Gln Leu Arg Asp Asn Ala Lys Glu Leu Gly Asn
465                     470                     475                     480 ggt tgt ttc gag ttc tat cac aga tgt gat aat gaa tgt ata gaa agt    1488
Gly Cys Phe Glu Phe Tyr His Arg Cys Asp Asn Glu Cys Ile Glu Ser
                485                     490                     495 gta aga aac gga acg tat gac tac ccg cag tat tca gaa gaa gca aga    1536
Val Arg Asn Gly Thr Tyr Asp Tyr Pro Gln Tyr Ser Glu Glu Ala Arg
            500                     505                     510 tta aaa aga gag gaa ata agt gga gta aaa ttg gaa tca ata gga act    1584
Leu Lys Arg Glu Glu Ile Ser Gly Val Lys Leu Glu Ser Ile Gly Thr
```

```
                    515                 520                 525
tac caa ata ctg tca att tat tca aca gtg gca agt tcc cta gca ctg        1632
Tyr Gln Ile Leu Ser Ile Tyr Ser Thr Val Ala Ser Ser Leu Ala Leu
        530                 535                 540 gca atc atg gtg gct ggt cta tct tta tgg atg tgc tcc aat gga tcg        1680
Ala Ile Met Val Ala Gly Leu Ser Leu Trp Met Cys Ser Asn Gly Ser
545                 550                 555                 560 tta caa tgc aga att tgc att taa                                        1704
Leu Gln Cys Arg Ile Cys Ile
                565

<210> SEQ ID NO 44
<211> LENGTH: 567
<212> TYPE: PRT
<213> ORGANISM: Influenza A virus

<400> SEQUENCE: 44

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ser Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Ile Asn Gly Gln Ser Gly
225                 230                 235                 240

Arg Met Glu Phe Phe Trp Thr Ile Leu Lys Pro Asn Asp Ala Ile Ser
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
```

```
                305                 310                 315                 320
Tyr Val Lys Ser Ser Arg Leu Val Leu Ala Thr Gly Leu Arg Asn Ser
                325                 330                 335

Pro Gln Arg Glu Arg Lys Lys Arg Gly Leu Phe Gly Ala Ile Ala
                340                 345                 350

Gly Phe Ile Glu Gly Gly Trp Gln Gly Met Val Asp Gly Trp Tyr Gly
                355                 360                 365

Tyr His His Ser Asn Glu Gln Gly Ser Gly Tyr Ala Ala Asp Lys Glu
                370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
                435                 440                 445

Asn Glu Arg Thr Leu Asp Phe His Asp Ser Asn Val Lys Asn Leu Tyr
                450                 455                 460

Asp Lys Val Arg Leu Gln Leu Arg Asp Asn Ala Lys Glu Leu Gly Asn
465                 470                 475                 480

Gly Cys Phe Glu Phe Tyr His Arg Cys Asp Asn Glu Cys Ile Glu Ser
                485                 490                 495

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
                515                 520                 525

Tyr Gln Ile Leu Ser Ile Tyr Ser Thr Val Ala Ser Ser Leu Ala Leu
                530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 45
<211> LENGTH: 1737
<212> TYPE: DNA
<213> ORGANISM: Influenza A virus
<220> FEATURE:
<221> NAME/KEY: CDS
<222> LOCATION: (15)..(1721)
<223> OTHER INFORMATION:

<400> SEQUENCE: 45
ttcaatctgt caaa atg gag aaa ata gtg ctt ctt ctt gca ata gtc agt         50
              Met Glu Lys Ile Val Leu Leu Leu Ala Ile Val Ser
              1               5                   10 ctt gtt aaa agt gat cag att tgc att ggt tac cat gca aac aac tca        98
Leu Val Lys Ser Asp Gln Ile Cys Ile Gly Tyr His Ala Asn Asn Ser
        15                  20                  25 aca gag cag gtt gac aca ata atg gaa aag aac gtc act gtt aca cac       146
Thr Glu Gln Val Asp Thr Ile Met Glu Lys Asn Val Thr Val Thr His
    30                  35                  40 gcc caa gac ata ctg gag aag aca cac aac ggg aaa ctc tgc gat cta       194
Ala Gln Asp Ile Leu Glu Lys Thr His Asn Gly Lys Leu Cys Asp Leu
45                  50                  55                  60 gat gga gtg aag cct cta att tta aga gat tgt agt gta gct gga tgg       242
Asp Gly Val Lys Pro Leu Ile Leu Arg Asp Cys Ser Val Ala Gly Trp
```

-continued

| | | | | | | | | | | | | |
|---|---|---|---|---|---|---|---|---|---|---|---|---|
| | | 65 | | | | 70 | | | | 75 | | |
| ctc | ctc | ggg | aac | cca | atg | tgt | gac | gaa | ttc | ctc | aat | gtg ccg gaa tgg | 290 |
| Leu | Leu | Gly | Asn | Pro | Met | Cys | Asp | Glu | Phe | Leu | Asn | Val Pro Glu Trp |
| | | 80 | | | | | 85 | | | | | 90 |
| tct | tac | ata | gtg | gag | aag | atc | aat | cca | gcc | aat | gac | ctc tgt tac cca | 338 |
| Ser | Tyr | Ile | Val | Glu | Lys | Ile | Asn | Pro | Ala | Asn | Asp | Leu Cys Tyr Pro |
| | | | 95 | | | | | 100 | | | | | 105 |
| ggg | aat | ttc | aac | gac | tat | gaa | gaa | ctg | aaa | cac | cta | ttg agc aga ata | 386 |
| Gly | Asn | Phe | Asn | Asp | Tyr | Glu | Glu | Leu | Lys | His | Leu | Leu Ser Arg Ile |
| | 110 | | | | | 115 | | | | | 120 |
| aac | cat | ttt | gag | aaa | ata | cag | atc | atc | ccc | aaa | agt | tct tgg tca gat | 434 |
| Asn | His | Phe | Glu | Lys | Ile | Gln | Ile | Ile | Pro | Lys | Ser | Ser Trp Ser Asp |
| 125 | | | | | 130 | | | | | 135 | | | | | 140 |
| cat | gaa | gcc | tca | tca | ggg | gtg | agc | tca | gca | tgt | cca | tac cag gga agg | 482 |
| His | Glu | Ala | Ser | Ser | Gly | Val | Ser | Ser | Ala | Cys | Pro | Tyr Gln Gly Arg |
| | | | | 145 | | | | | 150 | | | | | 155 |
| tcc | tcc | ttt | ttt | aga | aat | gtg | gta | tgg | ctt | atc | aaa | aag gac aat gca | 530 |
| Ser | Ser | Phe | Phe | Arg | Asn | Val | Val | Trp | Leu | Ile | Lys | Lys Asp Asn Ala |
| | | | 160 | | | | | 165 | | | | | 170 |
| tac | cca | aca | ata | aag | aga | agt | tac | aat | aat | acc | aac | caa gaa gat ctt | 578 |
| Tyr | Pro | Thr | Ile | Lys | Arg | Ser | Tyr | Asn | Asn | Thr | Asn | Gln Glu Asp Leu |
| | | 175 | | | | | 180 | | | | | 185 |
| ttg | gta | ctg | tgg | ggg | att | cac | cat | cca | aat | gat | gcg | gca gag cag aca | 626 |
| Leu | Val | Leu | Trp | Gly | Ile | His | His | Pro | Asn | Asp | Ala | Ala Glu Gln Thr |
| | 190 | | | | | 195 | | | | | 200 |
| agg | ctc | tat | caa | aac | cca | acc | acc | tat | att | tcc | gtt | ggt aca tca aca | 674 |
| Arg | Leu | Tyr | Gln | Asn | Pro | Thr | Thr | Tyr | Ile | Ser | Val | Gly Thr Ser Thr |
| 205 | | | | | 210 | | | | | 215 | | | | | 220 |
| cta | aac | cag | aga | ctg | gta | cca | aaa | ata | gct | act | aga | tcc aag gta aac | 722 |
| Leu | Asn | Gln | Arg | Leu | Val | Pro | Lys | Ile | Ala | Thr | Arg | Ser Lys Val Asn |
| | | | | 225 | | | | | 230 | | | | | 235 |
| ggg | caa | agt | gga | agg | atg | gag | ttc | ttt | tgg | aca | att | tta aaa ccg aat | 770 |
| Gly | Gln | Ser | Gly | Arg | Met | Glu | Phe | Phe | Trp | Thr | Ile | Leu Lys Pro Asn |
| | | | 240 | | | | | 245 | | | | | 250 |
| gat | gca | ata | aac | ttt | gag | agt | aat | gga | aat | ttc | att | gct cca gaa aat | 818 |
| Asp | Ala | Ile | Asn | Phe | Glu | Ser | Asn | Gly | Asn | Phe | Ile | Ala Pro Glu Asn |
| | 255 | | | | | 260 | | | | | 265 |
| gca | tac | aaa | att | gtc | aag | aaa | ggg | gac | tca | aca | att | atg aaa agt gaa | 866 |
| Ala | Tyr | Lys | Ile | Val | Lys | Lys | Gly | Asp | Ser | Thr | Ile | Met Lys Ser Glu |
| 270 | | | | | 275 | | | | | 280 |
| ttg | gaa | tat | ggt | aac | tgc | aac | acc | aag | tgt | caa | act | cca ata ggg gcg | 914 |
| Leu | Glu | Tyr | Gly | Asn | Cys | Asn | Thr | Lys | Cys | Gln | Thr | Pro Ile Gly Ala |
| 285 | | | | | 290 | | | | | 295 | | | | | 300 |
| ata | aac | tct | agt | atg | cca | ttc | cac | aac | atc | cac | cct | ctc acc atc ggg | 962 |
| Ile | Asn | Ser | Ser | Met | Pro | Phe | His | Asn | Ile | His | Pro | Leu Thr Ile Gly |
| | | | 305 | | | | | 310 | | | | | 315 |
| gaa | tgc | ccc | aaa | tat | gtg | aaa | tca | aac | aga | tta | gtc | ctt gcg act ggg | 1010 |
| Glu | Cys | Pro | Lys | Tyr | Val | Lys | Ser | Asn | Arg | Leu | Val | Leu Ala Thr Gly |
| | | 320 | | | | | 325 | | | | | 330 |
| ctc | aga | aat | agc | cct | caa | gga | gag | aga | aga | aga | aag | aga gga cta | 1058 |
| Leu | Arg | Asn | Ser | Pro | Gln | Gly | Glu | Arg | Arg | Arg | Lys | Arg Gly Leu |
| | 335 | | | | | 340 | | | | | 345 |
| ttt | gga | gct | ata | gca | ggt | ttt | ata | gag | gga | gga | tgg | cag gga atg gta | 1106 |
| Phe | Gly | Ala | Ile | Ala | Gly | Phe | Ile | Glu | Gly | Gly | Trp | Gln Gly Met Val |
| 350 | | | | | 355 | | | | | 360 |
| gat | ggt | tgg | tat | ggg | tac | cac | cat | agc | aac | gag | cag | ggg agt ggg tac | 1154 |
| Asp | Gly | Trp | Tyr | Gly | Tyr | His | His | Ser | Asn | Glu | Gln | Gly Ser Gly Tyr |
| 365 | | | | | 370 | | | | | 375 | | | | | 380 |
| gct | gca | gac | aaa | gaa | tcc | act | caa | aag | gca | ata | gat | gga gtc acc aat | 1202 |
| Ala | Ala | Asp | Lys | Glu | Ser | Thr | Gln | Lys | Ala | Ile | Asp | Gly Val Thr Asn |

```
                         385                 390                  395
aag gtc aac tcg atc att gac aaa atg aac act cag ttt gag gct gtt        1250
Lys Val Asn Ser Ile Ile Asp Lys Met Asn Thr Gln Phe Glu Ala Val
            400                 405                 410 gga agg gaa ttt aat aac tta gaa agg aga ata gaa aat tta aac aag        1298
Gly Arg Glu Phe Asn Asn Leu Glu Arg Arg Ile Glu Asn Leu Asn Lys
        415                 420                 425 aag atg gaa gac gga ttc cta gat gtc tgg act tat aat gct gaa ctt        1346
Lys Met Glu Asp Gly Phe Leu Asp Val Trp Thr Tyr Asn Ala Glu Leu
    430                 435                 440 ctg gtt ctc atg gaa aat gag aga act cta gac ttt cat gac tca aat        1394
Leu Val Leu Met Glu Asn Glu Arg Thr Leu Asp Phe His Asp Ser Asn
445                 450                 455                 460 gtc aag aac ctt tac gac aag gtc cga cta cag ctt agg gat aat gca        1442
Val Lys Asn Leu Tyr Asp Lys Val Arg Leu Gln Leu Arg Asp Asn Ala
                465                 470                 475 aag gag ctt ggt aac ggt tgt ttc gag ttc tat cat aga tgt gat aat        1490
Lys Glu Leu Gly Asn Gly Cys Phe Glu Phe Tyr His Arg Cys Asp Asn
            480                 485                 490 gaa tgt atg gaa agt gta aga aac gga acg tat gac tac ccg cag tat        1538
Glu Cys Met Glu Ser Val Arg Asn Gly Thr Tyr Asp Tyr Pro Gln Tyr
        495                 500                 505 tca gaa gaa gca aga tta aaa aga gag gaa ata agt gga gta aaa ttg        1586
Ser Glu Glu Ala Arg Leu Lys Arg Glu Glu Ile Ser Gly Val Lys Leu
    510                 515                 520 gaa tca ata gga act tac caa ata ctg tca att tat tca aca gtg gcg        1634
Glu Ser Ile Gly Thr Tyr Gln Ile Leu Ser Ile Tyr Ser Thr Val Ala
525                 530                 535                 540 agc tcc cta gca ctg gca atc atg gtg gct ggt cta tct tta tgg atg        1682
Ser Ser Leu Ala Leu Ala Ile Met Val Ala Gly Leu Ser Leu Trp Met
                545                 550                 555 tgc tcc aat gga tcg tta caa tgc aga att tgc att taa atttgtgagt        1731
Cys Ser Asn Gly Ser Leu Gln Cys Arg Ile Cys Ile
            560                 565 tcagat                                                                 1737

<210> SEQ ID NO 46
<211> LENGTH: 568
<212> TYPE: PRT
<213> ORGANISM: Influenza A virus

<400> SEQUENCE: 46

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125
```

```
Lys Ile Gln Ile Ile Pro Lys Ser Ser Trp Ser Asp His Glu Ala Ser
            130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Arg Leu Tyr Gln
                195                 200                 205

Asn Pro Thr Thr Tyr Ile Ser Val Gly Thr Ser Thr Leu Asn Gln Arg
            210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
                260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Ile Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Arg Lys Arg Gly Leu Phe Gly Ala Ile
                340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560
```

```
<210> SEQ ID NO 47
<211> LENGTH: 1745
<212> TYPE: DNA
<213> ORGANISM: Influenza A virus
<220> FEATURE:
<221> NAME/KEY: CDS
<222> LOCATION: (15)..(1721)
<223> OTHER INFORMATION:

<400> SEQUENCE: 47
```

| | | | | | | | | | | | | | | |
|---|---|---|---|---|---|---|---|---|---|---|---|---|---|---|
| ttcaatctgt caaa | atg<br>Met<br>1 | gag<br>Glu | aaa<br>Lys | ata<br>Ile | gtg<br>Val<br>5 | ctt<br>Leu | ctt<br>Leu | ctt<br>Leu | gca<br>Ala | ata<br>Ile | atc<br>Ile<br>10 | agt<br>Ser | | 50 |
| ctt<br>Leu | gtt<br>Val | aaa<br>Lys<br>15 | agt<br>Ser | gat<br>Asp | cag<br>Gln | att<br>Ile | tgc<br>Cys<br>20 | att<br>Ile | ggt<br>Gly | tac<br>Tyr | cat<br>His | gca<br>Ala<br>25 | aac<br>Asn | aac<br>Asn | tcg<br>Ser | 98 |
| aca<br>Thr | gag<br>Glu<br>30 | cag<br>Gln | gtt<br>Val | gac<br>Asp | aca<br>Thr | ata<br>Ile<br>35 | atg<br>Met | gaa<br>Glu | aag<br>Lys | aac<br>Asn | gtc<br>Val<br>40 | act<br>Thr | gtt<br>Val | aca<br>Thr | cac<br>His | 146 |
| gcc<br>Ala<br>45 | caa<br>Gln | gac<br>Asp | ata<br>Ile | ctg<br>Leu | gaa<br>Glu<br>50 | aag<br>Lys | aca<br>Thr | cac<br>His | aac<br>Asn | ggg<br>Gly<br>55 | aag<br>Lys | ctc<br>Leu | tgc<br>Cys | gat<br>Asp | cta<br>Leu<br>60 | 194 |
| gac<br>Asp | gga<br>Gly | gtg<br>Val | aag<br>Lys | cct<br>Pro<br>65 | cta<br>Leu | att<br>Ile | tta<br>Leu | aga<br>Arg | gat<br>Asp<br>70 | tgt<br>Cys | agt<br>Ser | gta<br>Val | gct<br>Ala | gga<br>Gly<br>75 | tgg<br>Trp | 242 |
| ctc<br>Leu | ctc<br>Leu | ggg<br>Gly | aat<br>Asn<br>80 | cca<br>Pro | atg<br>Met | tgt<br>Cys | gac<br>Asp | gaa<br>Glu<br>85 | ttc<br>Phe | ctc<br>Leu | aat<br>Asn | gtg<br>Val | ccg<br>Pro<br>90 | gaa<br>Glu | tgg<br>Trp | 290 |
| tct<br>Ser | tac<br>Tyr | ata<br>Ile<br>95 | gtg<br>Val | gag<br>Glu | aag<br>Lys | atc<br>Ile | aat<br>Asn<br>100 | cca<br>Pro | gcc<br>Ala | aat<br>Asn | gac<br>Asp | ctc<br>Leu<br>105 | tgt<br>Cys | tac<br>Tyr | cca<br>Pro | 338 |
| ggg<br>Gly | aat<br>Asn<br>110 | ttc<br>Phe | aac<br>Asn | gac<br>Asp | tat<br>Tyr | gaa<br>Glu<br>115 | gaa<br>Glu | ctg<br>Leu | aaa<br>Lys | cac<br>His | cta<br>Leu<br>120 | ttg<br>Leu | agc<br>Ser | aga<br>Arg | ata<br>Ile | 386 |
| aac<br>Asn<br>125 | cat<br>His | ttt<br>Phe | gag<br>Glu | aaa<br>Lys | att<br>Ile<br>130 | cag<br>Gln | atc<br>Ile | atc<br>Ile | ccc<br>Pro | aaa<br>Lys<br>135 | agt<br>Ser | tct<br>Ser | tgg<br>Trp | tca<br>Ser | gat<br>Asp<br>140 | 434 |
| cat<br>His | gaa<br>Glu | gcc<br>Ala | tca<br>Ser | tca<br>Ser<br>145 | ggg<br>Gly | gtg<br>Val | agc<br>Ser | tca<br>Ser | gca<br>Ala<br>150 | tgt<br>Cys | cca<br>Pro | tac<br>Tyr | cag<br>Gln | gga<br>Gly<br>155 | agg<br>Arg | 482 |
| tcc<br>Ser | tcc<br>Ser | ttt<br>Phe | ttt<br>Phe<br>160 | aga<br>Arg | aat<br>Asn | gtg<br>Val | gta<br>Val | tgg<br>Trp<br>165 | ctt<br>Leu | atc<br>Ile | aaa<br>Lys | aag<br>Lys | aac<br>Asn<br>170 | gat<br>Asp | gca<br>Ala | 530 |
| tac<br>Tyr | cca<br>Pro | aca<br>Thr<br>175 | ata<br>Ile | aag<br>Lys | aga<br>Arg | agt<br>Ser | tac<br>Tyr<br>180 | aat<br>Asn | aat<br>Asn | acc<br>Thr | aac<br>Asn | caa<br>Gln<br>185 | gaa<br>Glu | gat<br>Asp | ctt<br>Leu | 578 |
| ttg<br>Leu | gta<br>Val<br>190 | ctg<br>Leu | tgg<br>Trp | ggg<br>Gly | att<br>Ile | cac<br>His<br>195 | cat<br>His | cca<br>Pro | aat<br>Asn | gat<br>Asp | gcg<br>Ala<br>200 | gca<br>Ala | gag<br>Glu | cag<br>Gln | aca<br>Thr | 626 |
| agg<br>Arg<br>205 | ctc<br>Leu | tat<br>Tyr | caa<br>Gln | aac<br>Asn | cca<br>Pro<br>210 | acc<br>Thr | acc<br>Thr | tat<br>Tyr | att<br>Ile | tcc<br>Ser<br>215 | gtt<br>Val | ggg<br>Gly | aca<br>Thr | tca<br>Ser | aca<br>Thr<br>220 | 674 |
| cta<br>Leu | aac<br>Asn | cag<br>Gln | aga<br>Arg | ttg<br>Leu<br>225 | gta<br>Val | cca<br>Pro | aaa<br>Lys | ata<br>Ile | gct<br>Ala<br>230 | act<br>Thr | aga<br>Arg | tcc<br>Ser | aag<br>Lys | gta<br>Val<br>235 | aac<br>Asn | 722 |
| ggg<br>Gly | caa<br>Gln | agt<br>Ser<br>240 | gga<br>Gly | agg<br>Arg | atg<br>Met | gag<br>Glu | ttc<br>Phe<br>245 | ttt<br>Phe | tgg<br>Trp | aca<br>Thr | att<br>Ile | tta<br>Leu<br>250 | aaa<br>Lys | ccg<br>Pro | aat<br>Asn | 770 |

```
                                                          -continued
gat gca ata aat ttt gag agt aat gga aat ttc att gct cca gaa aat      818
Asp Ala Ile Asn Phe Glu Ser Asn Gly Asn Phe Ile Ala Pro Glu Asn
            255                 260                 265 gca tac aaa att gtc aag aaa ggg gac tca aca atc atg aaa agt gaa      866
Ala Tyr Lys Ile Val Lys Lys Gly Asp Ser Thr Ile Met Lys Ser Glu
            270                 275                 280 ttg gaa tat ggt aac tgc aac acc aag tgt caa act cca ata ggg gcg      914
Leu Glu Tyr Gly Asn Cys Asn Thr Lys Cys Gln Thr Pro Ile Gly Ala
285                 290                 295                 300 ata aac tct agt atg cca ttc cac aac atc cac cct ctc acc atc ggg      962
Ile Asn Ser Ser Met Pro Phe His Asn Ile His Pro Leu Thr Ile Gly
                305                 310                 315 gaa tgc ccc aaa tat gtg aaa tca aac aga tta gtc ctt gcg act ggg     1010
Glu Cys Pro Lys Tyr Val Lys Ser Asn Arg Leu Val Leu Ala Thr Gly
            320                 325                 330 ctc aga aat agc cct caa gga gag aga aga aaa aag aga gga cta         1058
Leu Arg Asn Ser Pro Gln Gly Glu Arg Arg Arg Lys Lys Arg Gly Leu
            335                 340                 345 ttt gga gct ata gca ggt ttt ata gag gga gga tgg cag gga atg gta     1106
Phe Gly Ala Ile Ala Gly Phe Ile Glu Gly Gly Trp Gln Gly Met Val
350                 355                 360 gat ggt tgg tat ggg tac cac cat agc aac gag cag ggg agt ggg tac     1154
Asp Gly Trp Tyr Gly Tyr His His Ser Asn Glu Gln Gly Ser Gly Tyr
365                 370                 375                 380 gct gca gac aaa gaa tcc act caa aag gca ata gat gga gtc acc aat     1202
Ala Ala Asp Lys Glu Ser Thr Gln Lys Ala Ile Asp Gly Val Thr Asn
            385                 390                 395 aag gtc aac tcg atc att gac aaa atg aac act cag ttt gag gcc gtt     1250
Lys Val Asn Ser Ile Ile Asp Lys Met Asn Thr Gln Phe Glu Ala Val
            400                 405                 410 gga agg gaa ttt aat aac tta gaa agg aga ata gag aat tta aac aag     1298
Gly Arg Glu Phe Asn Asn Leu Glu Arg Arg Ile Glu Asn Leu Asn Lys
            415                 420                 425 aag atg gaa gac gga ttt cta gat gtc tgg act tat aat gct gaa ctt     1346
Lys Met Glu Asp Gly Phe Leu Asp Val Trp Thr Tyr Asn Ala Glu Leu
            430                 435                 440 ctg gtt ctc atg gaa aat gag aga act cta gac ttt cat gac tca aat     1394
Leu Val Leu Met Glu Asn Glu Arg Thr Leu Asp Phe His Asp Ser Asn
445                 450                 455                 460 gtc aag aac ctt tac gac aag gtc cga cta cag ctt agg gat aat gca     1442
Val Lys Asn Leu Tyr Asp Lys Val Arg Leu Gln Leu Arg Asp Asn Ala
                465                 470                 475 aag gag ctt ggt aac ggt tgt ttc gag ttc tat cac aga tgt gat aat     1490
Lys Glu Leu Gly Asn Gly Cys Phe Glu Phe Tyr His Arg Cys Asp Asn
            480                 485                 490 gaa tgt atg gaa agt gta aga aac gga acg tat gac tac ccg cag tat    1538
Glu Cys Met Glu Ser Val Arg Asn Gly Thr Tyr Asp Tyr Pro Gln Tyr
            495                 500                 505 tca gaa gaa tca aga tta aaa aga gag gaa ata agt gga gta aaa ttg    1586
Ser Glu Glu Ser Arg Leu Lys Arg Glu Glu Ile Ser Gly Val Lys Leu
            510                 515                 520 gaa tca ata gga act tat caa ata ctg tca att tat tca aca gtg gcg    1634
Glu Ser Ile Gly Thr Tyr Gln Ile Leu Ser Ile Tyr Ser Thr Val Ala
525                 530                 535                 540 agc tcc cta gca ctg gca atc atg gtg gct ggt cta tct tta tgg atg    1682
Ser Ser Leu Ala Leu Ala Ile Met Val Ala Gly Leu Ser Leu Trp Met
                545                 550                 555 tgc tcc aat gga tcg tta caa tgc aga att tgc att taa atttgtgagt    1731
Cys Ser Asn Gly Ser Leu Gln Cys Arg Ile Cys Ile
            560                 565
```
tcagattgta gtta                                              1745

<210> SEQ ID NO 48
<211> LENGTH: 568
<212> TYPE: PRT
<213> ORGANISM: Influenza A virus

<400> SEQUENCE: 48

Met Glu Lys Ile Val Leu Leu Ala Ile Ile Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Asp Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys

|       |       |       |       | 370   |       |       |       | 375   |       |       |       | 380   |       |       |
|-------|-------|-------|-------|-------|-------|-------|-------|-------|-------|-------|-------|-------|-------|-------|

Glu Ser Thr Gln Lys Ala Ile Asp Gly Val Thr Asn Lys Val Asn Ser
385                     390                     395                     400

Ile Ile Asp Lys Met Asn Thr Gln Phe Glu Ala Val Gly Arg Glu Phe
                405                     410                     415

Asn Asn Leu Glu Arg Arg Ile Glu Asn Leu Asn Lys Lys Met Glu Asp
                    420                     425                     430

Gly Phe Leu Asp Val Trp Thr Tyr Asn Ala Glu Leu Leu Val Leu Met
                435                     440                     445

Glu Asn Glu Arg Thr Leu Asp Phe His Asp Ser Asn Val Lys Asn Leu
450                     455                     460

Tyr Asp Lys Val Arg Leu Gln Leu Arg Asp Asn Ala Lys Glu Leu Gly
465                     470                     475                     480

Asn Gly Cys Phe Glu Phe Tyr His Arg Cys Asp Asn Glu Cys Met Glu
                    485                     490                     495

Ser Val Arg Asn Gly Thr Tyr Asp Tyr Pro Gln Tyr Ser Glu Glu Ser
                500                     505                     510

Arg Leu Lys Arg Glu Glu Ile Ser Gly Val Lys Leu Glu Ser Ile Gly
                515                     520                     525

Thr Tyr Gln Ile Leu Ser Ile Tyr Ser Thr Val Ala Ser Ser Leu Ala
                530                     535                     540

Leu Ala Ile Met Val Ala Gly Leu Ser Leu Trp Met Cys Ser Asn Gly
545                     550                     555                     560

Ser Leu Gln Cys Arg Ile Cys Ile
                565

<210> SEQ ID NO 49
<211> LENGTH: 1732
<212> TYPE: DNA
<213> ORGANISM: Influenza A virus
<220> FEATURE:
<221> NAME/KEY: CDS
<222> LOCATION: (15)..(1709)
<223> OTHER INFORMATION:

<400> SEQUENCE: 1
tctaatctgt taaa atg gag aaa ata gta ctt ctt ttt gca ata gtc agt      50
              Met Glu Lys Ile Val Leu Leu Phe Ala Ile Val Ser
              1               5                   10 ctt gtc aaa agt gac caa att tgc att ggt tac cat gca aac aac tca     98
Leu Val Lys Ser Asp Gln Ile Cys Ile Gly Tyr His Ala Asn Asn Ser
        15                  20                  25 aca gag cag gtt gac aca ata atg gaa aag aat gtt act gtc acg cat    146
Thr Glu Gln Val Asp Thr Ile Met Glu Lys Asn Val Thr Val Thr His
    30                  35                  40 gcc caa gac ata ctg gaa aag aca cac aat ggg aag ctc tgc agt cta    194
Ala Gln Asp Ile Leu Glu Lys Thr His Asn Gly Lys Leu Cys Ser Leu
45                  50                  55                  60 aat gga gtt aag cct ctc att ttg agg gat tgt agt gta gct gga tgg    242
Asn Gly Val Lys Pro Leu Ile Leu Arg Asp Cys Ser Val Ala Gly Trp
                65                  70                  75 ctc ctc gga aac ccc atg tgt gat gaa ttc ctc aat gtg ccg gaa tgg    290
Leu Leu Gly Asn Pro Met Cys Asp Glu Phe Leu Asn Val Pro Glu Trp
            80                  85                  90 tct tac ata gtg gag aag gac agc cca atc aat ggc ctc tgc tac cca    338
Ser Tyr Ile Val Glu Lys Asp Ser Pro Ile Asn Gly Leu Cys Tyr Pro
        95                  100                 105 ggg gat ttc aac gac tat gaa gag ctg aaa cac ctg ttg agc agt aca    386
Gly Asp Phe Asn Asp Tyr Glu Glu Leu Lys His Leu Leu Ser Ser Thr
    110                 115                 120

```
                110                 115                 120
aac cat ttt gag aaa att caa atc atc ccc agg agt tct tgg tcc gat    434
Asn His Phe Glu Lys Ile Gln Ile Ile Pro Arg Ser Ser Trp Ser Asp
125                 130                 135                 140 cat gat gcc tca tca gga gtg agc tcc gca tgt cca tat aat ggg agg    482
His Asp Ala Ser Ser Gly Val Ser Ser Ala Cys Pro Tyr Asn Gly Arg
                145                 150                 155 tcc tcc ttt ttc aga aat gta gtg tgg ctc atc aaa aag aac aat gca    530
Ser Ser Phe Phe Arg Asn Val Val Trp Leu Ile Lys Lys Asn Asn Ala
            160                 165                 170 tac cca aca ata aaa agg aat tac aat aat act aac caa gaa gat ctt    578
Tyr Pro Thr Ile Lys Arg Asn Tyr Asn Asn Thr Asn Gln Glu Asp Leu
        175                 180                 185 ttg gta ctg tgg ggg att cac cat cct aat gat gca aca gag cag aca    626
Leu Val Leu Trp Gly Ile His His Pro Asn Asp Ala Thr Glu Gln Thr
    190                 195                 200 aag ctc tat caa aac cca acc acc tat gtt tct gtt gga aca tca aca    674
Lys Leu Tyr Gln Asn Pro Thr Thr Tyr Val Ser Val Gly Thr Ser Thr
205                 210                 215                 220 ctg aac cag aga tcg gtc cca gaa ata gct acc agg ccc aaa gta aat    722
Leu Asn Gln Arg Ser Val Pro Glu Ile Ala Thr Arg Pro Lys Val Asn
                225                 230                 235 ggg caa agt gga aga ata gag ttt ttc tgg aca atc tta aag cca aat    770
Gly Gln Ser Gly Arg Ile Glu Phe Phe Trp Thr Ile Leu Lys Pro Asn
            240                 245                 250 gat gcc atc aat ttc gag agt aat gga aat ttt att gct cca gaa tat    818
Asp Ala Ile Asn Phe Glu Ser Asn Gly Asn Phe Ile Ala Pro Glu Tyr
        255                 260                 265 gca tac aaa att gcc aag aaa gga gac tca gca atc atg gaa agt gga    866
Ala Tyr Lys Ile Ala Lys Lys Gly Asp Ser Ala Ile Met Glu Ser Gly
    270                 275                 280 ttg gag tat ggt aac tgc aac acc aag tgt caa act cca atg ggt gca    914
Leu Glu Tyr Gly Asn Cys Asn Thr Lys Cys Gln Thr Pro Met Gly Ala
285                 290                 295                 300 ata aac tcc agc atg cca ttt cac aac ata cac cct ctc acc att ggg    962
Ile Asn Ser Ser Met Pro Phe His Asn Ile His Pro Leu Thr Ile Gly
                305                 310                 315 gaa tgc ccc aga tac gtg aag tca gat aga tta gtc ctt gca aca ggg    1010
Glu Cys Pro Arg Tyr Val Lys Ser Asp Arg Leu Val Leu Ala Thr Gly
            320                 325                 330 ctc agg aat gtc cct caa aga gaa aca aga gga cta ttt ggg gcc ata    1058
Leu Arg Asn Val Pro Gln Arg Glu Thr Arg Gly Leu Phe Gly Ala Ile
        335                 340                 345 gca ggc ttc ata gaa gga ggg tgg caa gga atg gta gac ggt tgg tat    1106
Ala Gly Phe Ile Glu Gly Gly Trp Gln Gly Met Val Asp Gly Trp Tyr
    350                 355                 360 gga tac cac cat agc aac aag caa ggg agt gga tac gct gca gac aaa    1154
Gly Tyr His His Ser Asn Lys Gln Gly Ser Gly Tyr Ala Ala Asp Lys
365                 370                 375                 380 gag tcc act caa aag gca ata gat gga atc act aat aag gtc aac tca    1202
Glu Ser Thr Gln Lys Ala Ile Asp Gly Ile Thr Asn Lys Val Asn Ser
                385                 390                 395 atc att gac aaa atg aac act cag ttt gag gcc gtt gga aag gaa ttt    1250
Ile Ile Asp Lys Met Asn Thr Gln Phe Glu Ala Val Gly Lys Glu Phe
            400                 405                 410 aat aac tta gaa agg agg ata gag aat ttg aac aag aaa atg gaa gac    1298
Asn Asn Leu Glu Arg Arg Ile Glu Asn Leu Asn Lys Lys Met Glu Asp
        415                 420                 425 gga ttc cta gat gtc tgg act tat aat gct gaa ctt ctg gtt ctc atg    1346
Gly Phe Leu Asp Val Trp Thr Tyr Asn Ala Glu Leu Leu Val Leu Met
```

```
                      430                 435                 440
gaa aat gag aga acc cta gac ttt cat gac tca aat gtc aag aac ctt         1394
Glu Asn Glu Arg Thr Leu Asp Phe His Asp Ser Asn Val Lys Asn Leu
445                 450                 455                 460 tac gac aag gtt cga cta cag ctt agg gat aat gca aag gag ctg ggt         1442
Tyr Asp Lys Val Arg Leu Gln Leu Arg Asp Asn Ala Lys Glu Leu Gly
                465                 470                 475 aat ggt tgt ttc gag ttc tat cac aaa tgt gat gat gaa tgt atg gca         1490
Asn Gly Cys Phe Glu Phe Tyr His Lys Cys Asp Asp Glu Cys Met Ala
            480                 485                 490 agt gta aga aac gga acg tat gac tac ccg cag tat tca gaa gag gca         1538
Ser Val Arg Asn Gly Thr Tyr Asp Tyr Pro Gln Tyr Ser Glu Glu Ala
        495                 500                 505 aga cta aac aga gag gaa ata agt gga gta aaa ttg gaa tca ata gga         1586
Arg Leu Asn Arg Glu Glu Ile Ser Gly Val Lys Leu Glu Ser Ile Gly
510                 515                 520 act tac caa ata ttg tca att tat tca aca gtg gcg agt tcc tta gca         1634
Thr Tyr Gln Ile Leu Ser Ile Tyr Ser Thr Val Ala Ser Ser Leu Ala
525                 530                 535                 540 ctg gca atc atg gta gct ggt cta tct ttc tgg atg tgc tcc aat gga         1682
Leu Ala Ile Met Val Ala Gly Leu Ser Phe Trp Met Cys Ser Asn Gly
                545                 550                 555 tca ttg caa tgc aga att tgc att taa acttgtgagt tcagattgta gtt           1732
Ser Leu Gln Cys Arg Ile Cys Ile
            560

<210> SEQ ID NO 50
<211> LENGTH: 564
<212> TYPE: PRT
<213> ORGANISM: Influenza A virus

<400> SEQUENCE: 2

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Trp Ser Tyr Ile Val
                85                  90                  95

Glu Lys Asp Ser Pro Ile Asn Gly Leu Cys Tyr Pro Gly Asp Phe Asn
            100                 105                 110

Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asp His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Asn Tyr Asn Asn Thr Asn Gln Glu Asp Leu Leu Val Leu Trp
            180                 185                 190

Gly Ile His His Pro Asn Asp Ala Thr Glu Gln Thr Lys Leu Tyr Gln
        195                 200                 205
```

-continued

```
Asn Pro Thr Thr Tyr Val Ser Val Gly Thr Ser Thr Leu Asn Gln Arg
    210                 215                 220
Ser Val Pro Glu Ile Ala Thr Arg Pro Lys Val Asn Gly Gln Ser Gly
225                 230                 235                 240
Arg Ile Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Ala Lys Lys Gly Asp Ser Ala Ile Met Glu Ser Gly Leu Glu Tyr Gly
        275                 280                 285
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Arg
305                 310                 315                 320
Tyr Val Lys Ser Asp Arg Leu Val Leu Ala Thr Gly Leu Arg Asn Val
                325                 330                 335
Pro Gln Arg Glu Thr Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Lys Gln Gly Ser Gly Tyr Ala Ala Asp Lys Glu Ser Thr Gln
    370                 375                 380
Lys Ala Ile Asp Gly Ile Thr Asn Lys Val Asn Ser Ile Ile Asp Lys
385                 390                 395                 400
Met Asn Thr Gln Phe Glu Ala Val Gly Lys Glu Phe Asn Asn Leu Glu
                405                 410                 415
Arg Arg Ile Glu Asn Leu Asn Lys Lys Met Glu Asp Gly Phe Leu Asp
            420                 425                 430
Val Trp Thr Tyr Asn Ala Glu Leu Leu Val Leu Met Glu Asn Glu Arg
        435                 440                 445
Thr Leu Asp Phe His Asp Ser Asn Val Lys Asn Leu Tyr Asp Lys Val
    450                 455                 460
Arg Leu Gln Leu Arg Asp Asn Ala Lys Glu Leu Gly Asn Gly Cys Phe
465                 470                 475                 480
Glu Phe Tyr His Lys Cys Asp Asp Glu Cys Met Ala Ser Val Arg Asn
                485                 490                 495
Gly Thr Tyr Asp Tyr Pro Gln Tyr Ser Glu Glu Ala Arg Leu Asn Arg
            500                 505                 510
Glu Glu Ile Ser Gly Val Lys Leu Glu Ser Ile Gly Thr Tyr Gln Ile
        515                 520                 525
Leu Ser Ile Tyr Ser Thr Val Ala Ser Ser Leu Ala Leu Ala Ile Met
    530                 535                 540
Val Ala Gly Leu Ser Phe Trp Met Cys Ser Asn Gly Ser Leu Gln Cys
545                 550                 555                 560
Arg Ile Cys Ile
```